(12) United States Patent
Kriwacki et al.

(10) Patent No.: US 7,704,703 B2
(45) Date of Patent: Apr. 27, 2010

(54) ARF AND HDM2 INTERACTION DOMAINS AND THE METHODS OF USE THEREOF

(75) Inventors: Richard Kriwacki, Memphis, TN (US); Brian Bothner, Bozeman, MT (US); William Lewis, Ames, IA (US)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 1068 days.

(21) Appl. No.: 10/489,802

(22) PCT Filed: Sep. 19, 2002

(86) PCT No.: PCT/US02/29780

§ 371 (c)(1), (2), (4) Date: Jul. 23, 2004

(87) PCT Pub. No.: WO03/025572

PCT Pub. Date: Mar. 27, 2003

(65) Prior Publication Data

US 2004/0248198 A1 Dec. 9, 2004

(51) Int. Cl.
*G01N 33/53* (2006.01)
(52) U.S. Cl. .................. 435/7.8; 435/7.1; 530/350; 530/300
(58) Field of Classification Search .................. None
See application file for complete search history.

(56) References Cited

U.S. PATENT DOCUMENTS 6,407,062 B1 * 6/2002 Sherr et al. .............. 514/12

FOREIGN PATENT DOCUMENTS

WO   WO 93/20238   * 10/1993

OTHER PUBLICATIONS

Wells, Biochemistry, vol. 29, pp. 8509-8517, 1990.*
Wu et al. (Genes and Development, vol. 7, pp. 1126-1132, 1993.*
Zindy et al. (Genes and Development, vol. 12, pp. 2424-2433, 1998).*
Greasley et al. (Nature Structural Biology, vol. 2, pp. 797-806 ,1995.*
Midgley, C.A., et al.,"An N-terminal p14$^{ARF}$ Peptide Blocks Mdm2-Dependent Ubiquitination in vitro and can Activate p53 in vivo," *Oncogene*, 2000, pp. 2312-2323, vol. 19.
Weber, J.D., et al., "Nucleolar Arf Sequesters Mdm2 and Activates p53," *Nature Cell Biology*, 1999, pp. 20-26, vol. 1.
Weber, J.D., et al., "Cooperative Signals Governing ARf-Mdm2 Interaction and Nucleolar Localization of the Complex," *Molecular and Cellular Biology*, 2000, pp. 2517-2528, vol. 20(7).
Oliner, J.D. et al., "Amplification of a Gene Encoding a p53-Associated Protein in Human Sarcomas," *Nature*, Jul. 2, 1992, pp. 80-83, vol. 358, w/alignment attached.

* cited by examiner

*Primary Examiner*—Hope A Robinson

(57) ABSTRACT

The present invention discloses that the binding of Arf with Dm2, important components of the p53 tumor suppressor pathway, results in specific domains of both proteins undergoing a dramatic transition from dynamically disordered conformations to amyloid-like structures comprised of anti-parallel β-strands. The invention exploits this discovery by providing unique methods for identifying and/or designing compounds that mimic, inhibit and/or enhance the effect of Arf on Dm2. The present invention also provides specific peptides derived from the binding domains of Arf and Dm2 which co-assemble into supramolecular structures comprised of binary anti-parallel β-strands. The disclosed peptides may represent structural prototypes for a broader class of peptides that is capable of assembly into supramolecular structures.

4 Claims, 8 Drawing Sheets

```
                    A1              A2
                    1      11       21       31
Human         MVRRFLVTLRIRRACGPPRVRVFVHIPRLTGEWAAP
Mouse         MGRRFLVTVRIQRAGRPLQERVFLVKFVRSRRPRTAS
Opossum       MIRVRVTVRVSRACRPHHVRIFVAKIVQALCRASAS Jnet pred.    ---EEEEEEEE-----------EEEEEEE------
Jnet conf.    10168998875089998743899872257876666
Solv. Exp.    BBBBBBBBBB--BB-B---BBBBBBBBB-B-----
```

FIG. 2a

```
              210       220       230       240       250       260       270                280        290       300
human         SSSSESTGTPSNPDLDA.GVSEHSGDWLDQDSVSDQFSVEFEVESLDSEDYSLSEEGQELSDED...DEVYQVTVYQAGESDTDSFEEDPEISLADYWK
mouse         SSSSESTETPSHQDLDD.GVSEHSGDCLDQDSVSDQFSVEFEVESLDSEDYSLSDEGHELSDED...DEVIRVTVYQTGESDTDSFEGDPEISLADYWK
hamster       SSSSESTDTPSNQDLDD.GVSEHSGDWLDQDSVSDQFSVEFEVESLDSEDYSLSEGGQELSDED...DEVRVTVYQSGESDVDSFEGDPEISLADYWK
horse         SSSSESTGTPSNPDLDA.GVSEHSGDWLDQDSVSDQFSVEFEVESLDSEDYSLSEEGQELSDED...DEVRVTVYQAGESDTDSFEEDPEISLADYWK
dog           SSSSESTGTPSNPDLDA.GVSEHSGDWLDQDSVSDQFSVEFEVESLDSEDYSLSEEGQELSDED...DEVRVTVYQAGESDTDSFEEDPEISLADYWK
chicken       SNSSDSTDSVSIPDLDDASSLSENS.DWFDHGSVSDDSDSDNFSVEFEVESIYSEDYSHNEEGQELTDED...DEVYQLTIYQDEDSDSFNEDPEISLADYWK
zebra fish    RGNSESSDANSMSDVGI.SRSEGSEESEDSDSDSDNFSVEFEVESINSDAYSEND.VDSVPGE...NEIYEVIIFA.E.DEDSFDEDTEITEADYKW
tree frog     GLRCDRNSSESTDSSSN.SDPERHSTNDNSEHDSDQFSVEFEVESVCSDDYSPSGDEHGVSEEEINDEVYQVTIYETEESETDSFDVDTEISEADYWK H1                                                      H2
Jnet pred.    ---EEEEEEEE-------------------------EEEEEEEEE--------------------HHHHHHH--
Jnet conf.    89999566999998876 6436789865568886612678846146754555567878778998 83368887468888888899847776542 8
Solv. exp.    ----B-----------B---BB-B-B----------B-B-B-B--------------------BB-BBBB----B-
```

| | | |
|---|---|---|
| Mouse: | mA1 | $^{3}$RRFLVT-VR$^{10}$ |
| | mA2 | $^{21}$RVFLVKFVR$^{29}$ |
| Human: | hA1 | $^{3}$RRFLVT-LR$^{10}$ |
| | hA2 | $^{21}$RVFVVH•IPR$^{29}$ |

"Arf motif"
consensus: RUFXV$Z_{1,2}$XR where U = R or V
X = L,P or V
Z = T, K, F, H or I

SEQUENCE LISTING

```
<160> NUMBER OF SEQ ID NOS: 27

<210> SEQ ID NO 1
<211> LENGTH: 713
<212> TYPE: DNA
<213> ORGANISM: Mus musculus
<220> FEATURE:
<221> NAME/KEY: CDS
<222> LOCATION: (43)...(549)

<400> SEQUENCE: 1
gtcacagtga ggccgccgct gagggagtac agcagcggga gc atg ggt cgc agg        54
                                                Met Gly Arg Arg
                                                 1 ttc ttg gtc act gtg agg att cag cgc gcg ggc cgc cca ctc caa gag     102
Phe Leu Val Thr Val Arg Ile Gln Arg Ala Gly Arg Pro Leu Gln Glu
  5                  10                  15                  20 agg gtt ttc ttg gtg aag ttc gtg cga tcc cgg aga ccc agg aca gcg     150
Arg Val Phe Leu Val Lys Phe Val Arg Ser Arg Arg Pro Arg Thr Ala
             25                  30                  35 agc tgc gct ctg gct ttc gtg aac atg ttg ttg agg cta gag agg atc     198
Ser Cys Ala Leu Ala Phe Val Asn Met Leu Leu Arg Leu Glu Arg Ile
         40                  45                  50 ttg aga aga ggg ccg cac cgg aat cct gga cca ggt gat gat gat ggg     246
```

```
Leu Arg Arg Gly Pro His Arg Asn Pro Gly Pro Gly Asp Asp Gly
         55                  60                  65 caa cgt tca cgt agc agc tct tct gct caa cta cgg tgc aga ttc gaa    294
Gln Arg Ser Arg Ser Ser Ser Ser Ala Gln Leu Arg Cys Arg Phe Glu
 70                  75                  80 ctg cga gga ccc cac tac ctt ctc ccg ccc ggt gca cga cgc agc gcg    342
Leu Arg Gly Pro His Tyr Leu Leu Pro Pro Gly Ala Arg Arg Ser Ala
 85                  90                  95                 100 gga agg ctt cct gga cac gct ggt ggt gct gca cgg gtc agg ggc tcg    390
Gly Arg Leu Pro Gly His Ala Gly Gly Ala Ala Arg Val Arg Gly Ser
                105                 110                 115 gct gga tgt gcg cga tgc ctg ggg tcg cct gcc gct cga ctt ggc cca    438
Ala Gly Cys Ala Arg Cys Leu Gly Ser Pro Ala Ala Arg Leu Gly Pro
            120                 125                 130 aga gcg ggg aca tca aga cat cgt gcg ata ttt gcg ttc cgc tgg gtg    486
Arg Ala Gly Thr Ser Arg His Arg Ala Ile Phe Ala Phe Arg Trp Val
        135                 140                 145 ctc ttt gtg ttc cgc tgg gtg gtc ttt gtg tac cgc tgg gaa cgt cgc    534
Leu Phe Val Phe Arg Trp Val Val Phe Val Tyr Arg Trp Glu Arg Arg
    150                 155                 160 cca gac cga cgg gca tagcttcagc tcaagcacgc ccagggccct ggaacttcgc    589
Pro Asp Arg Arg Ala
165 ggccaatccc aagagcagag ctaaatccgg cctcagcccg cctttttctt cttagcttca    649 cttctagcga tgctagcgtg tctagcatgt ggctttaaaa aatacataat aatgcttttt    709 tttt                                                                 713

<210> SEQ ID NO 2
<211> LENGTH: 169
<212> TYPE: PRT
<213> ORGANISM: Mus musculus

<400> SEQUENCE: 2

Met Gly Arg Arg Phe Leu Val Thr Val Arg Ile Gln Arg Ala Gly Arg
 1               5                  10                  15

Pro Leu Gln Glu Arg Val Phe Leu Val Lys Phe Val Arg Ser Arg Arg
             20                  25                  30

Pro Arg Thr Ala Ser Cys Ala Leu Ala Phe Val Asn Met Leu Leu Arg
         35                  40                  45

Leu Glu Arg Ile Leu Arg Arg Gly Pro His Arg Asn Pro Gly Pro Gly
     50                  55                  60

Asp Asp Gly Gln Arg Ser Arg Ser Ser Ser Ala Gln Leu Arg
65                  70                  75                  80

Cys Arg Phe Glu Leu Arg Gly Pro His Tyr Leu Leu Pro Pro Gly Ala
                 85                  90                  95

Arg Arg Ser Ala Gly Arg Leu Pro Gly His Ala Gly Gly Ala Ala Arg
            100                 105                 110

Val Arg Gly Ser Ala Gly Cys Ala Arg Cys Leu Gly Ser Pro Ala Ala
        115                 120                 125

Arg Leu Gly Pro Arg Ala Gly Thr Ser Arg His Arg Ala Ile Phe Ala
    130                 135                 140

Phe Arg Trp Val Leu Phe Val Phe Arg Trp Val Val Phe Val Tyr Arg
145                 150                 155                 160

Trp Glu Arg Arg Pro Asp Arg Arg Ala
                165
```

```
<210> SEQ ID NO 3
<211> LENGTH: 540
<212> TYPE: DNA
<213> ORGANISM: Homo sapiens
<220> FEATURE:
<221> NAME/KEY: CDS
<222> LOCATION: (142)...(537)

<400> SEQUENCE: 3
cgcgcctgcg gggcggagat gggcaggggg cggtgcgtgg gtcccagtct gcagttaagg      60
gggcaggagt ggcgctgctc acctctggtg ccaaagggcg gcgcagcggc tgccgagctc     120
ggccctggag gcggcgagaa c atg gtg cgc agg ttc ttg gtg acc ctc cgg       171
                         Met Val Arg Arg Phe Leu Val Thr Leu Arg
                           1               5                  10 att cgg cgc gcg tgc ggc ccg ccg cga gtg agg gtt ttc gtg gtt cac       219
Ile Arg Arg Ala Cys Gly Pro Pro Arg Val Arg Val Phe Val Val His
                 15                  20                  25 atc ccg cgg ctc acg ggg gag tgg gca gcg cca ggg gcg ccc gcc gct       267
Ile Pro Arg Leu Thr Gly Glu Trp Ala Ala Pro Gly Ala Pro Ala Ala
         30                  35                  40 gtg gcc ctc gtg ctg atg cta ctg agg agc cag cgt cta ggg cag cag       315
Val Ala Leu Val Leu Met Leu Leu Arg Ser Gln Arg Leu Gly Gln Gln
     45                  50                  55 ccg ctt cct aga aga cca ggt cat gat gat ggg cag cgc ccg agt ggc       363
Pro Leu Pro Arg Arg Pro Gly His Asp Asp Gly Gln Arg Pro Ser Gly
 60                  65                  70 gga gct gct gct gct cca cgg cgc gga gcc caa ctg cgc cga ccc cgc       411
Gly Ala Ala Ala Ala Pro Arg Arg Gly Ala Gln Leu Arg Arg Pro Arg
 75                  80                  85                  90 cac tct cac ccg acc cgt gca cga cgc tgc ccg gga ggg ctt cct gga       459
His Ser His Pro Thr Arg Ala Arg Arg Cys Pro Gly Gly Leu Pro Gly
                 95                 100                 105 cac gct ggt ggt gct gca ccg ggc cgg ggc gcg gct gga cgt gcg cga       507
His Ala Gly Gly Ala Ala Pro Gly Arg Gly Ala Ala Gly Arg Ala Arg
             110                 115                 120 tgc ctg ggg ccg tct gcc cgt gga cct ggc tga                           540
Cys Leu Gly Pro Ser Ala Arg Gly Pro Gly
         125                 130

<210> SEQ ID NO 4
<211> LENGTH: 132
<212> TYPE: PRT
<213> ORGANISM: Homo sapiens

<400> SEQUENCE: 4

Met Val Arg Arg Phe Leu Val Thr Leu Arg Ile Arg Arg Ala Cys Gly
  1               5                  10                  15

Pro Pro Arg Val Arg Val Phe Val Val His Ile Pro Arg Leu Thr Gly
             20                  25                  30

Glu Trp Ala Ala Pro Gly Ala Pro Ala Ala Val Ala Leu Val Leu Met
         35                  40                  45

Leu Leu Arg Ser Gln Arg Leu Gly Gln Gln Pro Leu Pro Arg Arg Pro
     50                  55                  60

Gly His Asp Asp Gly Gln Arg Pro Ser Gly Gly Ala Ala Ala Ala Pro
 65                  70                  75                  80

Arg Arg Gly Ala Gln Leu Arg Arg Pro Arg His Ser His Pro Thr Arg
                 85                  90                  95

Ala Arg Arg Cys Pro Gly Gly Leu Pro Gly His Ala Gly Gly Ala Ala
            100                 105                 110
```

-continued

Pro Gly Arg Gly Ala Ala Gly Arg Ala Arg Cys Leu Gly Pro Ser Ala
    115                 120                 125
Arg Gly Pro Gly
    130

<210> SEQ ID NO 5
<211> LENGTH: 1710
<212> TYPE: DNA
<213> ORGANISM: Mus musculus

<400> SEQUENCE: 5

| | | | | |
|---|---|---|---|---|
| gaggagccgc | cgccttctcg | tcgctcgagc | tctggacgac | catggtcgct caggccccgt | 60 |
| ccgcggggcc | tccgcgctcc | ccgtgaaggg | tcggaagatg | cgcgggaagt agcagccgtc | 120 |
| tgctgggcga | gcgggagacc | gaccggacac | ccctggggga | ccctctcgga tcaccgcgct | 180 |
| tctcctgcgg | cctccaggcc | aatgtgcaat | accaacatgt | ctgtgtctac cgagggtgct | 240 |
| gcaagcacct | cacagattcc | agcttcggaa | caagagactc | tggttagacc aaaaccattg | 300 |
| cttttgaagt | tgttaaagtc | cgttggagcg | caaaacgaca | cttacactat gaaagagatt | 360 |
| atattttata | ttggccagta | tattatgact | aagaggttat | atgacgagaa gcagcagcac | 420 |
| attgtgtatt | gttcaaatga | tctcctagga | gatgtgtttg | gagtcccgag tttctctgtg | 480 |
| aaggagcaca | ggaaaatata | tgcaatgatc | tacagaaatt | tagtggctgt aagtcagcaa | 540 |
| gactctggca | catcgctgag | tgagagcaga | cgtcagcctg | aaggtgggag tgatctgaag | 600 |
| gatcctttgc | aagcgccacc | agaagagaaa | ccttcatctt | ctgatttaat ttctagactg | 660 |
| tctacctcat | ctagaaggag | atccattagt | gagacagaag | agaacacaga tgagctacct | 720 |
| ggggagcggc | accggaagcg | ccgcaggtcc | ctgtcctttg | atccgagcct gggtctgtgt | 780 |
| gagctgaggg | agatgtgcag | cggcggcacg | agcagcagta | gcagcagcag cagcgagtcc | 840 |
| acagagacgc | cctcgcatca | ggatcttgac | gatggcgtaa | gtgagcattc tggtgattgc | 900 |
| ctggatcagg | attcagtttc | tgatcagttt | agcgtggaat | ttgaagttga gtctctggac | 960 |
| tcggaagatt | acagcctgag | tgacgaaggg | cacgagctct | cagatgagga tgatgaggtc | 1020 |
| tatcgggtca | cagtctatca | gacaggagaa | agcgatacag | actcttttga aggagatcct | 1080 |
| gagatttcct | tagctgacta | ttggaagtgt | acctcatgca | atgaaatgaa tcctccccctt | 1140 |
| ccatcacact | gcaaaagatg | ctggacccct | cgtgagaact | ggcttccaga cgataagggg | 1200 |
| aaagataaag | tggaaatctc | tgaaaaagcc | aaactggaaa | actcagctca ggcagaagaa | 1260 |
| ggcttggatg | tgcctgatgg | caaaaagctg | acagagaatg | atgctaaaga gccatgtgct | 1320 |
| gaggaggaca | gcgaggagaa | ggccgaacag | acgcccctgt | cccaggagag tgacgactat | 1380 |
| tcccaaccat | cgacttccag | cagcattgtt | tatagcagcc | aagaaagcgt gaaagagttg | 1440 |
| aaggaggaaa | cgcagcacaa | agacgagagt | gtggaatcta | gcttctcccct gaatgccatc | 1500 |
| gaaccatgtg | tgatctgcca | ggggcggcct | aaaaatggct | gcattgttca cggcaagact | 1560 |
| ggacacctca | tgtcatgttt | cacgtgtgca | aagaagctaa | aaaaaagaaa caagccctgc | 1620 |
| ccagtgtgca | gacagccaat | ccaaatgatt | gtgctaagtt | acttcaacta gctgacctgc | 1680 |
| tcacaaaaat | agaattttat | atttctaact | | | 1710 |

<210> SEQ ID NO 6
<211> LENGTH: 489
<212> TYPE: PRT
<213> ORGANISM: Mus musculus

<400> SEQUENCE: 6

```
Met Cys Asn Thr Asn Met Ser Val Ser Thr Glu Gly Ala Ala Ser Thr
 1               5                  10                  15

Ser Gln Ile Pro Ala Ser Glu Gln Glu Thr Leu Val Arg Pro Lys Pro
                20                  25                  30

Leu Leu Leu Lys Leu Leu Lys Ser Val Gly Ala Gln Asn Asp Thr Tyr
            35                  40                  45

Thr Met Lys Glu Ile Ile Phe Tyr Ile Gly Gln Tyr Ile Met Thr Lys
        50                  55                  60

Arg Leu Tyr Asp Glu Lys Gln Gln His Ile Val Tyr Cys Ser Asn Asp
65                  70                  75                  80

Leu Leu Gly Asp Val Phe Gly Val Pro Ser Phe Ser Val Lys Glu His
                85                  90                  95

Arg Lys Ile Tyr Ala Met Ile Tyr Arg Asn Leu Val Ala Val Ser Gln
                100                 105                 110

Gln Asp Ser Gly Thr Ser Leu Ser Glu Ser Arg Arg Gln Pro Glu Gly
            115                 120                 125

Gly Ser Asp Leu Lys Asp Pro Leu Gln Ala Pro Pro Glu Glu Lys Pro
130                 135                 140

Ser Ser Ser Asp Leu Ile Ser Arg Leu Ser Thr Ser Ser Arg Arg Arg
145                 150                 155                 160

Ser Ile Ser Glu Thr Glu Glu Asn Thr Asp Glu Leu Pro Gly Glu Arg
                165                 170                 175

His Arg Lys Arg Arg Arg Ser Leu Ser Phe Asp Pro Ser Leu Gly Leu
            180                 185                 190

Cys Glu Leu Arg Glu Met Cys Ser Gly Gly Thr Ser Ser Ser Ser Ser
            195                 200                 205

Ser Ser Ser Glu Ser Thr Glu Thr Pro Ser His Gln Asp Leu Asp Asp
    210                 215                 220

Gly Val Ser Glu His Ser Gly Asp Cys Leu Asp Gln Asp Ser Val Ser
225                 230                 235                 240

Asp Gln Phe Ser Val Glu Phe Glu Val Glu Ser Leu Asp Ser Glu Asp
                245                 250                 255

Tyr Ser Leu Ser Asp Glu Gly His Glu Leu Ser Asp Glu Asp Asp Glu
                260                 265                 270

Val Tyr Arg Val Thr Val Tyr Gln Thr Gly Glu Ser Asp Thr Asp Ser
    275                 280                 285

Phe Glu Gly Asp Pro Glu Ile Ser Leu Ala Asp Tyr Trp Lys Cys Thr
    290                 295                 300

Ser Cys Asn Glu Met Asn Pro Pro Leu Pro Ser His Cys Lys Arg Cys
305                 310                 315                 320

Trp Thr Leu Arg Glu Asn Trp Leu Pro Asp Asp Lys Gly Lys Asp Lys
                325                 330                 335

Val Glu Ile Ser Glu Lys Ala Lys Leu Glu Asn Ser Ala Gln Ala Glu
            340                 345                 350

Glu Gly Leu Asp Val Pro Asp Gly Lys Lys Leu Thr Glu Asn Asp Ala
        355                 360                 365

Lys Glu Pro Cys Ala Glu Glu Asp Ser Glu Glu Lys Ala Glu Gln Thr
    370                 375                 380

Pro Leu Ser Gln Glu Ser Asp Asp Tyr Ser Gln Pro Ser Thr Ser Ser
385                 390                 395                 400

Ser Ile Val Tyr Ser Ser Gln Glu Ser Val Lys Glu Leu Lys Glu Glu
                405                 410                 415
```

```
Thr Gln His Lys Asp Glu Ser Val Glu Ser Ser Phe Ser Leu Asn Ala
            420                 425                 430

Ile Glu Pro Cys Val Ile Cys Gln Gly Arg Pro Lys Asn Gly Cys Ile
        435                 440                 445

Val His Gly Lys Thr Gly His Leu Met Ser Cys Phe Thr Cys Ala Lys
    450                 455                 460

Lys Leu Lys Lys Arg Asn Lys Pro Cys Pro Val Cys Arg Gln Pro Ile
465                 470                 475                 480

Gln Met Ile Val Leu Ser Tyr Phe Asn
                485

<210> SEQ ID NO 7
<211> LENGTH: 2372
<212> TYPE: DNA
<213> ORGANISM: Homo sapiens

<400> SEQUENCE: 7
```

| | | | | | |
|---|---|---|---|---|---|
| gcaccgcgcg | agcttggctg | cttctggggc | ctgtgtggcc | ctgtgtgtcg | gaaagatgga     60 |
| gcaagaagcc | gagcccgagg | ggcggccgcg | accctctga | ccgagatcct | gctgctttcg   120 |
| cagccaggag | caccgtccct | ccccggatta | gtgcgtacga | gcgcccagtg | ccctggcccg   180 |
| gagagtggaa | tgatccccga | ggcccagggc | gtcgtgcttc | cgcagtagtc | agtccccgtg   240 |
| aaggaaactg | gggagtcttg | agggaccccc | gactccaagc | gcgaaaaccc | cggatggtga   300 |
| ggagcaggca | aatgtgcaat | accaacatgt | ctgtacctac | tgatggtgct | gtaaccacct   360 |
| cacagattcc | agcttcggaa | caagagaccc | tggttagacc | aaagccattg | cttttgaagt   420 |
| tattaaagtc | tgttggtgca | caaaaagaca | cttatactat | gaagagggtt | cttttttatc   480 |
| ttggccagta | tattatgact | aaacgattat | atgatgagaa | gcaacaacat | attgtatatt   540 |
| gttcaaatga | tcttctagga | gatttgtttg | gcgtgccaag | cttctctgtg | aaagagcaca   600 |
| ggaaaatata | taccatgatc | tacaggaact | tggtagtagt | caatcagcag | gaatcatcgg   660 |
| actcaggtac | atctgtgagt | gagaacaggt | gtcaccttga | aggtgggagt | gatcaaaagg   720 |
| accttgtaca | agagcttcag | gaagagaaac | cttcatcttc | acatttggtt | tctagaccat   780 |
| ctacctcatc | tagaaggaga | gcaattagtg | agacagaaga | aaattcagat | gaattatctg   840 |
| gtgaacgaca | agaaaacgc | cacaaatctg | atagtatttc | cctttccttt | gatgaaagcc   900 |
| tggctctgtg | tgtaataagg | gagatatgtt | gtgaagaag | cagtagcagt | gaatctacag   960 |
| ggacgccatc | gaatccggat | cttgatgctg | gtgtaagtga | acattcaggt | gattggttgg  1020 |
| atcaggattc | agtttcagat | cagtttagtg | tagaatttga | agttgaatct | ctcgactcag  1080 |
| aagattatag | ccttagtgaa | gaaggacaag | aactctcaga | tgaagatgat | gaggtatatc  1140 |
| aagttactgt | gtatcaggca | ggggagagtg | atacagattc | atttgaagaa | gatcctgaaa  1200 |
| tttccttagc | tgactattgg | aaatgcactt | catgcaatga | aatgaatccc | cccttccat  1260 |
| cacattgcaa | cagatgttgg | gcccttcgtg | agaattggct | tcctgaagat | aaagggaaag  1320 |
| ataaagggga | aatctctgag | aaagccaaac | tggaaaactc | aacacaagct | gaagagggct  1380 |
| tgatgttcc | tgattgtaaa | aaactatag | tgaatgattc | cagagagtca | tgtgttgagg  1440 |
| aaaatgatga | taaaattaca | caagcttcac | aatcacaaga | aagtgaagac | tattctcagc  1500 |
| catcaacttc | tagtagcatt | atttatagca | gccaagaaga | tgtgaaagag | tttgaagggg  1560 |
| aagaaaccca | agacaaagaa | gagagtgtgg | aatctagttt | gccccttaat | gccattgaac  1620 |
| cttgtgtgat | ttgtcaaggt | cgacctaaaa | atggttgcat | tgtccatggc | aaaacaggac  1680 |

-continued

```
atcttatggc ctgctttaca tgtgcaaaga agctaaagaa aaggaataag ccctgcccag    1740
tatgtagaca accaattcaa atgattgtgc taacttattt cccctagttg acctgtctat    1800
aagagaatta tatatttcta actatataac cctaggaatt tagacaacct gaaatttatt    1860
cacatatatc aaagtgagaa aatgcctcaa ttcacataga tttcttctct ttagtataat    1920
tgacctactt tggtagtgga atagtgaata cttactataa tttgacttga atatgtagct    1980
catcctttac accaactcct aatttttaaat aatttctact ctgtcttaaa tgagaagtac    2040 ttggttttttt ttttcttaaa tatgtatatg acatttaaat gtaacttatt attttttttg    2100
agaccgagtc ttgctctgtt acccaggctg gagtgcagtg ggtgatcttg gctcactgca    2160
agctctgccc tccccgggtt cgcaccattc tcctgcctca gcctcccaat tagcttggcc    2220
tacagtcatc tgccaccaca cctggctaat ttttgtact tttagtagag acagggtttc     2280
accgtgttag ccaggatggt ctcgatctcc tgacctcgtg atccgcccac ctcggcctcc    2340
caaagtgctg ggattacagg catgagccac cg                                  2372
```

<210> SEQ ID NO 8
<211> LENGTH: 491
<212> TYPE: PRT
<213> ORGANISM: Homo sapiens

<400> SEQUENCE: 8

```
Met Cys Asn Thr Asn Met Ser Val Pro Thr Asp Gly Ala Val Thr Thr
  1               5                  10                  15

Ser Gln Ile Pro Ala Ser Glu Gln Glu Thr Leu Val Arg Pro Lys Pro
             20                  25                  30

Leu Leu Leu Lys Leu Leu Lys Ser Val Gly Ala Gln Lys Asp Thr Tyr
         35                  40                  45

Thr Met Lys Glu Val Leu Phe Tyr Leu Gly Gln Tyr Ile Met Thr Lys
     50                  55                  60

Arg Leu Tyr Asp Glu Lys Gln Gln His Ile Val Tyr Cys Ser Asn Asp
 65                  70                  75                  80

Leu Leu Gly Asp Leu Phe Gly Val Pro Ser Phe Ser Val Lys Glu His
                 85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255
```

```
Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
            275                 280                 285

Asp Ser Phe Glu Glu Asp Pro Glu Ile Ser Leu Ala Asp Tyr Trp Lys
            290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350

Ala Glu Glu Gly Phe Asp Val Pro Asp Cys Lys Lys Thr Ile Val Asn
            355                 360                 365

Asp Ser Arg Glu Ser Cys Val Glu Glu Asn Asp Asp Lys Ile Thr Gln
            370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Gly Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 9
<211> LENGTH: 8
<212> TYPE: PRT
<213> ORGANISM: Mus musculus

<400> SEQUENCE: 9

Arg Arg Phe Leu Val Thr Val Arg
1               5

<210> SEQ ID NO 10
<211> LENGTH: 9
<212> TYPE: PRT
<213> ORGANISM: Mus musculus

<400> SEQUENCE: 10

Arg Val Phe Leu Val Lys Phe Val Arg
1               5

<210> SEQ ID NO 11
<211> LENGTH: 8
<212> TYPE: PRT
<213> ORGANISM: Homo sapiens

<400> SEQUENCE: 11

Arg Arg Phe Leu Val Thr Leu Arg
1               5
```

```
<210> SEQ ID NO 12
<211> LENGTH: 9
<212> TYPE: PRT
<213> ORGANISM: Homo sapiens

<400> SEQUENCE: 12

Arg Val Phe Val Val His Ile Pro Arg
 1               5

<210> SEQ ID NO 13
<211> LENGTH: 9
<212> TYPE: PRT
<213> ORGANISM: Artificial Sequence
<220> FEATURE:
<223> OTHER INFORMATION: Arf Motif
<220> FEATURE:
<221> NAME/KEY: VARIANT
<222> LOCATION: (2)...(2)
<223> OTHER INFORMATION: X can be R or V
<220> FEATURE:
<221> NAME/KEY: VARIANT
<222> LOCATION: (4)...(4)
<223> OTHER INFORMATION: X can be L, P, or V
<220> FEATURE:
<221> NAME/KEY: VARIANT
<222> LOCATION: (6)...(6)
<223> OTHER INFORMATION: X can be T, K, F, H, or I
<220> FEATURE:
<221> NAME/KEY: VARIANT
<222> LOCATION: (7)...(7)
<223> OTHER INFORMATION: X can be T, K, F, H, I, or no amino acid
<220> FEATURE:
<221> NAME/KEY: VARIANT
<222> LOCATION: (8)...(8)
<223> OTHER INFORMATION: X can be L, P, or V

<400> SEQUENCE: 13

Arg Xaa Phe Xaa Val Xaa Xaa Xaa Arg
 1               5

<210> SEQ ID NO 14
<211> LENGTH: 4
<212> TYPE: PRT
<213> ORGANISM: Artificial Sequence
<220> FEATURE:
<223> OTHER INFORMATION: Consensus sequence for nucleolar localization
      sequence

<400> SEQUENCE: 14

Arg Arg Pro Arg
 1

<210> SEQ ID NO 15
<211> LENGTH: 37
<212> TYPE: PRT
<213> ORGANISM: Homo sapiens

<400> SEQUENCE: 15

Met Val Arg Arg Phe Leu Val Thr Leu Arg Ile Arg Arg Ala Cys Gly
 1               5                  10                  15

Pro Pro Arg Val Arg Val Phe Val Val His Ile Pro Arg Leu Thr Gly
                 20                  25                  30

Glu Trp Ala Ala Pro
             35

<210> SEQ ID NO 16
<211> LENGTH: 37
<212> TYPE: PRT
```

<213> ORGANISM: Mus musculus

<400> SEQUENCE: 16

Met Gly Arg Arg Phe Leu Val Thr Val Arg Ile Gln Arg Ala Gly Arg
1               5                   10                  15

Pro Leu Gln Glu Arg Val Phe Leu Val Lys Phe Val Arg Ser Arg Arg
                20                  25                  30

Pro Arg Thr Ala Ser
        35

<210> SEQ ID NO 17
<211> LENGTH: 37
<212> TYPE: PRT
<213> ORGANISM: Monodelphis domestica

<400> SEQUENCE: 17

Met Ile Arg Arg Val Arg Val Thr Val Arg Val Ser Arg Ala Cys Arg
1               5                   10                  15

Pro His His Val Arg Ile Phe Val Ala Lys Ile Val Gln Ala Leu Cys
                20                  25                  30

Arg Ala Ser Ala Ser
        35

<210> SEQ ID NO 18
<211> LENGTH: 95
<212> TYPE: PRT
<213> ORGANISM: Homo sapiens

<400> SEQUENCE: 18

Ser Ser Ser Ser Glu Ser Thr Gly Thr Pro Ser Asn Pro Asp Leu Asp
1               5                   10                  15

Ala Gly Val Ser Glu His Ser Gly Asp Trp Leu Asp Gln Asp Ser Val
                20                  25                  30

Ser Asp Gln Phe Ser Val Glu Phe Glu Val Glu Ser Leu Asp Ser Glu
        35                  40                  45

Asp Tyr Ser Leu Ser Glu Glu Gly Gln Glu Leu Ser Asp Glu Asp Asp
50                  55                  60

Glu Val Tyr Gln Val Thr Val Tyr Gln Ala Gly Glu Ser Asp Thr Asp
65                  70                  75                  80

Ser Phe Glu Glu Asp Pro Glu Ile Ser Leu Ala Asp Tyr Trp Lys
                85                  90                  95

<210> SEQ ID NO 19
<211> LENGTH: 95
<212> TYPE: PRT
<213> ORGANISM: Mus musculus

<400> SEQUENCE: 19

Ser Ser Ser Ser Glu Ser Thr Glu Thr Pro Ser His Gln Asp Leu Asp
1               5                   10                  15

Asp Gly Val Ser Glu His Ser Gly Asp Cys Leu Asp Gln Asp Ser Val
                20                  25                  30

Ser Asp Gln Phe Ser Val Glu Phe Glu Val Glu Ser Leu Asp Ser Glu
        35                  40                  45

Asp Tyr Ser Leu Ser Asp Glu Gly His Glu Leu Ser Asp Glu Asp Asp
50                  55                  60

Glu Val Tyr Arg Val Thr Val Tyr Gln Thr Gly Glu Ser Asp Thr Asp
65                  70                  75                  80

```
Ser Phe Glu Gly Asp Pro Glu Ile Ser Leu Ala Asp Tyr Trp Lys
                85                  90                  95
```

<210> SEQ ID NO 20
<211> LENGTH: 95
<212> TYPE: PRT
<213> ORGANISM: Cricetus sp.

<400> SEQUENCE: 20

```
Ser Ser Ser Ser Glu Ser Thr Asp Thr Pro Ser Asn Gln Asp Leu Asp
1               5                   10                  15

Asp Gly Val Ser Glu His Ser Gly Asp Trp Leu Asp Gln Asp Ser Val
                20                  25                  30

Ser Asp Gln Phe Ser Val Glu Phe Glu Val Glu Ser Leu Asp Ser Glu
            35                  40                  45

Asp Tyr Ser Leu Ser Glu Gly Gln Glu Leu Ser Asp Glu Asp Asp
        50                  55                  60

Glu Val Tyr Arg Val Thr Val Tyr Gln Ser Gly Glu Ser Asp Val Asp
65                  70                  75                  80

Ser Phe Glu Gly Asp Pro Glu Ile Ser Leu Ala Asp Tyr Trp Lys
                85                  90                  95
```

<210> SEQ ID NO 21
<211> LENGTH: 95
<212> TYPE: PRT
<213> ORGANISM: Equus caballus

<400> SEQUENCE: 21

```
Ser Ser Ser Ser Glu Ser Thr Gly Thr Pro Ser Asn Pro Asp Leu Asp
1               5                   10                  15

Ala Gly Val Ser Glu His Ser Gly Asp Trp Leu Asp Gln Asp Ser Val
                20                  25                  30

Ser Asp Gln Phe Ser Val Glu Phe Glu Val Glu Ser Leu Asp Ser Glu
            35                  40                  45

Asp Tyr Ser Leu Ser Glu Glu Gly Gln Glu Leu Ser Asp Glu Asp Asp
        50                  55                  60

Glu Val Tyr Arg Val Thr Val Tyr Gln Ala Gly Glu Ser Asp Thr Asp
65                  70                  75                  80

Ser Phe Glu Glu Asp Pro Glu Ile Ser Leu Ala Asp Tyr Trp Lys
                85                  90                  95
```

<210> SEQ ID NO 22
<211> LENGTH: 95
<212> TYPE: PRT
<213> ORGANISM: Canis familiaris

<400> SEQUENCE: 22

```
Ser Ser Ser Ser Glu Ser Thr Gly Thr Pro Ser Asn Pro Asp Leu Asp
1               5                   10                  15

Ala Gly Val Ser Glu His Ser Gly Asp Trp Leu Asp Gln Asp Ser Val
                20                  25                  30

Ser Asp Gln Phe Ser Val Glu Phe Glu Val Glu Ser Leu Asp Ser Glu
            35                  40                  45

Asp Tyr Ser Leu Ser Glu Glu Gly Gln Glu Leu Ser Asp Glu Asp Asp
        50                  55                  60

Glu Val Tyr Arg Val Thr Val Tyr Gln Ala Gly Glu Ser Asp Thr Asp
65                  70                  75                  80

Ser Phe Glu Glu Asp Pro Glu Ile Ser Leu Ala Asp Tyr Trp Lys
```

<210> SEQ ID NO 23
<211> LENGTH: 95
<212> TYPE: PRT
<213> ORGANISM: Gallus gallus

<400> SEQUENCE: 23

```
Ser Asn Ser Ser Asp Ser Thr Asp Ser Val Ser Ile Pro Asp Leu Asp
 1               5                  10                  15

Ala Ser Ser Leu Ser Glu Asn Ser Asp Trp Phe Asp His Gly Ser Val
                20                  25                  30

Ser Asp Gln Phe Ser Val Glu Phe Glu Val Glu Ser Ile Tyr Ser Glu
            35                  40                  45

Asp Tyr Ser His Asn Glu Glu Gly Gln Glu Leu Thr Asp Glu Asp
 50                  55                  60

Glu Val Tyr Gln Leu Thr Ile Tyr Gln Asp Glu Asp Ser Asp Ser Asp
 65                  70                  75                  80

Ser Phe Asn Glu Asp Pro Glu Ile Ser Leu Ala Asp Tyr Trp Lys
                85                  90                  95
```

<210> SEQ ID NO 24
<211> LENGTH: 90
<212> TYPE: PRT
<213> ORGANISM: Danio rerio

<400> SEQUENCE: 24

```
Arg Gly Asn Ser Glu Ser Ser Asp Ala Asn Ser Asn Ser Asp Val Gly
 1               5                  10                  15

Ile Ser Arg Ser Glu Gly Ser Glu Glu Ser Glu Ser Asp Ser Asp Ser Asp
                20                  25                  30

Ser Asp Asn Phe Ser Val Glu Phe Glu Val Glu Ser Ile Asn Ser Asp
            35                  40                  45

Ala Tyr Ser Glu Asn Asp Val Asp Ser Val Pro Gly Glu Asn Glu Ile
 50                  55                  60

Tyr Glu Val Thr Ile Phe Ala Glu Asp Glu Asp Ser Phe Asp Glu Asp
 65                  70                  75                  80

Thr Glu Ile Thr Glu Ala Asp Tyr Lys Trp
                85                  90
```

<210> SEQ ID NO 25
<211> LENGTH: 98
<212> TYPE: PRT
<213> ORGANISM: Boophis sp.

<400> SEQUENCE: 25

```
Gly Leu Arg Cys Asp Arg Asn Ser Ser Glu Ser Thr Asp Ser Ser Ser
 1               5                  10                  15

Asn Ser Asp Pro Glu Arg His Ser Thr Asn Asp Asn Ser Glu His Asp
                20                  25                  30

Ser Asp Gln Phe Ser Val Glu Phe Glu Val Glu Ser Val Cys Ser Asp
            35                  40                  45

Asp Tyr Ser Pro Ser Gly Asp Glu His Gly Val Ser Glu Glu Glu Glu
 50                  55                  60

Ile Asn Asp Glu Val Tyr Gln Val Thr Ile Tyr Glu Thr Glu Glu Ser
 65                  70                  75                  80

Glu Thr Asp Ser Phe Asp Val Asp Thr Glu Ile Ser Glu Ala Asp Tyr
                85                  90                  95
```

```
Trp Lys

<210> SEQ ID NO 26
<211> LENGTH: 14
<212> TYPE: PRT
<213> ORGANISM: Homo sapiens

<400> SEQUENCE: 26

Met Val Arg Arg Phe Leu Val Thr Leu Arg Ile Arg Arg Ala
 1               5                  10

<210> SEQ ID NO 27
<211> LENGTH: 15
<212> TYPE: PRT
<213> ORGANISM: Homo sapiens

<400> SEQUENCE: 27

Ser Val Ser Asp Gln Phe Ser Val Glu Phe Glu Val Glu Ser Leu
 1               5                  10                  15
```

ARF AND HDM2 INTERACTION DOMAINS AND THE METHODS OF USE THEREOF

RESEARCH SUPPORT

The research leading to the present invention was supported in part by the American Cancer Society and a Cancer Center (CORE) Support Grant CA21765. The government may have certain rights in the present invention. Support for this invention was also provided by the AMERICAN LEBANESE SYRIAN ASSOCIATED CHARITIES and the ASSISI FOUNDATION OF MEMPHIS INC.

CROSS-REFERENCE TO RELATED APPLICATIONS

This application is a national state entry of PCT/US02/29780 filed on Sep. 19, 2002, which claims the benefit of U.S. Utility application Ser. No. 09/956,425, filed Sep. 19, 2001, now abandoned, each of which is herein incorporated by reference in their entirety.

FIELD OF THE INVENTION

The present invention relates to the interaction of Arf and Hdm2, as well as to specific protein fragments/peptides derived from Arf and Hdm2 that play a critical role in the binding of these two regulatory proteins. The present invention also relates to the use of Arf and Hdm2 and specific fragments thereof in unique assays for identifying compounds that can be used in the treatment of cancer and for the design of synthetic analogs or two-component self-assembly tags that are capable of promoting biomolecular assembly. The present invention provides specific peptides derived from the binding domains of Arf and Hdm2 which coassemble into amyloid-like fibrils. The disclosed peptides may represent structural prototypes for a class of peptides that is capable of promoting the formation of supramolecular assemblies comprising amyloid-like fibrils.

BACKGROUND OF THE INVENTION

Disruption of cell cycle control mechanisms contributes significantly to the development of cancer in humans [Sherr, Cancer Res., 60:3689-95 (2000)]. Consistently, the two most frequently inactivated tumor suppressor genes in human cancer irrespective of tumor type, site, and patient age, are the p53 gene and the INK4a-Arf gene locus, both of which encode proteins involved in the regulation of cellular replication [Hall and Peters, Adv. Cancer Res., 68:67-108 (1996); Hainaut et al., Nucleic Acid Res., 25:151-157 (1997)]. The p53 gene encodes the transcription factor p53. Activation of the p53 gene in response to oncogenic stress signals results in cell cycle arrest or apoptosis, thereby enabling cells to repair genotoxic damage or alternatively, to be eliminated from the organism [reviewed in Ko et al., Genes & Devel. 10:1054-1072 (1996); Levine, Cell 88:323-331 (1997)]. Loss of p53 function cancels these surveillance functions thereby allowing defective cells to replicate and predisposing the cell to cancer development.

The $^{INK4a}$/Arf gene locus has been shown to encode two unrelated proteins from alternative but partially overlapping reading frames: (i) p16$^{INK4a}$ and (ii) Arf (p14$^{Arf}$ in humans and p19$^{ARF}$ in the mouse) [Quelle et al., Cell, 83:993-1000 (1995)]. These proteins independently target two cell cycle control pathways. The N-terminal 62 amino acid residues of the 132 amino acid p14$^{ARF}$ protein and the N-terminal 63 amino acid residues of the 169 amino acid p19$^{ARF}$ protein are encoded by a unique first exon (1β), whereas the remaining amino acid residues are encoded by exon 2. An alternative reading frame of exon 2 also encodes the bulk of p16$^{INK4a}$.

p16$^{INK4a}$ is an antagonist of cell replication. More specifically, p16$^{INK4a}$ inhibits the cyclin D-dependent kinases CDK4 and CDK6 [Serrano et al., Nature, 366:704-707 (1993)]. CDK4 and CDK6 play an important role in the cell replication cycle through their phosphorylation of the retinoblastoma protein (Rb). Hyperphosphorylation of Rb stimulates the cell to exit from the G1 phase and begin DNA synthesis, a required step prior to cell division. Thus, the inhibition of CDK4 and CDK6 by p16$^{INK4a}$ prevents hyperphosphorylated Rb-dependent DNA synthesis, thereby maintaining the cell in its non-replicating mode.

Disruption in mice of either the entire INK4a/Arf locus [Serrano et al., Cell, 85: 27-37 (1996)] or exon 1β [Kamijo et al., Cell, 91:649-59 (1997)] leads to multi-type tumor growth and early death, identifying Arf as a bona fide tumor suppressor. Interestingly, it has been suggested that disruption of INK4a does not contribute to spontaneous tumor formation in mice and that Arf disruption accounts for the high rate of spontaneous tumor formation in INK4a/Arf-null mice [Sherr, Cancer Res., 60: 3689-95 (2000)]. Since the INK4a/Arf locus is frequently disrupted in human cancers [Raus and Peters, Biochim. Biophys. Acta Rev. Cancer, 1378:F115-F177 (1998)], the loss of Arf function appears to be a major contributor to human cancers.

Indeed, Arf, in concert with other cell cycle regulators and tumor suppressors such as p53 and Rb, plays a central role in cellular responses to oncogenic stress, such as inappropriate mitogenic signaling. For example, Arf expression is activated by overexpression of proteins involved in mitogenic signaling, such as Myc [Zindy et al., Genes & Dev., 12:2424-2434 (1998)], E1A [de Stancbina et al., Genes Dev., 12:2434-42 (1998)], E2F [Bates et al., Nature, 395:124-5 (1998)], Ras [Palmero et al., Nature, 395:125-6 (1998)], and v-Ab1 [Radfar et al., Proc. Natl. Acad. Sci. U.S.A., 95:13194-13199 (1998)]. Activation of Arf leads to stabilization of p53 [Pomerantz et al., Cell, 92:713-23 (1998); Kamijo et al., Proc. Natl. Acad Sci., 95:8292-8297 (1998); Stott et al., Embo J, 17: 5001-14 (1998); and Zhang et al., Cell, 92:725-734 (1998)] followed by cell cycle arrest. Arf therefore connects the Rb and p53 pathways [Sherr, Cancer Res., 60: 3689-95 (2000)] so that excessive proliferative signaling via the Rb pathway activates arrest mechanisms controlled by p53.

Arf stabilizes p53 by interfering with an auto-regulatory loop involving p53 and Double Minute 2 (Hdm2 in humans, Mdm2 in mice) [Wu et al., Genes Dev., 7:1126-1132 (1993)] that maintains p53 at low levels under normal cellular conditions (i.e. in the absence of oncogenic stress, DNA damage, etc.). The positive component of this auto-regulatory loop involves activation of Mdm2 transcription by p53 [Barak et al., EMBO J, 12:461-468 (1993)]. The negative component has several facets. First, Mdm2 binds p53 [Kussie et al., Science, 274:948-953 (1996)] and inhibits the transactivation function of p53 [Oliner et al., Nature, 362:857-860 (1993); Momand et al., Cell, 69:1237-1245 (1992)]. Second, Mdm2 shuttles p53 from the nucleus to the cytoplasm and facilitates p53 degradation [Roth et al., Embo J, 17:554-64 (1998)]; Freedman et al., Mol Cell Biol, 18:7288-93 (1998)]. Third, Mdm2 acts as an E3 ubiquitin ligase toward p53 within the ubiquitin-dependent 26S proteosome pathway [Honda et al., FEBS Lett, 420:25-7 (1997)]. Therefore, Mdm2 inhibits p53 activity in the nucleus through multiple and diverse mechanisms. Balance between the positive and negative components of this auto-regulatory system is essential for cell survival. When p53 is inactivated, mice develop tumors at an unusually high rate [Donehower et al., *Nature*, 356:215-221 (1992)], indicating that p53-dependent tumor suppression is compromised. Additionally, when Mdm2 is inactivated, mice are not viable [Jones et al., *Nature*, 378:206-8 (1995); Montes de Oca Luna et al., *Nature*, 378:203-206 (1995)], suggesting that unregulated p53 expression is lethal. $Mdm2^{-/-}$ mice are rescued, however, by the additional inactivation of p53 [Jones et al., *Nature*, 378:206-8 (1995); Montes de Oca Luna et al., *Nature*, 378:203-206 (1995)]. Thus, proper regulation of p53 activity relies on appropriate balance between the positive and negative components of the p53-Mdm2 auto-regulatory system.

The first direct biochemical connection between $p19^{ARF}$ and p53 was established when it was found that $p19^{ARF}$ could bind to Mdm2, [Pomerantz et al., *Cell*, 92:713-723 (1998); Zhang et al., *Cell*, 92:725-734 (1998)]. Arf was subsequently found to inhibit the negative components of the p53-Mdm2 auto-regulatory loop by interfering with several of Mdm2's activities toward p53. First, by binding Mdm2, Arf inhibits Mdm2-dependent nucleo-cytoplasmic shuttling of p53 which leads to stabilization and activation of p53 [Tao et al., *Proc Natl Acad Sci USA*, 96:6937-41 (1999)]. Second, Arf inhibits the E3 ubiquitin ligase activity of Mdm2 toward p53 in vitro [Honda et al., *Embo J*, 18:22-7 (1999); Midgley et al., *Oncogene*, 19:2312-23 (2000)] and is thought to be an important aspect of Arf-dependent activation of p53 in vivo [Midgley et al., *Oncogene*, 19:2312-23 (2000); Llanos et al., *Nat. Cell Biol.*, 3:445-452 (2001)]. Finally, Arf binds and sequesters Mdm2 in the nucleolus, physically separating Mdm2 and p53 in different sub-cellular compartments [Weber et al., *Nat. Cell Biol.*, 1:20-26 (1999); Lohrum et al., *Nat. Cell Biol.*, 2:179-81 (2000); Weber et al., *Mol. Cell. Biol.*, 20:2517-2528 (2000)]. The relative importance of these three mechanisms to Arf-dependent stabilization and activation of p53 is a matter of debate. For example, a recent report shows that Mdm2 binding but not nucleolar localization is the functional property of Arf that is required for p53 activation [Llanos et al., *Nat. Cell Biol.*, 3:445-452 (2001)]. This report, however, does not rule out earlier reports that nucleolar co-localization of Arf and Mdm2 contribute to p53 stabilization through sequestration [Weber et al., *Nat. Cell Biol.*, 1:20-26 (1999)]. It is likely that Arf acts via several mechanisms to stabilize p53 and these have evolved in concert with the multiplicity of Mdm2's effects on p53. Importantly, direct interaction between Arf and Hdm2 is required for the multiple mechanisms of p53 stabilization.

Therefore, there is a need to further characterize the Arf-Hdm2 complex. In addition, there is a need to determine the specific domains of Arf and Hdm2 that are involved in this complex. Furthermore, there is a need to identify compounds that can mimic the effect of Arf on Hdm2, since the absence of functional Arf is commonplace in tumor cells. Alternatively, there is a need to identify compounds that inhibit the binding of Arf to Hdm2 to prevent undesired activation of p53-dependent pathways by, for example, DNA damaging agents, in normal cells.

The citation of any reference herein should not be deemed as an admission that such reference is available as prior art to the instant invention.

SUMMARY OF THE INVENTION

Through disclosing that the binding of Arf with Hdm2 results in specific domains of both proteins undergoing a dramatic transition from disordered conformations to extended structures comprised of β-strands, the present invention provides new insight towards the identification/design of novel anti-cancer therapeutics and synthetic analogs or two-component self-assembly tags that are capable of promoting biomolecular assembly.

In one embodiment the present invention provides unique assays for identifying compounds that mimic and/or enhance, or alternatively inhibit the effect of Arf on Hdm2. In an alternative embodiment, the invention discloses the formation of binary, extended β-strands as a novel mechanism of biomolecular assembly. It is envisioned that the anti-parallel β-strand-containing fibrils formed from these peptides may allow the directed assembly of decorated fibrils which could be utilized as biological nanostructures.

In a related aspect of the present invention specific protein fragments derived from Arf and Hdm2 that play a direct role in the binding of these two important regulatory proteins are provided. More specifically, the present invention provides specific peptides derived from the binding domains of the tumor suppressor protein $p14^{Arf}$ and the cellular oncoprotein Hdm2 which co-assemble into amyloid-like fibrils.

The disclosures that short peptide (i.e. 14 or 15 amino acids in length) derived from Arf and Hdm2 co-assemble into amyloid-like fibrils provides a novel mechanism for the formation of biomolecular complexes.

Therefore, the present invention provides methods of identifying a compound that can induce β-strand assembly of Dm2 (e.g., Hdm2 or Mdm2). One such method comprises contacting the compound with Dm2 or an inducible fragment of Dm2 (e.g., a fragment of Dm2 that is capable of being induced to β-strand assembly by Arf) and then determining whether Dm2 or the inducible fragment of Dm2 is induced to form a β-strand assembly by the compound. A compound is identified when Dm2 or the inducible fragment of Dm2 is induced to form a β-strand assembly. In a particular embodiment, a peptide or protein comprising the Arf motif (i.e., the amino acid sequence of SEQ ID NO:13) responsible for inducing β strand assembly in Hdm2, can be used as a positive control.

The present invention also provides methods of identifying a compound that can enhance the rate of β-strand assembly of Dm2 induced by Arf. One such embodiment comprises contacting the compound with Dm2 or an inducible fragment of Dm2, and Arf or an inducing fragment of Arf and then determining the rate of the β-strand assembly of Dm2 or of the inducible fragment of Dm2. A compound is identified that can enhance the rate of β-strand assembly of Dm2 induced by Arf when the rate of the β-strand assembly of Dm2 or of the inducible fragment of Dm2 increases in the presence of the compound relative to in the absence of the compound.

The present invention further provides methods of identifying a compound that can inhibit the formation of β-strand assembly of Dm2. In a particular embodiment of this type the compound is contacted with Dm2 or an inducible fragment of Dm2, and Arf or an inducing fragment of Arf, and the rate of formation of a β-strand assembly of Dm2 or the inducible fragment of Dm2 is determined. A compound is identified that can inhibit the formation of β-strand assembly of Dm2 when the rate of formation of the β-strand assembly of Dm2 and/or the rate of formation of the β-strand assembly of the inducible fragment of Dm2 decreases in the presence of the compound relative to in its absence.

In a related embodiment, the compound is contacted with Dm2 or an inducible fragment of Dm2, and Arf or an inducing fragment of Arf, and the amount of formation of a β-strand assembly of Dm2 or the inducible fragment of Dm2 is determined. A compound is identified that can inhibit the formation of β-strand assembly of Dm2 when the amount of formation of the β-strand assembly of Dm2 or the inducible fragment of Dm2 decreases in the presence of the compound relative to in its absence.

In a particular embodiment, the inducing and/or inhibiting of β-strand assembly of Dm2 or the inducible fragment of Dm2 is determined by circular dichroism (CD) measurements. In another embodiment, the inducing and/or inhibiting of β-strand assembly of Dm2 or the inducible fragment of Dm2 is determined by nuclear magnetic resonance (NMR) measurements. In yet another embodiment, the inducing and/or inhibiting of β-strand assembly of Dm2 or the inducible fragment of Dm2 is determined by Fourier Transform Infrared (FTIR) spectroscopy. In still another embodiment, the inducing and/or inhibiting of β-strand assembly of Dm2 or the inducible fragment of Dm2 is determined by fluorescence spectroscopy. In another embodiment the natural fluorescence of one or more tryptophan residues in Dm2 are used to monitor the induction and/or inhibition of β-strand assembly. In one such embodiment changes in the intensity, wavelength, and/or anisotropy of tryptophan emission are used to monitor the binding of Arf to Dm2 and the formation of β-strand assemblies. In an alternative embodiment, a fluorescent probe, such as TEXAS RED® ($C_{31}H_{29}S_2N_2O_6Cl_1$) is covalently bound to either Dm2 or Arf. Changes in the fluorescence intensity, excitation and/or emission wavelength, and/or anisotropty of the probe can be monitored when the unlabeled and labeled species are mixed together.

The present invention also provides methods of identifying a compound that can induce supramolecular assemblies comprised of β-strands of Dm2 or a inducible fragment of Dm2 (e.g., Hdm2 or Mdm2). One such method comprises contacting the compound with Dm2 or an inducible fragment of Dm2 that is capable of being induced to form supramolecular assemblies by Arf, and then determining whether the compound induces Dm2 or the inducible fragment of Dm2 to form supramolecular assemblies. A compound is identified when Dm2 or the inducible fragment of Dm2 is induced to form supramolecular assemblies. In a particular embodiment, a peptide or protein comprising the Arf motif, (i.e., the amino acid sequence of SEQ ID NO:13) can be used as a positive control. In one embodiment, the inducing of supramolecular assemblies of Dm2 or the inducible fragment of Dm2 is determined by size exclusion measurements. In a preferred embodiment of this type, the inducing of supramolecular assemblies of Dm2 or the inducible fragment of Dm2 is determined by gel filtration chromatography.

In one embodiment, the Dm2 used in the methods of the invention is Hdm2 In a preferred embodiment of this type, the Hdm2 comprises the amino acid sequence of SEQ ID NO:8. In still another embodiment, the inducible fragment of Hdm2 comprises amino acid residues 235-259 of SEQ ID NO:8, which is the H1 segment. In a related embodiment, the inducible fragment of Hdm2 comprises amino acid residues 275-289 of SEQ ID NO:8, which is the H2 segment. In a preferred embodiment, the inducible fragment of Hdm2 comprises both amino acid residues 235-259 and amino acid residues 275-289 of SEQ ID NO:8.

The present invention also provides a compound that is identified by a method of the present invention. Preferably the compound does not comprise five or more consecutive amino acids of a naturally occurring protein. More preferably the compound is neither an amino acid nor made up of animal acids (i.e., a compound which is not a peptide). Even more preferably, the compound is a small molecule that that has a molecular weight of less than 3 Kilodaltons.

In related embodiments, compounds can be tested for their ability to either enhance the effect of Arf or alternatively interfere with the formation of the Arf-Dm2 complex using similar protocols as outlined above except both Arf or an inducing fragment of Arf, and Dm2 or an inducible fragment of Dm2 are included in the assay.

The formation of supramolecular assemblies and/or β-strand assembly can be readily monitored, e.g., by NMR, CD, FTIR, fluorescence and/or size exclusion. Therefore, a compound can be contacted with the Arf and Dm2 (and/or fragments thereof) and the amount of formation of the supramolecular assemblies and/or β-strand assembly of the Arf-Dm2 can be determined. When the compound decreases or eliminates the supramolecular assemblies and/or β-strand assembly of the Arf-Dm2 complex, the compound is identified as an inhibitor of the Arf-Dm2 interaction. Similarly the kinetics of the rate of formation of the supramolecular assemblies and/or β-strand assembly can be measured, and compounds can be assayed to select inhibitors or enhancers of the rate of formation of the supramolecular assemblies and/or β-strand assembly, as exemplified herein.

All of the methods for identifying compounds of the present invention can be performed by adding a compound to the assay solution at any time during the assay, including making additions at multiple times. Thus the compound can be added: (i) prior to the addition of Arf and/or an inducing fragment of Arf; and/or (ii) prior to the addition of Dm2 and/or an inducible fragment of Dm2; and/or (iii) together with Arf and/or an inducing fragment of Arf; and/or (iv) together with Dm2 and/or an inducible fragment of Dm2; and/or (v) after the addition of Arf and/or an inducing fragment of Arf; and/or (vi) after the addition of Dm2 and/or an inducible fragment of Dm2.

In addition the present invention provides methods of designing compounds that are predicted to mimic, enhance or alternatively inhibit the Arf-induced formation of β-strand assembly of Dm2. One such method comprises defining the structure of the Arf-Dm2 complex by using computer-based molecular modeling and docking techniques. In this approach, ensembles of molecular models for segments of Arf (for example, the Arf motif; or the segments of human or mouse Arf embodied by this motif) and Dm2 (for example, the H1 and/or H2 segments) are generated that are consistent with CD and FT-IR spectra for the Arf-Dm2 complex, namely that the polypeptide backbone torsion angles adopt values allowed in β-strands. Then, each member of the Arf ensemble is systematically docked with each member of the Dm2 ensemble using programs such as DOCK, or AUTODOCK. During the docking stage of the procedure, the binding energy for each of a large number of alternative Arf-Dm2 binding configurations is calculated and the docked configurations ranked according to binding energy. The Arf-Dm2 binding models with the lowest overall binding energy will then be used to design and/or identify a compound that is predicted to mimic, enhance, or alternatively inhibit the Arf-induced formation of β-strand assembly of Dm2.

As the skilled artisan would readily recognize, compounds designed and/or identified by this method can then be synthesized (if necessary) and tested in any of a number of assays, including those described above. For example, in one such embodiment the method further comprises contacting the compound with Dm2 or an inducible fragment of Dm2 and then determining whether Dm2 or the inducible fragment of Dm2 is induced to form a β-strand assembly. The compound is identified as a mimic of Arf if Dm2 or the inducible fragment of Dm2 is induced to form a β-strand assembly.

The present invention further provides methods of treating patients with cancer and/or patients having a predisposition for developing cancer. In a particular embodiment of this type, the patient has a tumor with cells that are characterized by a lack of sufficient Arf activity (e.g., lacking of a functional Arf), but still retain functional p53. One specific embodiment comprises administering to a patient a compound that mimics and/or enhances Arf activity that was identified by a method of the present invention. In a related embodiment, a compound is administered that can induce β-strand assembly of Dm2 in a cell that is lacking a functional Arf protein and/or sufficient Arf activity to de-repress the repression of p53 mediated apoptosis by Dm2 and thereby arrest cell growth.

By disclosing that peptides derived from Arf and Hdm2 coassemble into amyloid-like fibrils the present invention provides the basis for designing a two-component self-assembly tags that can be tethered to other macromolecules, including biomacromolecules, thereby allowing the assembly of derivatized amyloid-like fibrils. The directed assembly method contemplated herein relies on the disclosed formation of binary, extended β-strands as the basis of a novel mechanism of biomolecular assembly. It is further envisioned that the disclosed peptides may constitute structural prototypes for a broader class of peptides that may similarly self-assemble into fibrilar structures. Accordingly, the A1 and H1 peptides disclosed and claimed herein could provide prototypes for the design of synthetic analogs that are capable of assembly into supramolecular structures comprising anti-parallel β-strands. More specifically, it is envisioned that the anti-parallel β-strand-containing fibrils assembled as the result of the interaction of a fusion protein or synthetic analog comprising the A1 (SEQ ID NO:26) and H1 (SEQ ID NO:27) peptides disclosed herein could facilitate the directed assembly of decorated fibrils for use as biological nanostructures.

More specifically, the invention provides a method of preparing a biomacromolecular structure comprising the steps of preparing a binary mixture containing a first and second macromolecule, each of which is capable of assembly into a protofibril, wherein each of the biomolecules comprises a self-assembly tag comprising a peptide consisting of either the amino acid sequence of SEQ ID NO:26 or SEQ ID NO:27. In one embodiment of this aspect of the invention, it is contemplated that the first and second macromolecules will self-assemble into a biomolecular structure comprising amyloid-like fibrils. In a particular embodiment it envisioned that the resulting amyloid-like fibrils will comprise anti-parallel β-strands.

The present invention also provides a method of preparing a biological nanostructure comprising co-assembling macromolecules capable of undergoing a disorder-to-order transition upon binding. This embodiment of the invention contemplates the use of the A1 and H1 peptides disclosed herein as self-assembly tags that are capable of directing the assembly of macromolecules into a supramolecular structure. More specifically, it is contemplated that the disclosed peptides provide the basis of a novel mechanism of biomolecular assembly that can be exploited to promote the directed assembly of decorated fibrils. In a particular embodiment, it is contemplated that the disclosed method can be used to prepare biological nanostructures comprising extended β-strands.

For example, the disclosed method can be used to prepare a biological nanostructure comprising co-assembling a first and a second polypeptides capable of undergoing a disorder-to-order transition upon binding wherein the first polypeptide comprises a fusion protein which comprises a peptide consisting of an amino acid sequence according to SEQ ID NO:26 and the second polypeptide comprises a fusion protein which comprises a peptide consisting of an amino acid sequence according to SEQ ID NO:27 and further wherein the polypeptides coassemble into a fibrilar structure.

The invention further provides a method of directing the self-assembly of polypeptides into amyloid-like fibrils. In one embodiment, this aspect of the invention can be practiced by the preparing a binary mixture of fusion proteins consisting of a first protein which comprises a peptide consisting of an amino acid sequence according to SEQ ID NO:26 and a second protein which comprises a peptide consisting of an amino acid sequence according to SEQ ID NO:27. In light of the fact that pure proteins are known to participate in the formation of amyloid-like fibrils it is envisioned that the first and second polypeptides used to prepare the fusion proteins can comprise the same or different amino acid sequences. In a particular embodiment of this aspect of the invention, the first and second polypeptides differ from each other and are prepared from the binding domain of two polypeptides which participate in a binding interaction. For example, as exemplified herein, the first polypeptide can be a tumor suppressor protein and the second polypeptide may be a cellular oncoprotein.

The present invention also provides specific fragments of the Arf and Dm2 proteins and peptides comprising the amino acid sequences of such fragments that can induce β-strand assembly of Dm2. Fusion proteins (including chimeric proteins) comprising these fragments/peptides are also provided, as are nucleic acids encoding such fragments/peptides, and corresponding fusion proteins. Preferably the fragments/peptides are between 8 and 50 amino acids in length. In one such embodiment the fragment/peptide comprises and/or consists of the amino acid sequence of SEQ ID NO:13. In a particular embodiment of this type, the fragment/peptide comprises and/or consists of the amino acid sequence of SEQ ID NO:9. In another embodiment of this type, the fragment/peptide comprises and/or consists of the amino acid sequence of SEQ ID NO:10. In yet another embodiment, the fragment/peptide comprises and/or consists of the amino acid sequence of SEQ ID NO:11. In still another embodiment of this type, the fragment/peptide comprises and/or consists of the amino acid sequence of SEQ ID NO:12.

As shown herein, short polypeptide segments within the tumor suppressor protein, p14Arf, and the cellular oncoprotein, Hdm2, mediate their specific interaction both in vitro and in cells [Bothner, B.; Lewis, W. S.; DiGiammarino, E. L.; Weber, J. D.; Bothner, S. J.; Kriwacki, R. W., *J. Mol. Biol.* 314:263-277 (2001); Weber, J. D.; Kuo, M. L.; Bothner, B.; DiGiammarino, E. L.; Kriwacki, R. W.; Roussel, M. F.; Sherr, C. J., *Mol. Cell. Biol.* 20:2517-2528 (2000); and Midgley, C. A.; Desterro, J. M.; Saville, M. K.; Howard, S.; Sparks, A.; Hay, R. T.; Lane, D. P., *Oncogene* 19:2312-2323 (2000)]. More specifically, it is disclosed that two arginine-rich motifs termed A1 (SEQ ID NO:11) and A2 (SEQ ID NO:12) within the Arf N-terminus mediate binding to Hdm2 while two acidic residue-rich segments termed H1 and H2 within the central domain of Hdm2 mediate binding to Arf. In the context of 37 and 95 amino acid fragments of Arf (SEQ ID NO:15) and Hdm2 (SEQ ID NO:18), respectively, these domains are shown to be disordered in solution while retaining biological activity [DiGiammarino, E. L.; Filippov, L; Weber, J. D.; Bothner, B.; Kriwacki, R. W., *Biochem.* 40:2379-2386 (2001); Bothner, B.; Lewis, W. S.; DiGiammarino, E. L.; Weber, J. D.; Bothner, S. J.; Kriwacki, R. W., *J. Mol. Biol.* 314:263-277 (2001)].

In a preferred embodiment the fragment/peptide comprises or alternatively consists of two or more segments of the Arf protein each segment comprising and/or consisting of the amino acid sequence of SEQ ID NO:13. In one embodiment of this type, the fragment/peptide comprises and/or consists of both the amino acid sequence of SEQ ID NO:9 and SEQ ID NO:10. In another embodiment, the fragment/peptide comprises and/or consists of both the amino acid sequence of SEQ ID NO:11 and SEQ ID NO:12. In still another embodiment, the fragment/peptide comprises and/or consists of both the amino acid sequence of SEQ ID NO:9 and SEQ ID NO:12. In yet another embodiment, the fragment/peptide comprises and/or consists of both the amino acid sequence of SEQ ID NO:10 and SEQ ID NO:11.

The present invention further provides specific peptides derived from the interacting domains of p14$^{Arf}$ (SEQ ID NO:26, referred to herein as the A1 peptide) and Hdm2 (SEQ ID NO:27) referred to herein as the H1 peptide) that can self-assemble into amyloid-like protofibrils comprised of anti-parallel B-strands. The amino acid sequences of the peptides are: A1 (SEQ ID NO:26; MVRRFLVTLRIRRA), and H1 (SEQ ID NO:27; SVSDQFSVEFEVESL).

It is to be understood that because it is possible that other biologically significant interactions may be mediated by a similar co-assembly mechanism, the disclosed peptides may constitute structural prototypes for a broader class of peptides that are capable of directing self-assembly of macromolecular components into fibrilar structures. Thus, it is envisioned that the disclosed peptides may be used as two-component self-assembly tags which can be tethered to other biomacromolecules and direct the assembly of derivitized/decorated fibrils. Accordingly, the disclosed peptides can be used as the basis of a method of directing the assembly of biological nanostructures.

In addition to peptides comprising the Arf segments described above, the invention also provides compositions comprised of at least one pair of the peptide segments described above linked together by a non-peptide linkage, e.g., a non-peptide chemical linkage.

In a related embodiment, the present invention provides a fragment/peptide that comprises and/or consists of amino acid residues 235-259 of SEQ ID NO:8. In still another embodiment of this type the fragment/peptide comprises and/or consists of amino acid residues 275-289 of SEQ ID NO:8. In a preferred embodiment, the fragment/peptide comprises and/or consists of amino acid residues 235-259 and amino acid residues 275-289 of SEQ ID NO:8.

In another aspect of the present invention, antibodies raised against specific fragments/peptides of Arf and/or Dm2 are provided. In one such embodiment the antibody is raised against a fragment/peptide comprising an amino acid sequence of SEQ ID NO:13. In another embodiment, the antibody is raised against a fragment/peptide comprising amino acid residues 235-259 of SEQ ID NO:8. In yet another embodiment, the antibody is raised against a fragment/peptide comprising amino acid residues 275-289 of SEQ ID NO:8. In a preferred embodiment, the antibody is raised against a fragment/peptide comprising amino acid residues 235-259 and amino acid residues 275-289 of SEQ ID NO:8. In one embodiment, the antibody is a polyclonal antibody. In another embodiment, the antibody is a monoclonal antibody. In still another embodiment, the antibody is a chimeric and/or humanized antibody.

The present invention further provides methods of inducing apoptosis in a cell. In one such embodiment, apoptosis is induced by administering an antibody of the present invention to a cell. In a preferred embodiment of this type the antibody is a humanized antibody. In a related embodiment, apoptosis is induced by administering a compound identified by a method of the present invention to the cell.

The present invention further provides methods of treating a patient for which induced apoptosis in targeted cells is a desirable treatment, such as various forms of cancer in which p53 is functional and Dm2 is overexpressed and/or p53 is functional and Arf is not functional. One or both of these conditions is thought to be a contributing factor in the development of a wide variety of cancers, including acute myeloid leukemia [Faderl, et al. Cancer, 89:1976-82 (2000)], breast cancer [Takami et al. Breast Cancer, 30: 95-102 (1994)], Burkitt lymphoma [Lindstrom et al. Oncogene, 20: 2117-7 (2001)], clear cell renal cell carcinoma [Haitel et al. Clin. Cancer Res., 6: 1840-4 (2000)], colon carcinomas [Burri et al. Lab. Invest., 81: 217-29 (2001)], ependymomas [Suzuki and Iwaki Mod. Pathol. 13:548-53 (2000)], gastric cancer [Villaseca et al. Rev. Med. Chil., 128:127-36 (2000)], glioblastoma [Fulci et al. Oncogene, 19: 3816-22 (2000)], Hodgkin's disease [Kupper et al. Br. J. Haematol., 112: 768-75 (2001)], intrahepatic cholangiocarcinoma [Horie. Archet al Virchows., 437: 25-30 (2000)], intimal sarcomas arising in the pulmonary artery [Bode-Lesniewska et al. Virchows. Arch., 438: 57-65 (2001)], malignant pleural mesothelioma [Yang et al. Cancer Res., 61: 5959-63 (2001)], melanoma-neural system tumour syndrome [Randerson-Moor et al. Hum. Molec. Genet., 10: 55-62 (2001)], non-Hodgkin's lymphomas [Pagnano et al. Am. J. Hematol., 67: 84-92 (2001)], non-small cell lung carcinomas [Gorgoulis et al. Mol. Med., 6:208-37 (2000)], ovarian tumors [Palazzo et al. Hum. Pathol., 31: 698-704 (2000)], oral cancer [Ralhan et al. Am. J. Pathol., 157: 587-96 (2000)], oral squamous cell carcinoma [Sano et al. Pathol. Int., 50: 709-16 (2000)], paragangliomas [Lam et al. J. Clin. Pathol., 54: 443-8 (2001)], phaeochromocytomas [Lam et al. J. Clin. Pathol., 54: 443-8 (2001)], primary central nervous system lymphomas [Nakamura et al. Cancer Res., 61: 6335-39 (2001)], prostate carcinoma [Leite et al. Mod. Pathol. 14: 428-36 (2001)], soft tissue sarcoma [Bartel et al. Int. J. Cancer, 95:168-75 (2001)], and urinary bladder carcinoma [Ioachim et al. Histol. Histopathol., 15: 721-7 (2000)].

One such method comprises administering an antibody of the present invention to a patient. Preferably, the treatment is administered to a patient that has a tumor containing cells characterized by the presence of functional Hdm2, and functional p53.

The present invention also provides kits for identifying a compound that can induce β-strand assembly of Dm2 in the absence and/or presence of Arf. One such kit comprises a fragment of Hdm2 that comprises amino acid residues 235-259 of SEQ ID NO:8. In another embodiment, the kit comprises a fragment of Hdm2 that comprises amino acid residues 275-289 of SEQ ID NO:8. In a particular embodiment the kit comprises a fragment of Hdm7 that comprises amino acid residues 235-259 and amino acid residues 275-289 of SEQ ID NO:8. In another embodiment a peptide that comprises the amino acid sequence of SEQ ID NO:13 is also included. Preferably this peptide comprises two copies of the amino acid sequence of SEQ ID NO:13. More preferably the kit further comprises instructions for identifying a compound that can induce β-strand assembly of Dm2.

Accordingly, it is a principal object of the present invention to provide an assay for selecting drugs that can be used to treat cancer.

It is a further object of the present invention to provide agents that can mimic and/or enhance the ability of Arf to stimulate β-strand assembly of Dm2.

It is a further object of the present invention to provide peptides consisting of defined minimal domains of Arf and Dm2 that are necessary and sufficient for Arf-Dm2 binding.

It is a further object of the present invention to provide methods of treating diseases that are adversely affected by the existence of cells that do not contain sufficient Arf activity.

It is a further object of the present invention to provide methods of identifying agents that can interfere with the ability of Arf to bind Dm2, including antibodies to Arf or Dm2.

It is a further object of the present invention to provide agents that can interfere with the ability of Arf to bind Dm2.

It is a further object of the present invention to provide antibodies that can interfere with the ability of Arf to bind Dm2.

These and other aspects of the present invention will be better appreciated by reference to the following drawings and Detailed Description.

BRIEF DESCRIPTION OF THE SEQUENCES

| SEQ ID NO: | TYPE | ORGANISM | PROTEIN |
|---|---|---|---|
| 1 | Nucleic Acid | Mouse | Arf |
| 2 | Amino Acid | Mouse | Arf |
| 3 | Nucleic Acid | Human | Arf |
| 4 | Amino Acid | Human | Arf |
| 5 | Nucleic Acid | Mouse | Mdm2 |
| 6 | Amino Acid | Mouse | Mdm2 |
| 7 | Nucleic Acid | Human | Hdm2 |
| 8 | Amino Acid | Human | Hdm2 |
| 9 | Amino Acid | Mouse | mA1 |
| 10 | Amino Acid | Mouse | mA2 |
| 11 | Amino Acid | Human | hA1 |
| 12 | Amino Acid | Human | hA2 |
| 13 | Amino Acid | Consensus | Arf Motif |
| 14 | Amino Acid | Consensus | RRPR |
| 15 | Amino Acid | Human | N-terminal 1-37 of Arf |
| 16 | Amino Acid | Mouse | N-terminal 1-37 of Arf |
| 17 | Amino Acid | Opossum | N-terminal 1-37 of Arf |
| 18 | Amino Acid | Human | ~210-304 of Dm2 |
| 19 | Amino Acid | Mouse | ~210-304 of Dm2 |
| 20 | Amino Acid | Hamster | ~210-304 of Dm2 |
| 21 | Amino Acid | Horse | ~210-304 of Dm2 |
| 22 | Amino acid | Dog | ~210-304 of Dm2 |
| 23 | Amino Acid | Chicken | ~210-304 of Dm2 |
| 24 | Amino Acid | Zebrafish | ~210-304 of Dm2 |
| 25 | Amino Acid | Tree Frog | ~210-304 of Dm2 |
| 26 | Amino Acid | Human | A1 peptide |
| 27 | Amino Acid | Human | H1 peptide |

BRIEF DESCRIPTION OF THE DRAWINGS

FIGS. 2a-2c show the structure prediction for Arf and Hdm2 binding domains. Alignment of sequences for residues 1-37 of human (SEQ ID NO:15), mouse (SEQ ID NO:16) and opossum (SEQ ID NO:17) Arf (FIG. 2a) and~residues 210-304 of Mdm2 (FIG. 2b) from several species listed in THE BRIEF DESCRIPTION OF THE SEQUENCES above, corresponding to SEQ ID NOs:18-25. Residues that are underlined are conserved in all sequences and those in bold type are conserved in several sequences. The program Jnet was used to predict secondary structure and solvent exposure within the aligned regions. The secondary structure predictions are labeled "Jnet pred."; β-strand secondary structure is abbreviated "E", α-helix "H", and random coil "-". The prediction confidence score is labeled "Jnet conf.", with 0 the lowest and 9 the highest confidence values. The prediction of solvent exposure is labeled "Solv. Exp.", with "B" indicating that a residue is predicted to be less than 25% solvent exposed and "-" indicating greater than 25% solvent exposure. The schematic illustration of peptides derived from Hdm2 210-304 that bind mArfN37 is shown in FIG. 2c.

FIG. 4 shows the "Arf motif" (consensus sequence, SEQ ID NO:13). A short sequence of 8 or 9 amino acids is repeated twice in mouse (SEQ ID NO: 9 and 10) and human Arf (SEQ ID NO: 11 and 12). An alternating hydrophobic/charge pattern mediates binding.

FIG. 6a provides the CD spectra of A1 alone (line) and after repetitive additions of H1 (solid circle, solid triangle, solid square and hatched line). FIG. 6b provides the CD spectra of H1 alone (line) and after repetitive additions of A1 (solid circle, solid triangle, solid square and hatched line). Insets show that binding was saturable with a maximum β-strand content at ~1:1 molar ratio.

FIG. 7a provides a Fourier transform infrared (FT-IR) spectrum of A1/H1 co-assemblies that is consistent with anti-parallel β-strand secondary structure. Absorbance maxima in the protein amide I region were observed at 1618 cm-1 and 1679 cm-1. FIG. 7b provides the second-derivative analysis of FR-IR spectrum provided in panel a.

(FIG. 8a). The structure of the A1/H1 peptide coassemblies become organized after heating at 70° C., pH 3.5 for 100 hours. Samples were dried onto freshly glow-discharged, carbon-coated, EM grids and negatively-stained with 2% phosphotungstic acid (pH 6.4) (FIG. 8b).

DETAILED DESCRIPTION OF THE INVENTION

Figure 1A:
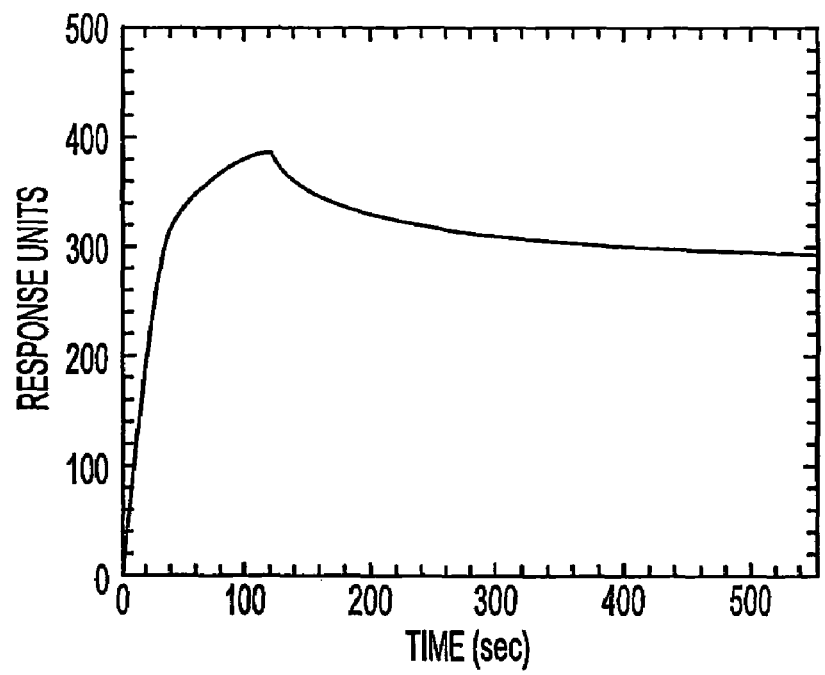
FIGS. 1a-1b show the surface plasmon resonance sensograms of Hdm2 constructs binding to mArfN37. His-tagged mArfN37 was immobilized on the SPR biosensor surface using a covalently linked His antibody. Binding of Hdm2 210-304 of SEQ ID NO:8 (FIG. 1a) and Hdm2 210-275 of SEQ ID NO:8 (FIG. 1b).

Isolated Arf and Hdm2 domains are dynamically disordered in solution, yet they retain the ability to interact in vitro and in cellular assays. As shown below, upon binding, domains of both Arf and Hdm2 undergo a dramatic transition from disordered conformations to extended structures comprised of β-strands. The presence of domains from both proteins is necessary and sufficient for the formation of the highly stable extended β structures. Sites within Arf and Hdm2 that interact at a resolution of 5 amino acids have been mapped using surface plasmon resonance (SPR). SPR and circular dichroism (CD) spectropolarimetry confirm the presence of multiple interaction domains within each protein (see Example below).

As disclosed herein, small peptide segments are identified within Arf and Hdm2 that are responsible for the interactions of these two proteins and mediate their nucleolar localization. Furthermore, pure Arf and Hdm2 are both shown to be dynamically disordered in solution but that, when mixed in vitro, they adopt highly stable β-sheet structures. The β-structures prepared in vitro, however, are extended networks and are relevant to the structures that form when Arf and Hdm2 interact in cells within the nucleoplasm and/or nucleoli.

Both p14$^{Arf}$ (human) and p19$^{Arf}$ (mouse) interact with Hdm2 through two short motifs present in their N-termini. The Arf interacting region of Hdm2 is also composed of two short sequences located in the central acidic domain, between residues 235-264 and 270-289 of SEQ ID NO:8. The binding-induced structural transition is also induced by short peptides, 15 amino acids in length, which contain the binding motifs. Micro-injection and live cell imaging of proteins tagged with fluorescent labels was used to confirm the in vivo function of the interaction domains. Arf and Hdm2 thus appear to interact through a novel mechanism that exerts control over the cell division cycle. A detailed analysis of Arf/Hdm2 interactions is disclosed herein. The present invention therefore provides unique opportunities for the development of anticancer therapeutics due to the novel interaction between Dm2 and Hdm2 and the limited size of the protein domains involved.

Protein fragments of Arf and Hdm2 have been identified that mediate binding and that can play a role in regulating Hdm2's repressor function toward p53. Using this information, it is now possible to inhibit p53 destruction by disrupting inter-domain interactions within Hdm2 with molecules that mimic and/or enhance Arf function. The Arf motif is relatively small, and may be mimicked by yet smaller molecules. Similarly, the molecular targets of this motif, the H1 and H2 segments of Hdm2, are small. These findings provide a method for searching for small molecules that bind Hdm2 in a manner that mimics Arf, and that may produce biological effects similar to those produced by Arf. Since many human cancers are characterized by Arf loss while p53 is maintained in wild-type form [Sherr, *Cancer Res.*, 60: 3689-95 (2000)], this methodology should have wide-ranging implications in the treatment of cancer in humans.

Furthermore, peptides (e.g., A1 and H1) derived from the binding domain of the tumor suppressor protein p14Arf, and the cellular oncoprotein Hdm2, self-assemble to form amyloid-like protofibrils comprised of anti-parallel β-strands. The interacting domains of the Arf and Hdm2 proteins are highly disordered in solution and do not self-assemble [DiGiammarino, E. L.; Filippov, L; Weber, J. D.; Bothner, B.; Kriwacki, R. W., *Biochem.* 40:2379±2386 (2001) and Bothner, B.; Lewis, W. S.; DiGiammarino, E. L.; Weber, J. D.; Bothner, S. J.; Kriwacki, R. W., *J. Mol. Biol.* 314:263-277 (2001)]. It is further disclosed that larger fragments of Arf and Hdm2, which encompass the A1 and H1 peptides, respectively, are shown to undergo a disorder-to-order transition upon binding in vitro and to self-assemble into β-strand-containing supramolecular structures. These structures, however, are less well ordered than the A1/H1 peptide co-assemblies. It is also disclosed that that the larger A1- and H1-containing protein fragments interact in situ, an observation which emphasizes the biological relevance of the coassembly and structural observations provided herein.

ABBREVIATIONS

BrdU 5-bromodeoxyuridine
CD circular dichroism
CHAPSO 3-[(3-Cholamidopropyl) dimethylammonio]-2-hydroxypropanesulfonic acid
DAPI 4'-6-Diamidino-2-phenylindole-2HCl
DMEM Dulbecco's modified Eagle's medium
EDC N-Ethyl-N'-(3-Dimethylaminopropyl)Carbodiimide
FBS fetal bovine serum
FMOC-amino acids α-(9-fluorenylmethyloxycarbonyl)-amino acid
GFP green fluorescent protein
HBS-N buffer 0.01 M HEPES, pH 7.4, 0.15 M NaCl
HBTU 2-(1H-Benzotriazole-1-yl)-1,1,3,3-tetramethyluronium-hexafluorophosphate
HEPES 4-(2-Hydroxyethyl)-1-Piperazineethanesulfonic Acid
HMP hydroxymethylphenyl-polystyrene resin
HOBt N-hydroxybenzotriazole
NHS N-Hydroxysuccinimide
NLS nuclear localization signal
NMR nuclear magnetic resonance
NoLS nucleolar localization signal
PBS phosphate-buffered saline
SDS-PAGE sodium dodecyl sulfate polyacrylamide gel electrophoresis
SPR surface plasmon resonance
TFA trifluoroacetic acid Therefore, if appearing herein, the following terms shall have the definitions set out below.

As used herein the terms "Arf", "ARF", "p19$^{ARF}$ protein," "p19$^{ARF}$", "ARF-p19", "ARF-p19/ARF-p14", "p 14$^{ARF}$ protein," "p14$^{ARF}$", or "ARF-p14" are all used interchangeably except that "p 14$^{ARF}$ protein", "p14$^{ARF}$", ", "ARF-p14" in general refer specifically to the human protein. Arf is involved in regulation of the eukaryotic cell cycle. The Arf protein is encoded by a nucleic acid derived from the gene locus, INK4A-Arf, which also encodes an inhibitor of D-type cyclin-dependent kinases termed "p16$^{INK4a}$ protein," "p16$^{InKa}$ or simply "InK4a-p16." [see also Quelle et al., *Cell*, 83:993-1000 (1995)]

An "active fragment" of an Arf protein is a peptide or polypeptide that comprises a fragment of Arf and retains at least one physiological activity of the Arf e.g. by acting as a tumor suppressor and/or having the ability to bind to Dm2. Examples of active fragments of Arf are the peptides encoded by exon 1B, e.g. amino acid residues 1-62 of SEQ ID NO:4 and the peptide encoded by amino acid residues 1-37 of SEQ ID NO:2. A fusion protein comprising an active fragment of an Arf protein can often be used interchangeably with an active fragment of an Arf protein, and such fusion proteins are meant to be included when the term. "active fragment" of an Arf protein is used.

As used herein a peptide "consisting of a minimal domain of Arf" is a peptide comprising the minimum portion of the full-length Arf that still retains the ability of the full-length Arf protein to bind Dm2 and act as a tumor repressor.

As used herein, an "inducing fragment" of an Arf protein is an active fragment of an Arf protein that can induce supramolecular assemblies and/or β-strand assembly of (i) DM2; and/or (ii) an inducible fragment of Dm2; and/or (iii) an Arf-Dm2 complex. Preferably an inducing fragment of Arf comprises two copies of the Arf motif each comprising the amino acid sequence of SEQ ID NO:13. A fusion protein comprising an inducing fragment of an Arf protein can often be used interchangeably with an inducing fragment of an Arf protein, and such fusion proteins are meant to be included when the term inducing fragment of an Arf protein is used.

As used herein the term "sufficient Arf activity" means activity sufficient to arrest the entry of cells into the cell division cycle, which is a hallmark of Arf activity. This activity has been characterized [Weber, et al., *Nat. Cell Biol.* 1:20-26 (2000); Weber, et al., *Mol. Cell. Biol.* 20:2517-2528 (2000) and U.S. application Ser. No. 09/480,718, filed Jan. 7, 2000, the contents of which are hereby incorporated by reference in their entireties]. Further, this activity has been characterized for a fragment of mouse p19$^{Arf}$ containing residues 1-37 [Di-Giammarino, et al., *Biochemistry* 40:2379-2386 (2001), the contents of which are hereby incorporated by reference in their entireties].

The abbreviation "DM2" or "Dm2" as used herein refers to the generic form of the protein "Mdm2" and its human ortholog "Hdm2." which are Murine Double Minute 2 and Human Double Minute 2 respectively. Hdm2 has the GenBank accession number of M92424, an amino acid sequence of SEQ ID NO:8 and a nucleic acid sequence of SEQ ID NO:7. Mdm2 has the GenBank accession number of X58876, an amino acid sequence of SEQ ID NO:6 and a nucleic acid sequence of SEQ ID NO:5. Mdm2, for example, can bind to the N-terminal transcriptional activation domain of p53 to block expression of p53-responsive genes [Momand et al., *Cell* 69:1237-1245 (1992); Oliner et al., *Nature* 362:857-860 (1993)], it has an intrinsic E3 ligase activity that conjugates ubiquitin to p53 [Honda and Yasuda, *Oncogene* 19:1473-1476 (2000)] and it also appears to play a role in shuttling p53 from the nucleus to the cytoplasm, where p53 is degraded in cytoplasmic proteasomes [Freedman and Levine, *Mol. Cell. Biol.* 18:7288-7293 (1998); Roth et al., *EMBO J.* 17:554-564 (1998); Tao and Levine, *Proc. Natl. Acad. Sci.* 96:3077-3080 (1999)].

As used herein a peptide "consisting of a minimal domain of Dm2" is a peptide comprising the minimum portion of the full-length Dm2 that still retains the ability to bind Arf and thereby competitively inhibit the binding of Arf with the full-length DM2.

As used herein, an "inducible fragment" of a Dm2 protein is a fragment of a Dm2 protein that can be induced to form supramolecular assemblies and/or β-strand assemblies by Arf, and/or an inducing fragment of Arf. An inducible fragment of Dm2 may be part of an Arf-Dm2 complex. Preferably an inducible fragment of Dm2 comprises the amino acid residues 235-259 of SEQ ID NO:8 and/or the amino acid residues 275-289 of SEQ ID NO:8. A fusion protein comprising an inducible fragment of a Dm2 protein can often be used interchangeably with an inducible fragment of a Dm2 protein, and such fusion proteins are meant to be included when the term an inducible fragment of a Dm2 protein is used.

As used herein the terms "fusion protein" and "fusion peptide" are used interchangeably and encompass "chimeric proteins and/or chimeric peptides". A fusion protein comprises at least a portion of one protein such as ARF-p19 joined via a peptide bond to at least another portion of a protein or peptide that it is not naturally contiguously connected to. For example, a fusion peptide of the present invention includes a peptide that consists of two consecutive nonamers and/or octamers each having the amino acid sequence of SEQ ID NO:13. In another embodiment, the fusion peptide can comprise amino acid residues of SEQ ID NO:11 or SEQ ID NO:26 covalently joined to a linker peptide which in turn is bound to amino acid residues of SEQ ID NO:12. Fusion proteins and peptides can also, and/or alternatively comprise a marker protein or peptide as exemplified below, or a protein or peptide that aids in the isolation and/or purification of the fusion protein.

A "heterologous nucleotide sequence" as used herein is a nucleotide sequence that is added to a nucleotide sequence of the present invention by recombinant methods to form a nucleic acid which is not naturally formed in nature. Such nucleic acids can encode fusion (e.g. chimeric) proteins. Thus the heterologous nucleotide sequence can encode peptides and/or proteins which contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

As used herein a "polypeptide" is used interchangeably with the term "protein" and denotes a polymer comprising two or more amino acids connected by peptide bonds. Preferably, a polypeptide is further distinguished from a "peptide" with a peptide comprising about twenty or less amino acids, and a polypeptide or protein comprising more than about twenty amino acids. Preferably a protein fragment is defined as a peptide or a polypeptide employing the same size criteria.

As used herein "supramolecular assemblies comprised of β-strands" describes peptides or polypeptides that bind together to form high molecular weight assemblies. In the present case, Arf and Dm2 bind together to form assemblies comprised of β-strands. These assemblies are comprised of many molecules of Arf and Dm2. The molecular size of these assemblies is characterized using, for example, gel filtration chromatography, wherein the assemblies elute at early times in the excluded volume and appear to have a molecular weight of 200 Kilodaltons, or greater.

As used herein a "small organic molecule" is an organic compound [or organic compound complexed with an inorganic compound (e.g., metal)] that has a molecular weight of less than 3 Kilodaltons, and preferably less than 1.5 Kilodaltons. A "compound" of the present invention is preferably a small organic molecule. Preferably, the small organic molecules identified by the methods of the present invention are not peptides.

As used herein the terms "solid substrate" and "solid support" are used interchangeably and represent a solid material that provides an inert surface that allows a biological reaction to be performed. Solid supports include biological chip plates as exemplified by Rava et al., U.S. Pat. No. 5,874,219, the contents of which are hereby incorporated by reference in their entireties and multi-well (multi-titer) quartz and polystyrene plates. Examples of material that can be used as solid substrates include glass, peptide polymers (e.g., collagen), peptoid polymers, polysaccharides (including commercial beads, e.g., SEPHADEX® (a cross linked dextran gel in bead form) and the like), carbohydrates, hydrophobic polymers, polymers, tissue culture polystyrene, metals, derivatized plastic films, glass beads, plastic beads, alumina gels, magnetic beads, nitrocellulose, cellulose, and nylon membranes.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host, i.e., a shrinkage of a tumor.

As used herein, the term "ortholog" refers to the relationship between proteins that have a common evolutionary origin and differ because they originate from different species or strains. For example, mouse ARF p19 is an ortholog of human ARF-p14.

As used herein an amino acid sequence is 100% "homologous" to a second amino acid sequence if the two amino acid sequences are identical, and/or differ only by neutral or conservative substitutions as defined below. Accordingly, an amino acid sequence is 50% "homologous" to a second amino acid sequence if 50% of the two amino acid sequences are identical, and/or differ only by neutral or conservative substitutions.

As used herein, DNA and protein sequence percent identity can be determined using MacVector 6.0.1, Oxford Molecular Group PLC (1996) and the Clustal W algorithm with the alignment default parameters, and default parameters for identity. These commercially available programs can also be used to determine sequence similarity using the same or analogous default parameters.

Polypeptides, peptides, or protein fragments of the present invention include, but are not limited to, those containing part of the amino acid sequences of an Arf protein and/or a Dm2 protein, including altered sequences in which functionally equivalent amino acid residues are substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

As used herein the term "approximately" is used interchangeably with the term "about" and signifies that a value is within twenty percent of the indicated value i.e., a protein containing "approximately" 50 amino acid residues can contain between 40 and 60 amino acid residues.

Candidate Compounds

A candidate compound can be obtained by a number of means, including from a commercially available chemical library or an "in house" pharmaceutical library. Examples of libraries of compounds that are commercially available include the Available Chemicals Directory (ACD), the Specs and BioSpecs database, the Maybridge database, and the Chembridge database. Examples of pharmaceutical companies with "in house" chemical libraries include Merck, GlaxoSmithKline, Bristol Myers Squibb, Eli Lilly, Novartis, and Pharmacia.

Alternatively, candidate compounds can also be synthesized de novo either individually or as combinatorial libraries [Gordon et al., *J. Med. Chem.* 37:1385-1401 (1994)]. They may also be obtained from phage libraries. Phage libraries have been constructed which when infected into host *E. coli* produce random peptide sequences of approximately 10 to 15 amino acids [Parmley and Smith, *Gene* 73:305-318 (1988); Scott and Smith, *Science* 249:386-390 (1990)]. Once a phage encoding a peptide that can act as a potential drug has been purified, the sequence of the peptide contained within the phage can be determined by standard DNA sequencing techniques. Once the DNA sequence is known, synthetic peptides can be generated which are encoded by these sequences.

Since the present invention discloses the critical portions of the mutual binding domains of Arf and Dm2, the bound Arf-Dm2 peptide binding complex can be readily analyzed to determine their three-dimensional structure. Using this structural information, potential mimics for the Arf peptides or inhibitors of the Arf-Dm2 binding can be examined through the use of computer modeling using a docking program such as DOCK, GRAM, or AUTODOCK [Dunbrack et al., *Folding & Design*, 2:27-42 (1997)]. This procedure can include computer fitting of candidate compounds to Dm2 for example, to determine how well the shape and the chemical structure of the candidate compound can bind to the Dm2 fragment [Bugg et al., *Scientific American*, Dec.:92-98 (1993); West et al., *TIPS* 16:67-74 (1995)]. Computer programs can also be employed to estimate the attraction, repulsion, and steric hindrance of the Arf or Dm2 peptides with a candidate compound.

Generally, the greater the steric complementarity and the greater the attractive forces, the more potent the candidate compound since these properties are consistent with a tighter binding constant. Furthermore, the more specificity in the design of a candidate compound, the more likely that the resulting drug will not interact as well with other proteins. This will minimize potential side-effects due to unwanted interactions with other proteins.

Systematic modification of selected compounds by computer modeling programs can then be performed until one or more compounds are identified. Such analysis has been shown to be effective in the development of HIV protease inhibitors [Lam et al., *Science* 263:380-384 (1994); Wlodawer et al., *Ann. Rev. Biochem.* 62:543-585 (1993); Appelt, *Perspectives in Drug Discovery and Design* 1:23-48 (1993); Erickson, *Perspectives in Drug Discovery and Design* 1:109-128 (1993)].

In another such example, Selzer et al. [*Exp. Parasitol.* 87(3):212-221 (1997)] screened the Available Chemicals Directory (a database of about 150,000 commercially available compounds) for potential cysteine protease inhibitors, using DOCK3.5. Based on both steric and force field considerations, they selected 69 compounds. Of these, three had IC50's below 50 µM (i.e., the concentration of the compound required to inhibit the reaction rate by 50%).

In addition, amino acid analogs, or peptidomimetics can be used that employ one or more unnatural or synthetic amino acids, such as using a D amino acid. The subunits may be linked by peptide bonds or by other the bonds, e.g., an ester, ether, etc. A good starting point for designing such a peptidomimetic is of course a peptide of the present invention, e.g., one comprising the amino acid sequence of SEQ ID NO:13.

Synthetic peptides prepared using the well known techniques of solid phase, liquid phase, or peptide condensation techniques, or any combination thereof, can thus include natural and unnatural amino acids. Amino acids used for peptide synthesis may be standard Boc (N-amino protected N-t-butyloxycarbonyl) amino acid resin with the standard deprotecting, neutralization, coupling and wash protocols of the original solid phase procedure of Merrifield [*J. Am. Chem. Soc.* 85:2149-2154 (1963)], or the base-labile N-amino protected 9-fluorenylmethoxycarbonyl (Fmoc) amino acids first described by Carpino and Han [*J. Org. Chem.* 37:3403-3409 (1972)]. Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other N-protecting groups that are familiar to those skilled in this art. Solid phase peptide synthesis may be accomplished by techniques familiar to those in the art and provided, [for example, in Stewart and Young *Solid Phase Synthesis*, Second Edition, Pierce Chemical Co., Rockford, Ill. (1984); and Fields and Noble, *Int. J. Pept. Protein Res.* 35:161-214 (1990)], or using automated synthesizers, such as sold by ABS. Thus, polypeptides of the invention may comprise D-amino acids, a combination of D- and L-amino acids, and various "designer" amino acids (e.g., β-methyl amino acids, C α-methyl amino acids, and N-α-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

In one aspect of the invention, the peptides may comprise a special amino acid at the C-terminus which incorporates either a $CO_2H$ or $CONH_2$ side chain to simulate a free glycine or a glycine-amide group. Another way to consider this special residue would be as a D or L amino acid analog with a side chain consisting of the linker or bond to the bead. In one embodiment, the pseudo-free C-terminal residue may be of the D or the L optical configuration; in another embodiment, a racemic mixture of D and L-isomers may be used.

In any case, compounds can be selected, for example, for their ability to induce β-strand formation of the Hdm2 fragments disclosed herein. A "lead" compound can then be identified for use as a focus of a drug development project.

Methods of Identifying Compounds that Affect the Arf-Dm2 Interaction

As disclosed by the present invention, new β-strand secondary structure forms when Arf and Hdm2 interact. This β-strand secondary structure is due to the interaction of small, specific domains present in Arf (e.g., the Arf motif having the amino acid sequence of SEQ ID NO:13) and Dm2 (e.g., H1 and H2 fragments as defined in the example below). In addition, as disclosed herein, the binding of Arf and Dm2 does not lead to a bimolecular complex as expected, but rather involves large, extended structures with predominantly β-strand secondary structure, i.e., supramolecular assemblies comprised of β-strands. Therefore, measuring the formation of this β-strand secondary structure directly or indirectly via measurement of Arf-Dm2 binding provides the unique ability to select specific compounds based on their capacity to either mimic the effect of Arf on Dm2, or alternatively to interfere with the Arf-Hdm2 binding complex and associated β-strand formation. As detailed below, such measurements can be performed with NMR spectroscopy, circular dichroism spectropolarimetry, Fourier Transform Infra-Red spectroscopy (FT-IR), fluorescence spectroscopy, or surface plasmon resonance. In addition, determining the size of the resulting protein-protein, or peptide-peptide complex, can also be used to select such specific compounds. In this case, any size distinguishing methodology such as gel filtration chromatography, gel electrophoresis, ultra centrifugation, dynamic light scattering etc. may be used.

Thus, as detailed below, gel filtration chromatography demonstrated that mArfN37 and Hdm2 210-304 elute together in the void volume, whereas the uncomplexed peptides elute at times consistent with monodisperse, conformationally extended polypeptides. Similarly, NMR resonances for $^{15}$N-mArfN37 or $^{15}$N-Hdm2 210-304 (and $^{15}$N-Hdm2 210-275) are broadened beyond detection when an unlabeled form of the appropriate binding partner is added to the solution. Furthermore, the NMR spectra are consistent with slow exchange between the free and bound states. In addition, at mArfN37:Hdm2 210-304 molar ratios that produce maximal β-strand secondary structure based on ellipticity at 200 nm using CD resonances cannot be observed for the isotope-labeled component of Arf/Hdm2 mixtures.

Dm2 or Dm2 peptides comprising one or more specific interacting domains, such as Hdm2 210-275 and 210-304, exemplified below, can be labeled with $^{15}$N. NMR spectra can be performed and $^1$H-$^{15}$N steady-state {$^1$H}-$^{15}$N nuclear Overhauser effect (NOE) values can be determined as the ratio of peak intensities in 2D $^1$H-$^{15}$N correlation spectra with and without $^1$H saturation. Alternatively, or in addition, a circular dichroism spectropolarimeter, as exemplified below, can be used to monitor the structural changes. Such measurements can be performed in the presence and absence of test compounds to determine the effect of the compound on the formation of β-strand secondary structure in the H1 and H2 domains, for example. In one embodiment, the assay is performed in the absence of Arf and Arf fragments, and a compound is selected which can stimulate the formation of β-strand secondary structure of Dm2 (fragment thereof) and/or the formation of supramolecular assemblies. In another embodiment, the assay is performed in the presence of Arf and/or an Arf fragment, and a compound is selected that can enhance the rate of formation of β-strand secondary structure of Dm2 (or fragment thereof) and/or the formation of supramolecular assemblies. In still another embodiment, a compound is selected that interferes with and/or inhibits the rate of formation of β-strand secondary structure of Dm2 (fragment thereof) and/or the formation of supramolecular assemblies in the presence of Arf and/or an Arf fragment.

The measurements outlined above can be preceded or alternatively followed by other determinations. Thus, compounds can be initially selected for their ability to bind specific Dm2 peptides (such as those comprising H1 and H2 as defined in the Example below) or Arf peptides (such as those comprising the amino acid sequence of SEQ ID NO:13). Alternatively, compounds can be selected for their ability to interfere with the binding of Arf with Dm2 (using either the full-length proteins or fragments, including peptides that comprise the Arf and Dm2 binding domains as defined in the Example below). As exemplified below, such binding studies can be performed using Surface Plasmon Resonance (SPR).

Thus, initial screens can be performed in a high throughput format using any of a large number of methodologies. One such method employs a solid support that comprises multiple compartments (e.g., wells). Currently a solid support comprising between 96 and 1516 compartments is relatively standard in drug assays. Each compartment can include a separate reaction mixture. In a particular embodiment, a selected target molecule (e.g., an Arf peptide) can be introduced into the compartments either in solution or on a solid support such as a chip [see U.S. Pat. No. 5,874,219, Issued Feb. 23, 1999, the contents of which are hereby incorporated by reference in their entireties]. The remaining components of the reaction mixture can be added to the compartment and a compound can then be added to determine if the compound binds to the peptide, using radioactive compounds for example and a wash step.

If a chip is employed, a chip reader is generally used to measure the reaction. Accordingly, the compartments in which the detectable signal appears can be readily identified. The interaction between reactants can be characterized in a number of ways including in terms of kinetics and/or thermodynamics.

Assays on biological arrays generally include carrying out the particular binding reaction under selected conditions, optionally washing the compartment to remove unreacted molecules, and analyzing the biological array for evidence of binding between the reactants. Since the process can involve multiple steps, it is preferred that such steps be automated so as to allow multiple assays to be performed concurrently. Accordingly high throughput analysis can employ automated fluid handling systems for concurrently performing the reaction steps in each of the compartments. Fluid handling allows uniform treatment of samples in the compartments. Microtiter robotic and fluid-handling devices are commercially available, including from Tecan AG.

A fluid handling device can be used to manipulate the reaction conditions in any given compartment by, for example, (i) adding or removing fluid from the compartments, including for manipulating the concentration of the reactants; (ii) maintaining and/or manipulating the temperature of the liquid in the compartment; (iii) altering the ionic strength of the reaction mixture; and (iv) agitating the compartments to ensure proper mixing. A reader can then be used to measure the reaction and a computer with an appropriate program can further analyze the results from the reaction [see U.S. Pat. No. 5,874,219, Issued Feb. 23, 1999, the contents of which are hereby incorporated by reference in their entireties]. Data analysis can include removing "outliers" (data deviating from a predetermined statistical distribution), and calculating the relative reaction activity of each compartment. In a particular embodiment, the resulting data are displayed as an image with color in each region varying according to the amount of detectable binding measured.

A solid support can be introduced into a holder in the fluid-handling device. Preferably the fluid-handling device is a robotic device that is programmed to: (i) set appropriate reaction conditions, such as temperature, and volumes; (ii) to add specific reactants to the compartments; (iii) incubate the binding partners for an appropriate time; (iv) remove unreacted reactants; (v) wash the compartments; (vi) add reactants/test compounds as appropriate to the compartments; and (viii) allow the detection of the reaction.

As part of the binding studies performed herein, it is often desiresable to label one or more of the reagents. Suitable labels include enzymes as discussed above, fluorophores (e.g., fluorescein isothiocyanate (FITC), phycoerythrin (PE), Texas red (TR) rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents.

In the instance where a radioactive label, such as the isotopes 3H, $^{14}C$, $^{32}P$, $^{35}S$, $^{36}Cl$, $^{51}Cr$, $^{57}Co$, $^{58}CO_3$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized techniques known in the art including ultraviolet, visible, and infra-red spectroscopy, circular dichroism, magnetic circular dichroism, fluorescence (including measuring changes in fluorescent lifetimes and fluorescent anisotropy), bioluminescence, luminescence, phosphorescence, mass spectrometry, NMR, ESR, amperometric or gasometric techniques.

Direct labels are one example of labels that can be used according to the present invention. A direct label has been defined as an entity which in its natural state is readily visible, either to the naked eye or with the aid of an optical filter and/or applied stimulation, e.g. ultraviolet light to promote fluorescence. Examples of colored labels that can be used according to the present invention include metallic sol particles, for example, gold sol particles such as those described by Leuvering (U.S. Pat. No. 4,313,734); dye sol particles such as described by Gribnau et al. (U.S. Pat. No. 4,373,932) and May et al. (WO 88/08534); dyed latex such as described by May, Supra, Snyder (EP-A 0 280 559 and 0 281327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, and urease. These and others have been discussed in detail by Eva Engvall in Enzyme Immunoassay ELISA and EMIT in *Methods in Enzymology*, 70:419-439 (1980) and in U.S. Pat. No. 4,857, 453. The protein/peptides of the present invention can be modified to contain a marker protein such as luciferase or green fluorescent protein as described in U.S. Pat. No. 5,625, 048 filed Apr. 29, 1997, WO 97/26333, published Jul. 24, 1997 and WO 99/64592, published Dec. 16, 1999, all of which are hereby incorporated by reference in their entireties.

Suitable marker enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}$P, e.g., as described in European Patent No. 0372707 (application No. 89311108.8) by Sidney Pestka, or U.S. Pat. No. 5,459, 240, issued Oct. 17, 1995 to Foxwell et al.

Polypeptides, and peptides, including antibodies, can be labeled by metabolic labeling. Metabolic labeling occurs during in vitro incubation of the cells that express the protein in the presence of culture medium supplemented with a metabolic label, such as [$^{35}$S]-methionine or [$^{32}$P]-orthophosphate. In addition to metabolic (or biosynthetic) labeling with [$^{35}$S]-methionine, the invention further contemplates labeling with [$^{15}$N]-amino acids, [$^{14}$C]-amino acids and [$^{3}$H]-amino acids (with the tritium substituted at non-labile positions).

Once a lead compound is identified it can be tested for its ability to affect one or more of the activities attributed to Arf, including to induce β-strand assembly of Dm2 (e.g., Hdm2 or Mdm2) or a fragment thereof. For example, its ability to bind Mdm2, to inhibit Mdm2-dependent nucleo-cytoplasmic shuttling of p53, to inhibit the E3 ubiquitin ligase activity of Mdm2 toward p53 in vitro and/or its ability to sequester Mdm2 in the nucleolus can be determined. Such effects can be measured in Arf$^{-/-}$ cells such as NIH 3T3 cells in which Mdm2 is present, for example. Alternatively, microinjection and live cell imaging, as exemplified below can be used to determine whether Hdm2, for example, is sequestered within nucleoli by a particular compound.

As detailed below, Hdm2 deletion constructs tagged with a fluorescent label TEXAS RED® ($C_{31}H_{29}S_2N_2O_6Cl_1$) were microinjected into the nucleus of NIH 3T3 cells that lack the gene for Arf. Nuclear microinjection was used because the Hdm2 constructs containing the central Arf-binding domain lack the nuclear localization signal found between residues 181-186.

Thus labeled Hdm2 constructs can be individually injected into cells in the absence or presence of the compound and the localization of the labeled Hdm2 in the nucleoplasm and nucleoli can be determined. If the labeled Hdm2 is sequestered within nucleoli in the presence of the compound relative to in its absence, the compound is identified as an Arf mimic. Analogously, if the compound interferes with Hdm2 being sequestered in the nucleoli, when Arf is present, the compound is identified as an inhibitor of the Arf-Hdm2 interaction. Next, a lead compound can be tested in animal models to determine its effect on tumors for example, and then finally, tested in humans.

Furthermore, the effect of a lead compound on cell division can be determined by monitoring the incorporation of BrdU into chromosomal DNA in NIH 3T3 cells, as previously described [DiGiammarino, et al., *Biochemistry* 40:2379-2386 (2001), the contents of which are hereby incorporated by reference in their entireties]. NIH 3T3 cells, for example, can be cultured in the presence or absence of a lead compound and, after a set time interval, such as 8 hours, the amount of BrdU incorporated into chromosomal DNA can be determined using immunofluorescence microscopy. A lead compound is then selected (identified) when the amount of BrdU incorporated in the presence of the compound decreases relative to the amount incorporated in the absence of the compound.

Antibodies to the Arf and DM2 Peptides of the Present Invention

The Arf and Dm2 polypeptides and peptides of the present invention, as produced by a recombinant source or through chemical synthesis, or isolated from natural sources, or from a digestion of a recombinant/natural polypeptide, and derivatives or analogs thereof, including fusion proteins, may be used as an immunogen to generate antibodies that recognize the corresponding peptide. Such antibodies include but are not limited to polyclonal, monoclonal, chimeric including humanized chimeric, single chain, Fab fragments, and a Fab expression library. Polyclonal antibodies have greater likelihood of cross reactivity.

Thus the present invention provides compositions and uses of antibodies that are immunoreactive with the Arf and Dm2 peptides of the present invention. Such antibodies "bind specifically" to such peptides, meaning that they bind via antigen-binding sites of the antibody as compared to non-specific binding interactions. The terms "antibody" and "antibodies" are used herein in their broadest sense, including but not limited to intact monoclonal and polyclonal antibodies as well as fragments such as Fv, Fab, and F(ab')2 fragments, single-chain antibodies such as scFv, and various chain combinations. In some embodiments, the antibodies of the present invention are humanized antibodies or human antibodies. The antibodies may be prepared using a variety of well-known methods including but not limited to immunization of animals having native or transgenic immune repertoires, phage display, hybridoma and recombinant cell culture, and transgenic plant and animal bioreactors.

Both polyclonal and monoclonal antibodies may be prepared by conventional techniques. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Various procedures known in the art may be used for the production of polyclonal antibodies to the Arf and Dm2 peptides of the present invention or derivatives or analogs thereof. For the production of antibody, various host animals can be immunized by injection with such a peptide, or a derivative (e.g., or fusion protein) thereof, including but not limited to rabbits, mice, rats, sheep, goats, etc. In one embodiment, the peptide can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the Arf and Dm2 peptides of the present invention, or analogs, or derivatives thereof, any technique that provides for the production of antibody molecules by continuous cell lines in culture may be used. These include but are not limited to the hybridoma technique originally developed by Kohler and Milstein [*Nature*, 256:495-497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals utilizing recent technology [PCT/US90/02545].

The monoclonal antibodies of the present invention include chimeric antibodies, e.g., "humanized" versions of antibodies originally produced in mice or other non-human species. Such humanized antibodies may be prepared by known techniques and offer the advantage of reduced immunogenicity when the antibodies are administered to humans. In fact, according to the invention, techniques developed for the production of "chimeric antibodies" [Morrison et al., *J. Bacteriol.*, 159:870 (1984); Neuberger et al., *Nature*, 312: 604-608 (1984); Takeda et al., *Nature*, 314:452-454 (1985)] by splicing the genes from a mouse antibody molecule specific for an Arf and/or Dm2 peptide of the present invention together with genes from a human antibody molecule of appropriate biological activity can be used. Antibodies such as these are within the scope of this invention.

Thus, a humanized antibody is an engineered antibody that typically comprises the variable region of a non-human (e.g., murine) antibody, or at least complementarity determining regions (CDRs) thereof, and the remaining immunoglobulin portions derived from a human antibody. Procedures for the production of chimeric and further engineered monoclonal antibodies include those described Riechmann et al., [*Nature* 332:323, (1988)]; Liu et al., [*Proc. Nat. Acad. Sci.* 84:3439 (1987)]; Larrick et al., [*Bio/Technology* 7:934, (1989)]; and Winter and Harris, [*TIBS* 14:139, (May, 1993)]. Such human or humanized chimeric antibodies are preferred for use in therapy of human diseases or disorders (described infra), since the human or humanized antibodies are much less likely than xenogenic antibodies to induce an immune response, in particular an allergic response, themselves.

Therefore, procedures that have been developed for generating human antibodies in non-human animals may be employed in producing antibodies of the present invention. The antibodies may be partially human or preferably completely human. For example, transgenic mice into which genetic material encoding one or more human immunoglobulin chains has been introduced may be employed. Such mice may be genetically altered in a variety of ways. The genetic manipulation may result in human immunoglobulin polypeptide chains replacing endogenous immunoglobulin chains in at least some, and preferably virtually all, antibodies produced by the animal upon immunization. Mice in which one or more endogenous immunoglobulin genes have been inactivated by various means have been prepared. Human immunoglobulin genes have been introduced into the mice to replace the inactivated mouse genes. Antibodies produced in the animals incorporate human immunoglobulin polypeptide chains encoded by the human genetic material introduced into the animal. Examples of techniques for the production and use of such transgenic animals to make antibodies (which are sometimes called "transgenic antibodies") are described in U.S. Pat. Nos. 5,814,318, 5,569,825, and 5,545,806, which are incorporated by reference herein.

Hybridoma cell lines that produce monoclonal antibodies specific for the polypeptides of the invention are also provided by the present invention. Such hybridomas may be produced and identified by conventional techniques. One method for producing such a hybridoma cell line comprises immunizing an animal with a polypeptide, harvesting spleen cells from the immunized animal, fusing said spleen cells to a myeloma cell line, thereby generating hybridoma cells, and identifying a hybridoma cell line that produces a monoclonal antibody that binds the polypeptide. The monoclonal antibodies produced by hybridomas may be recovered by conventional techniques.

According to the invention, techniques described for the production of single chain antibodies [U.S. Pat. Nos. 5,476, 786 and 5,132,405 to Huston; U.S. Pat. No. 4,946,778] can be adapted to produce e.g., Arf peptide-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for an Arf peptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. Antibody binding can be detected by detecting a label on the primary antibody, or by detecting binding of a secondary antibody or reagent to the primary antibody. In an alternative embodiment, the secondary antibody is labeled. Many means are known in the art for detecting binding in an immunoassay and are within the scope of the present invention. For example, to select antibodies which recognize a specific epitope of Arf, one may assay generated hybridomas for a product which binds to the Arf fragment containing such epitope and choose those which do not cross-react with the full-length Arf protein.

In a specific embodiment, antibodies that agonize or antagonize the binding of Arf to Hdm2 can be generated. Such antibodies can be tested using the assays described infra. In addition an antibody that mimics the effect of Arf on Hdm2 can also be assayed for using the assays disclosed herein.

Administration of the Therapeutic Compositions of the Present Invention

According to the present invention, the component or components of a therapeutic composition of the invention may be introduced topically, parenterally, transmucosally, e.g., orally, nasally, or rectally, or transdermally. When the administration is parenteral, it may be via intravenous injection, and also including, but is not limited to, intra-arteriole, intramuscular, intradermal, subcutaneous, intraperitoneal, intraventricular, and intracranial administration.

In a particular embodiment, the therapeutic compound can be delivered in a vesicle, in particular a liposome [see Langer, Science 249:1527-1533 (1990); Treat et al., in *Liposomes in the Therapy of Infectious Disease and Cancer*, Lopez-Berestein and Fidler (eds.), Liss: New York, pp. 353-365 (1989); Lopez-Berestein, ibid, pp. 317-327; see generally ibid.].

In yet another embodiment, the therapeutic compound can be delivered in a controlled release system. For example, a small organic molecule as described above, may be administered using intravenous infusion, an implantable osmotic pump, a transdermal patch, liposomes, or other modes of administration. In one embodiment, a pump may be used [see Langer, supra; Sefton, *CRC Crit. Ref Biomed Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of a therapeutic target, thus requiring only a fraction of the systemic dose [see, e.g., Goodson, in *Medical Applications of Controlled Release*, supra, vol. 2, pp. 115-138 (1984)].

Other controlled release systems are discussed in the review by Langer [*Science* 249:1527-1533 (1990)].

Thus, a therapeutic composition of the present invention can be delivered by intravenous, intraarterial, intraperitoneal, intramuscular, or subcutaneous routes of administration. Alternatively, the therapeutic composition, properly formulated, can be administered by nasal or oral administration. A constant supply of the therapeutic composition can be ensured by providing a therapeutically effective dose (i.e., a dose effective to induce metabolic changes in a subject) at the necessary intervals, e.g., daily, every 12 hours, etc. These parameters will depend on the severity of the condition being treated, other actions, such as diet modification, that are implemented, the weight, age, and sex of the subject, and other criteria, which can be readily determined according to standard good medical practice by those of skill in the art.

A subject in whom administration of the therapeutic composition is an effective therapeutic regiment for cancer treatment for example, is preferably a human, but can be any primate, other mammals or even avians suffering from cancer, including domestic animals such as dogs and cats, laboratory animals such as rats, rabbits and mice, livestock, such as cattle (including cows), pigs, horses, and goats, and animals maintained in a zoo such as elephants, lions, zebras, and gorillas. Thus, as can be readily appreciated by one of ordinary skill in the art, the methods and pharmaceutical compositions of the present invention are particularly suited to administration to a number of animal subjects, but particularly humans.

Kits

The materials for use in this aspect of the invention are ideally suited for the preparation of a kit. Specifically, the invention provides a compartmentalized kit to receive in close confinement, one or more containers which comprise one or more of the peptides of the present invention; and optionally one or more other containers comprising reagents, such as additional buffers etc.

In detail, a compartmentalized kit includes any kit in which reagents are contained in separate containers. Such containers include small glass containers, plastic containers or strips of plastic or paper. Such containers allow one to efficiently transfer reagents from one compartment to another compartment such that the samples and reagents are not cross-contaminated and the agents or solutions of each container can be added in a quantitative fashion from one compartment to another. Such containers will include a container which will accept the test sample, a container which contains the peptides used in the assay, and containers which contain additional reagents such as specific buffers with defined ionic strengths.

The present invention may be better understood by reference to the following non-limiting Example, which is provided as exemplary of the invention. This example is presented in order to more fully illustrate the preferred embodiments of the invention. It should in no way be construed, however, as limiting the broad scope of the invention.

Example

Defining the Molecular Basis of Arf and Hdm2 Interactions

Introduction

Understanding the interaction of Arf and Hdm2 has recently become a central issue in cancer biology. In response to hyperproliferative signals, p14$^{Arf}$ stabilizes p53 by binding to Hdm2 and inhibits the ubiquitination and subsequent proteosome-dependent degradation of p53. The medical importance of the Arf-Hdm2-p53 regulatory system is highlighted by the finding that either p53 or p14$^{Arf}$ are lost or modified in virtually all human cancers.

5. Human and mouse Arf are highly basic proteins (~20% Arg residues) of 132 and 169 residues, respectively, that localize to nucleoli. The extreme N-terminal segments of the two proteins are very similar (17/29 identity; 21/29 similarity) and contain a repeated motif of 8 or 9 residues that comprises hydrophobic residues flanked by Arg residues [DiGiammarino et al., *Biochem.*, 40:2379-2386 (2001)]. Exon 1β of the human and mouse p16$^{Ink4a}$/Arf locus uniquely encodes the first 62 and 63 amino acids of human and mouse Arf, respectively, while exon 2 encodes the C-terminal domains. An alternative reading frame within exon 2 also encodes the central segment of p16$^{Ink4a}$ [Quelle et al., *Cell*, 83:993-1000 (1995)]. Importantly, peptides containing highly conserved N-terminal residues of human or mouse Arf have been shown to possess biological activity [Midgley et al., *Oncogene*, 19:2312-23 (2000); Weber et al., *Mol. Cell. Biol.*, 20:2517-2528 (2000); DiGiammarino et al., *Biochem.*, 40:2379-2386 (2001)]. For example, a peptide containing the N-terminal 37 amino acids of mouse Arf (termed mArfN37) localizes to nucleoli, binds and sequesters Hdm2 within nucleoli, and activates p53 leading to cell cycle arrest [Weber et al., *Mol. Cell. Biol.*, 20:2517-2528 (2000); DiGiammarino et al., *Biochem.*, 40:2379-2386 (2001)]. Additionally, a 20 amino acid peptide from the human Arf N-terminus inhibits Mdm2-dependent ubiquitination of p53 and activates p53 in vivo [Midgley et al., *Oncogene*, 19:2312-23 (2000)]. Further study of the Arf N-terminus has shown that the two repeated motifs within mArfN37 bind individually to Hdm2 and are both required for normal Arf function [Weber et al., *Mol. Cell. Biol.*, 20:2517-2528 (2000)]. Two segments of p14$^{Arf}$ also are reported to mediate interactions with Hdm2 but one of these is found in a different region of the polypeptide; these are residues 1-14 and 82-101 [Weber et al., *Mol. Cell. Biol.*, 20:2517-2528 (2000); Zhang et al., *Mol. Cell*, 3:579-91

(1999)]. Nucleolar localization of mouse and human Arf is specified by the amino acid sequence RRPR (SEQ ID NO:14) (the nucleolar localization signal, NoLS); the NoLS in p19$^{Arf}$ is found between residues 31-34 of SEQ ID NO:2 and in p14$^{Arf}$ between residues 87-90 of SEQ ID NO:4. Interestingly, when Arf binds Mdm2 (or Hdm2), the Arf NoLS is masked and nucleolar colocalization of the Arf/Mdm2 complex relies on the exposure of a cryptic NoLS within the RING domain of Mdm2 [Lohrum et al., Nat. Cell Biol., 2:179-81 (2000); Weber et al., Mol. Cell. Biol., 20:2517-2528 (2000)]. Despite the wealth of information on how Arf functions in cells, detailed information on the Hdm2-bound state of mArfN37, or the mechanism of Hdm2 binding or nucleolar localization is completely lacking.

Mdm2 is a multifunctional protein that is reported to interact with p53 [Wu et al., Genes Dev., 7:1126-1132 (1993)], CBP/p300 [Grossman et al., Mol Cell, 2:405-15 (1998)], E2F1 [Martin et al., Nature, 375:691-4 (1995); O'Connor et al., Embo J, 14:6184-92 (1995)], Rb [Xiao et al., Nature, 375:694-8 (1995)], L5 [Marechal et al., Mol Cell Biol, 14:7414-20 (1994)], TBP [Leveillard et al., Mech Dev, 74:189-93 (1998)] and Arf [Weber et al., Nat. Cell Biol., 1:20-26 (1999); Weber et al., Mol. Cell. Biol., 20:2517-2528 (2000); DiGiammarino et al., Biochem., 40:2379-2386 (2001)]. The human (Hdm2) and mouse (Mdm2) orthologs are 72% identical and can functionally substitute for one another. The domains responsible for some of the above interactions are well characterized. For example, the N-terminal domain of ~100 amino acids adopts a globular, helical structure and binds a small peptide within the p53 N-terminus; this interaction inhibits the transcriptional activation function of p53 [Kussie et al., Science, 274:948-953 (1996); Oliner et al., Nature, 362:857-860 (1993); Momand et al., Cell, 69:1237-1245 (1992)]. Two zinc-binding motifs have been identified in Mdm2, a $C_4$ zinc finger motif (amino acid residues 305-325 of SEQ ID NO:6) and a $C_3HC_4$ RING domain (amino aid residues 438-478 of SEQ ID NO:6) [Boddy et al., Trends Biochem Sci, 19:198-9 (1994)]. The latter domain has been shown to mediate ubiquitin ligase activity toward p53 in vitro [Honda et al., FEBS Lett, 420:25-7 (1997); Honda et al., Embo J, 18:22-7 (1999)] and to bind RNA [Elenbaas et al., Mol. Med., 2:439-51 (1996); Lai et al., Biochem., 37:17005-15 (1998)]. Further, the RING domain has been shown to bind zinc ions and to exhibit globular but disordered structure [Lai et al., Biochem., 37:17005-15 (1998)]. The $C_4$ zinc finger motif has not been functionally characterized. The Arf-binding domain of Hdm2 has been mapped to amino acids 210-304 of SEQ ID NO:8 (termed Hdm2 210-304) [Weber et al., Mol. Cell. Biol., 20:2517-2528 (2000)]. The L5 binding domain also maps to this region [Marechal et al., Mol Cell Biol, 14:7414-20 (1994)]. Between humans and mice, this segment is 92% similar and, in striking contrast to Arg-rich Arf, is highly acidic (for Hdm2, 32% Asp/Glu, predicted pI ~3.2; for Mdm2, 33% Asp/Glu; predicted pI ~3.5). This central segment has been shown to bind N-terminal fragments of mouse Arf, including 1-37, 1-14 and 26-37 [Weber et al., Mol. Cell. Biol., 20:2517-2528 (2000)]. Furthermore, a peptide composed of the first 20 amino acids of human p 14$^{Arf}$ has been shown to bind the central, acidic segment of Hdm2 and to inhibit Hdm2-dependent ubiquitination of p53 in vitro [Midgley et al., Oncogene, 19:2312-23 (2000)]. The interaction motif within Hdm2 has been mapped to residues 212-244 [Midgley et al., Oncogene, 19:2312-23 (2000)]. The studies summarized above contribute significantly to the understanding of the cellular functions of Arf and Hdm2 but provide little insight into the physical and structural basis for these functions, such as the binding of Arf to Hdm7, nucleolar colocalization, inhibition of Hdm2-dependent nucleo-cytoplasmic shuttling of p53, and E3 ubiquitin ligase activity toward p53.

Materials and Methods

Hdm2 and p19$^{Arf}$ protein purification. Fragments of Hdm2 corresponding to residues 210-275 and 210-304 of SEQ ID NO:8 (termed Hdm2 210-275 and Hdm2 210-304) were subcloned into the expression plasmid pET28a (Novagen) using standard methods; pET28a allows expression of polypeptides with a thrombin cleavable poly-His affinity purification tag. Following protein expression in E. coli BL21(DE3) (Novagen, Inc.), bacterial cells were harvested by centrifugation followed by resuspension in 20 mM Tris-HCl (pH 8.0) 500 mM NaCl at 4° C., and lysed by sonication. Urea was added to a final concentration of 6 M to the soluble fraction after centrifugation (20,000 g, 20 min.). Soluble, His-tagged proteins were purified using Ni$^{2+}$-affinity chromatography (Chelating-Sepharose, Amersham Pharmacia Biotech, Inc.) in the presence of 6 M urea using otherwise standard procedures (Novagen, Inc.). An N-terminal fragment of mouse p19$^{Arf}$ corresponding to residues 1-37 (mArfN37) was purified in a similar manner, as previously reported [DiGiammarino et al., Biochem., 40:2379-2386 (2001)]. His tag-cleaved mArfN37 was further purified using $C_4$ reverse-phase high-performance liquid chromatography (HPLC) ($C_4$ column; Vydac, Inc.) using a 0.1% trifluoroacetic acid (TFA)/acetonitrile buffer system. Lyophilized proteins were directly dissolved in the appropriate buffer for each experiment, as described below. Fractions containing Hdm2 proteins were dialyzed into 20 mM Tris-HCl (pH 8.0), 500 mM NaCl and treated with thrombin (Novagen) 1 U/mg protein at room temperature for 16 hours to cleave the His tag. Constructs were further purified using anion exchange chromatography (Q SEPHAROSE, Amersham Pharmacia Biotech, Inc.) using 20 mM Tris-HCl buffer, pH 7.0 with elution using a 50 mM-1.0 M NaCl gradient over 0.05 liters.

Peptide Synthesis. Peptides were synthesized using standard Methods by an Advanced Chemtech 396 synthesizer. The peptide amides were synthesized on HMP-amide resin (Applied Biosystems, Inc.) and the FMOC-amino acids were coupled using HOBt/HBTU chemistries. N-terminal acetylation was performed using acetic anhydride and HOBt. Peptides were cleaved from the resin in 91% TFA containing 2% phenol, 2% ethanedithiol and 5% thioanisole. The peptides were precipitated and washed twice with diethyl ether. Peptide concentrations for circular dichroism (CD) and surface plasmon resonance (SPR) were determined using quantitative amino acid analysis.

Surface Plasmon Resonance. Binding studies were performed using a Biacore 3000 surface plasmon resonance (SPR) instrument (Biacore, Inc.). A Tetra-His™ Antibody (Qiagen, Inc.; Cat. #34670) was covalently attached to a carboxymethylated gold surface (C-1 chip; Biacore, Inc.). The carboxymethyl groups on the surface were activated with N-ethyl-N'-(3-dimethylaminopropyl) carbodiimide (EDC) and N-hydroxysuccinimide (NHS) and the antibody was attached at pH 7.4 in 20 mM sodium phosphate buffer, 150 mM NaCl (PBS). Reactive sites remaining on the surface were blocked by reaction with ethanolamine. The His-tagged ligand was attached to the antibody by injecting a 5-10µ/ml solution of the ligand in 10 mM HEPES, 150 mM NaCl, pH 7.4 (HBS-N buffer, Biacore) at a flow rate of 10 µL/Min through the flow cell. A reference cell was prepared similarly except that no His-tagged ligand was added. Binding was measured by flowing the non-His-tagged analyte through the reference and ligand-containing flow cells in sequence. Prior to injection of ligands, the chip surfaces were equilibrated in HBS-N buffer. Changes in the SPR response due to solvent differences and the injection process were monitored by injection of HBS-N buffer alone. Regeneration of the chip surface to remove bound analyte and ligand was accomplished by two 100 μL injections of 10 mM glycine, pH 2.0 through both flow cells. Data reported is the difference in SPR signal between the flow cell containing analyte and the reference cell. Duplicate injections were made and the SPR response values reported are the average of these two injections.

NMR Spectroscopy. Uniformly $^{15}$N-labeled Hdm2 210-275 and 210-304 were prepared using standard procedures [Kriwacki et al., *Proc. Natl. Acad. Sci. USA*, 93:11504-11509 (1996)]. Samples were concentrated by ultra-filtration using a 3000 Da cutoff filter (Millipore Corp., Centricon 3) to 1-2 mM in 10 mM potassium phosphate buffer, pH 6.0, 5% $D_2O$ (vol:vol) and placed in 5 mm micro-cell NMR tubes (Shegimi, Inc.). All NMR spectra were acquired using a 600 MHz Varian Inova NMR spectrometer (Varian Associates, Inc.) fitted with a 5 mm triple resonance probe equipped with x, y, z axis pulsed magnetic field gradients. 2D $^1$H-$^{15}$N HSQC spectra [Muller, *J. Amer. Chem. Soc.*, 101:4481-4484 (1979); Bodenhausen and Ruben, D. J. *Chem. Phys. Lett.*, 69:185-189 (1980)] were acquired using standard procedures provided in the Varian Protein Pack pulse sequence library. $^1$H-$^{15}$N steady-state {$^1$H}-$^{15}$N nuclear Overhauser effect (NOE) values were determined as the ratio of peak intensities in 2D $^1$H-$^{15}$N correlation spectra with and without $^1$H saturation [Farrow et al., *Biochem.*, 33:5984-6003 (1994)].

Circular Dichroism. Spectra were recorded at 25° C. using an Aviv Model 62A DS circular dichroism spectropolarimeter (Aviv Instruments, Inc.) equipped with a thermoelectric temperature control unit. All samples were prepared in 10 mM Tris-HCl, pH 7.0 at 0.02-0.2 mM as determined by amino acid analysis. Spectra were recorded using 1 mm quartz cuvettes and reported spectra are the average of 10 scans over the range 195-260 nM in 1 nM steps. Melting experiments were recorded in 10 mm quartz cuvettes with active stirring. The signal at 216 nm (β strand minimum) was used to monitor structural changes and the signal was averaged over 15 sec. The sample temperature was increased in 1° C. steps.

Fluorescent labeling. Proteins for fluorescence microimaging studies were covalently modified using an amine-reactive, sulfosuccinimidyl ester of TEXAS RED® ($C_{31}H_{29}S_2N_2O_6Cl_1$) (Molecular Probes, Inc., Cat. #C-1171). In brief, purified Hdm2-derived proteins were dialyzed into 100 mM sodium bicarbonate buffer, pH 8.3 at 2-4 mg/ml. The Texas Red™ dye was dissolved in dimethylsulfoxide at 10 mg/ml. Protein and dye 3:1 (vol:vol) were reacted for 1 hour at room temperature followed by purification using size-exclusion chromatography (NAP 5 G-25 columns, Amersham Pharmacia Biotech, Inc.). Labeled protein bands migrated more slowly than unlabeled protein in SDS-polyacrylamide gels consistent with the covalent attachment of dye.

Cell culture and microinjection. NIH 3T3 Arf$^{-/-}$ cells passage 10-15 were cultured in Dulbecco's modified Eagle's medium (Dulbecco's modified Eagle's medium (DMEM); Gibco-Invitrogen, Inc.), 10% fetal bovine serum (FBS) at 37° C., 7% $CO_2$. 24 hours prior to transfection, cells were plated on 35 mm dishes coated with poly-D-Lysine (Mattek, Corp.) at a density of $3 \times 10^4$ cells per dish. Cells were transfected with a pcDNA plasmid (Invitrogen) containing the GFP-p19$^{ARF}$ fusion protein using Fugene-6 (Roche Molecular Biochemicals, Inc.) in media according to the protocol supplied by the manufacturer. Sixteen hours post-transfection, the transfection media was refreshed with DMEM, 10% FBS and the cells were allowed to recover for four hours. GFP-Arf positive cells were then located and co-injected with TEXAS RED® ($C_{31}H_{29}S_2N_2O_6C_1$) labeled Hdm2 polypeptides (2 mg/ml in 20 mM Tris-HCl, 100 mM NaCl, pH 7.0) using a Micromanipulator 5171/Transjector 5246 (Eppendorf, AG) in media supplemented with 10 mM HEPES, pH 7.2 to buffer cell media during injection and imaging. Representative cells were imaged over time. An Axiovert 135 TV inverted fluorescence microscope with an automated stage controller (Carl Zeiss, Inc.) and circulating water bath heater (Fisher) was used for both microinjection and imaging. Images were acquired with a Zeiss 40×NA=1.30 oil objective and MicroMax CCD camera (Princeton Instruments Inc.) operated with MetaMorph Version 4.01 imaging software.

Results

Small segments of Arf and Hdm2 participate in Arf/Hdm2 interactions. It has been previously shown that a fragment of mouse p1$^{Arf}$ containing the N-terminal 37 amino acids (mArfN37) can (i) bind Hdm2, (ii) cause the relocalization of Hdm2 to nucleoli, and (iii) induce cell cycle arrest in MEFs [see, U.S. patent application Ser. No. 09/480,718, Filed Jan. 7, 2000, the contents of which are hereby incorporated by reference in their entireties; Weber et al., *Nat. Cell Biol.*, 1:20-26 (1999)]. Further, a fragment of Hdm2 containing amino acids 140-350 has been show to be capable of binding mArfN37 and to be relocalized to nucleoli in a mArfN37-dependent manner. A smaller fragment, Hdm2 210-304, has also been shown to be capable of binding mArfN37 on the basis of Arf affinity chromatography [Weber et al., *Mol. Cell. Biol.*, 20:2517-2528 (2000)]. However, because mArfN37 is a relatively small polypeptide, it was determined whether it could bind a correspondingly small segment of Hdm2. To test this hypothesis and to monitor Arf/Hdm2 binding reactions quantitatively, Hdm2 constructs were prepared spanning amino acids 210-304 of SEQ ID NO:8 and 210-275 of SEQ ID NO:8 and then it was determined whether they could bind mArfN37 using surface plasmon resonance (SPR). Both Hdm2 210-304 and 210-275 bind tightly to His-tagged mArf37 that was immobilized on the SPR biosensor surface using a covalently linked His antibody (FIG. 1). The two Hdm2 fragments did not bind a control surface that lacked His-mArfN37.

The binding results discussed above were verified (based on an in vitro assay using SPR) in a biological setting by monitoring the interaction of p 19$^{Arf}$ and Hdm2 fragments in NIH 3T3 cells that lack the gene for Arf using fluorescence microscopy. p19$^{Arf}$ was tagged with GFP (green fluorescent protein) and expressed in cells after transfection with an expression plasmid, as previously described [Weber et al., *Nat. Cell Biol.*, 1:20-26 (1999); Weber et al., *Mol. Cell. Biol.*, 20:2517-2528 (2000)], while Hdm2 was chemically tagged with the fluorescent dye TEXAS RED® ($C_{31}H_{29}S_2N_2O_6Cl_1$) and introduced into cells by microinjection. The results show that GFP-p19$^{Arf}$ is localized in nucleoli after transfection, whereas, in direct contrast, Hdm2 210-304 is evenly dispersed in the nucleoplasm after microinjection in the absence of p19$^{Arf}$. When GFP-p19$^{Arf}$ and Hdm2 210-304 are introduced into cells together, the two proteins become co-localized within nucleoli. The smaller fragment of Hdm2, Hdm2 210-275, exhibits similar localization properties in the absence and presence of GFP-p19$^{Arf}$. Together, the SPR and cell localization results show that a ~100 amino acid central segment of Hdm2 interacts with Arf and that fragments containing this segment can be sequestered within nucleoli in the same manner as shown previously for full-length Hdm2 [Weber et al., *Nat. Cell Biol.*, 1:20-26 (1999); Weber et at, *Mol. Cell. Biol.*, 20:2517-2528 (2000)].

Structural properties of mArfN37 and Arf-binding Hdm2 fragments. Knowing that mArfN37 and Hdm2 210-304 (and Hdm2 210-275) interact and that the interactions appear to be biologically relevant, the structural properties of these domains were investigated. Previous work showed that mArfN37 is unstructured in aqueous solution and that the peptide adopts a bi-helical conformation in 30% trifluoroethanol [DiGiammarino et al., *Biochem.*, 40:2379-2386 (2001)]. CD spectra for Hdm2 210-304 and 210-275 show that these two Arf-binding polypeptides are also unstructured. The CD spectrum for mArfN37 is also shown, for reference. A similar conclusion can be reached on the basis of the $^1H$-$^{15}N$ 2D correlation spectra for Hdm2 210-304 and 210-275. The observed chemical shift values in both the $^1H$ and $^{15}N$ dimensions cluster near random coil values [Schwarzinger et al., *J. Amer. Chem. Soc.*, 123:2970-2978 (2001)] and are consistent with a general lack of secondary and tertiary structure [Kriwacki et al., *Proc. Natl. Acad. Sci. USA*, 93:11504-11509 (1996)]. Furthermore, heteronuclear $\{^1H\}$-$^{15}N$ NOE values for Hdm2 210-275 are all negative and are consistent with the conclusion that the Arf-binding segment of Hdm2, prior to binding Arf, is conformationally disordered and highly flexible.

Secondary structure prediction methods were used to gain further insight into the structural properties of the N-terminal segment of Arf, and the Arf-binding segment of Hdm2. Prior analysis of mArfN37 alone using a variety of secondary structure prediction algorithms did not yield consistent results [DiGiammarino et al., *Biochem.*, 40:2379-2386 (2001)]. However, when the neural net-based Jnet algorithm [Cuff et al., *Proteins*, 40:502-11 (2000)] (available through the Jpred site at jura.ebi.ac.uk:8888) was used to analyze the human, mouse, and opossum Arf sequences simultaneously, two short β-strands are predicted within the N-terminal 37 amino acids (FIG. 2a), between residues 4-12 and 20-27, respectively. The Jnet approach, which is based on the principle that secondary structure is conserved within evolutionarily related proteins, has been shown to predict secondary structure with 73% or higher accuracy. For Arf, both β-strands are predicted with high confidence (FIG. 2a). Prior structure predictions were probably hampered by the unusual nature of the mArfN37 sequence, which contains 27% Arg residues (10/37) and has a correspondingly high predicted pI value (12.6).

Figure 3:
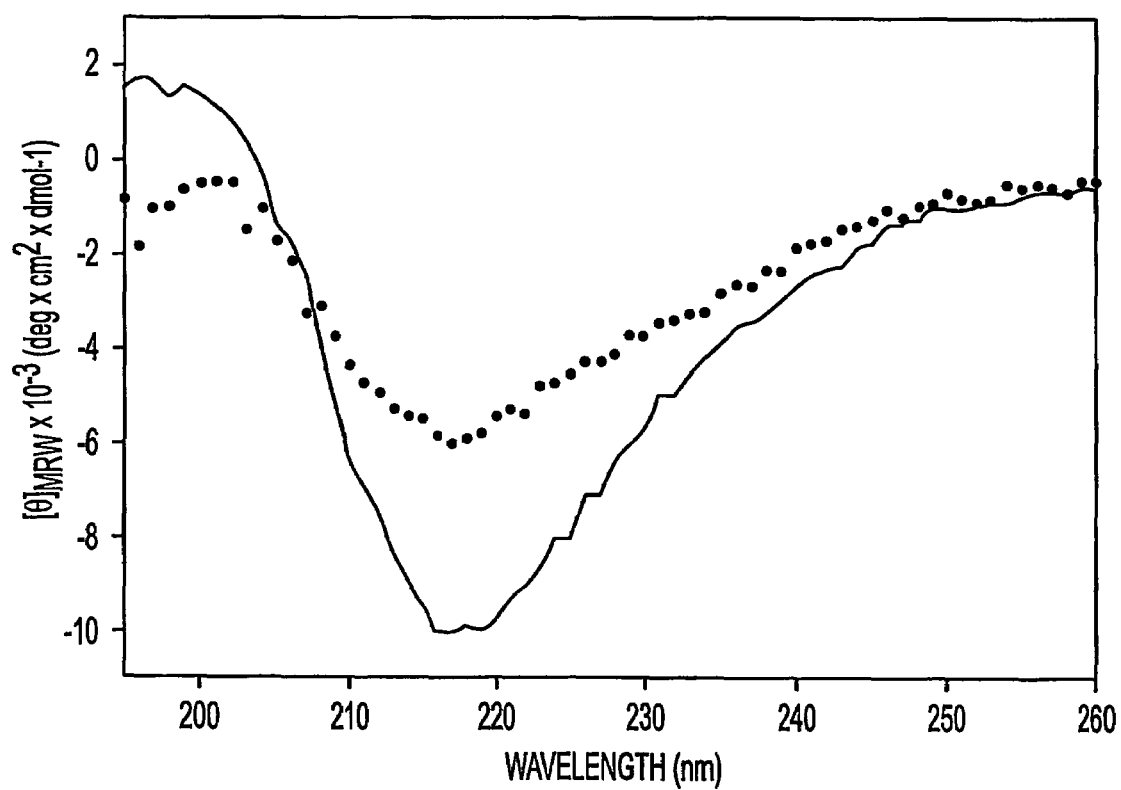
FIG. 3 shows the characterization of Arf:Hdm2 assemblies. CD spectra of mArfN37 complexed with Hdm2 210-304 (solid line) and Hdm2 210-275 (dotted line) are consistent with β-strand secondary structure. The molar ratio of the two species in each sample is given.

In contrast to mArfN37, Hdm2 210-304 is highly acidic (17/95 Asp and 14/95 Glu, 31/95 total, or 33%; the predicted pI is 3.5) and very hydrophilic due additionally to its high Ser content (17/95). Interestingly, as for the Arf N-terminus, two short segments of β-strand are predicted by Jnet within the Arf-binding domain of Hdm2, between residues 245-253 and 275-282 (FIG. 2b). Many residues within the β-strands are also predicted to be less than 25% solvent exposed. The remainder of the polypeptide is predicted to be unstructured and solvent exposed. The opposed charge characteristics of mArfN37 and Hdm2 210-304 suggest that electrostatic forces play a role in the interactions between the two polypeptides. The prediction of two β-strands in both mArfN37 and Hdm2 210-304 suggests that β-strand secondary structure is involved in Arf/Hdm2 interactions.

β-strand secondary structure forms when Arf and Hdm2 interact. Interestingly and in accord with the secondary structure predictions discussed above, a striking transition from random conformations to β-strand secondary structure is observed when mArfN37 and Hdm2 210-304 (and Hdm2 210-275) are mixed (FIG. 3). This structural transition is induced when mArfN37 is added to an Hdm2 fragment and when an Hdm2 fragment is added to mArfN37. Data from gel filtration chromatography and NMR spectroscopy shows that the mArfN37 and Hdm2 210-304 do not form a bimolecular complex involving small numbers of molecules but rather form large, extended structures with predominantly β-strand secondary structure. First, gel filtration chromatography shows that, when mixed, mArfN37 and Hdm2 210-304 elute together in the void volume. In contrast, the uncomplexed species elute at times consistent with monodisperse, conformationally extended polypeptides. Second, NMR resonances for $^{15}N$-mArfN37 or $^{15}N$-Hdm2 210-304 (and $^{15}N$-Hdm2 210-275) are broadened beyond detection when an unlabeled form of the appropriate binding partner is added to the solution. At mArfN37:Hdm2 210-304 (or mArfN37:Hdm2 210-275) molar ratios that produce maximal β-strand secondary structure based on ellipticity at 200 nm using CD, resonances cannot be observed for the isotope-labeled component of Arf/Hdm2 mixtures. Further, the NMR spectra are consistent with slow exchange between the free and bound states. These results indicate that β-strand secondary structure forms when mArfN37 and Hdm2 210-304 (and Hdm2 210-275) interact and that this secondary structure exists in the context of supramolecular assemblies that can be described as β networks.

Characterization of Arf Hdm2 assemblies. As discussed above, the addition of mArfN37 to Hdm2 210-304 results in the formation of supramolecular assemblies comprised of β-strands. Stepwise addition of sub-stoichiometric amounts of mArfN37 to Hdm2 210-304 increased β-strand secondary structure content as judged by the change in ellipticity at 200 nm using CD. Ellipticity at 200 nm was monitored because the largest difference in ellipticity between random and β-strand conformations was observed at this wavelength. The binding of mArfN37 to Hdm2 210-304, as monitored in this way, is saturable. Similar results were obtained when mArfN37 was mixed with the shorter fragment of Hdm2, Hdm2 210-275. Further, saturable binding is also observed when the Hdm2 fragments were added to an excess of mArfN37. These findings indicate that there are a limited number of binding sites for mArfN37 within Hdm2 210-304 and that discreet structures (containing β-strands) form when mArfN37 and Hdm2 210-304 (or 210-275) are mixed. For mArfN37 added to Hdm2 210-304, the plot of ellipticity versus amount of protein added is linear, indicating that each molecule of mArfN37 added binds completely to the Hdm2 fragment. Similar behavior is observed when mArfN37 binds Hdm2 210-275. These findings suggest that the equilibrium dissociation constant ($K_D$) for the interactions is less than the concentrations used (~5×10$^{-6}$M).

Formation of mArfN37:Hdm2 210-304 (and mArfN37:Hdm2 210-275) assemblies was observed under a variety of conditions, including pH values between 4 and 10, and salt concentrations from 0 to 2 M NaCl. Furthermore, the assemblies were not disrupted by chemical denaturation (4 M urea), treatment with an organic solvent (50% acetonitrile (vol:vol)), or treatment with a mild detergent (10 mM CHAPSO). These results indicate that the mArfN37:Hdm2 210-304 assemblies are thermodynamically stable. This conclusion is further supported by the results of thermal denaturation experiments using CD. The assembly formed by adding mArfN37 to an excess of Hdm2 210-304 to a final molar ratio of 2:1 (mArfN37:Hdm2 210-304) is stable to heating up to ~75° C. For example, the CD spectrum for the mArfN37:Hdm2 210-304 assembly prepared in this way does not change when the sample temperature is increased from 25° C. to 75° C. The CD spectrum does change above 75° C., and the changes are consistent with unfolding of the supramolecular assemblies. In particular, the intensity of spectral features indicative of β-strands is reduced and finally completely eliminated at 95° C. When CD ellipticity at 216 nm is plotted versus temperature, the shape of the curve above 75° C. resembles other protein denaturation curves that are known to involve a cooperative unfolding process. The melting data was fit with a sigmoidal function to determine the melting temperature ($T_m$), defined as the midpoint of the melting curve. Denaturation experiments were performed at three different ionic strengths, 0, 150 and 300 mM NaCl, and yield $T_m$ values of 77, 65 and 52° C., respectively. Similar $T_m$ values were obtained with the assembly formed by adding mArfN37 to Hdm2 210-275.

Dual binding motifs in Arf and Hdm2 mediate intermolecular interactions. The N-terminal domains of human and mouse Arf have similar primary structure (FIG. 2a) and contain an arginine-rich, repeated motif (FIG. 4) [DiGiammarino et al., *Biochem.*, 40:2379-2386 (2001)]; this is termed the "Arf motif" the first and second repeats are termed "A1" and "A2", respectively. [In the mouse Arf protein (p19$^{Arf}$) A1 and A2 have the amino acid sequences of SEQ ID Nos:9 and 10 respectively, whereas in the human Arf (p14$^{Arf}$), A1 and A2 have the amino acid sequences of SEQ ID NOs:11 and 12 respectively.

Importantly, mArfN37, which contains both of the Arf motifs in the mouse Arf sequence, has been shown to possess biological properties comparable to full-length mouse Arf. These properties include nucleolar localization, the ability to sequester Mdm2 and Hdm2 in nucleoli and the ability to cause cell cycle arrest [Weber et al., *Mol. Cell. Biol.*, 20:2517-2528 (2000); DiGiammarino et al., *Biochem.*, 40:2379-2386 (2001)]. Furthermore, a construct containing residues 1-20 of human Arf has been shown to activate p53 in cellular assays [Midgley et al., *Oncogene*, 19:2312-23 (2000)]. The existence of two structural motifs within mArfN37 was suggested on the basis of the solution structure of mArfN37 determined in the presence of trifluoroethanol (TFE) using NMR spectroscopy [DiGiammarino et al., *Biochem.*, 40:2379-2386 (2001)]. In TFE, mArfN37 is bi-helical, with the two Arf motifs contained by helices that are 12 amino acids in length. Based on the observation that β-strands form when mArfN37 and Hdm2 210-304 interact, and the prediction of β-strands within the interacting segments, the bi-helical conformation of mArfN37 in TFE is probably not relevant to the Hdm2-bound conformation. However, the observation of similar structure for the mouse A1 and A2 segments in mArfN37 did suggest that the two Arf motifs may function in Hdm2 binding in a structurally similar and mechanistically coordinated manner. With these ideas in mind, the role the two Arf motifs play in Hdm2 binding was investigated by monitoring the binding of short peptides derived from human and mouse Arf to Hdm2 fragments using surface plasmon resonance and CD.

Figure 5A:
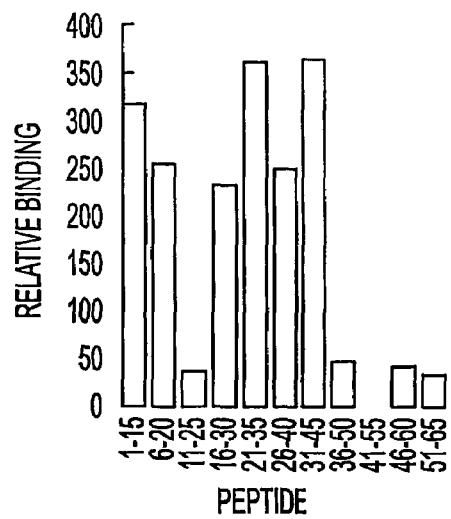
FIGS. 5a-5c show the surface plasmon resonance (SPR) binding experiments with Arf and Hdm2 peptides which reveal sites of interaction. His-tagged Hdm2 210-304 (FIGS. 5a-5b) and His-tagged mArfN37 (FIG. 5c) were captured on the SPR surface with an anti-His antibody. The binding of peptides derived from the N-terminus of mouse Arf (FIG. 5a), human Arf (FIG. 5b), or the central, acidic domain of Hdm2 (FIG. 5c) was monitored. *, this peptide is anomalous because it binds extensively to the reference cell.
Figure 5B:
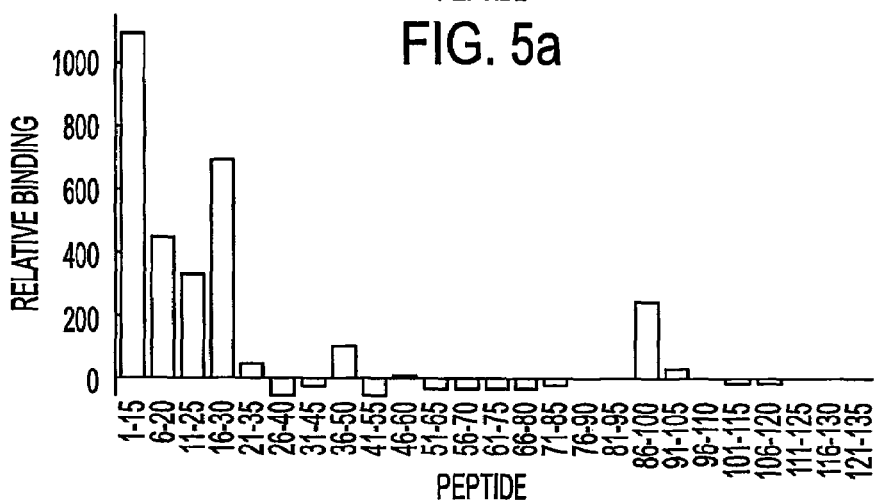

Two libraries of peptides 15 amino acids in length were synthesized based on the sequence of exon 1β of mouse p19$^{Arf}$ and the entire sequence of human p14$^{Arf}$. The sequence for the first peptide in each library corresponded to the first 15 amino acids of the protein sequences. The N-terminus for the second peptide was shifted forward 5 residues to position 6 and spanned residues 6-20, and each subsequent peptide had an additional 5-residue forward shift of the N-terminus. This approach yielded two libraries of overlapping peptides spanning mouse p19$^{Arf}$ residues 1-64 and human p14$^{Arf}$ residues 1-132. The ability of these peptides to bind Hdm2 fragments was determined using the surface plasmon resonance (SPR) technique with a Biacore 3000 instrument. His affinity tagged Hdm2 210-304 was immobilized on the surface of a C-1 chip through capture by a covalently cross-linked anti-His antibody. Library peptides were allowed to flow over the Hdm2 surface, or over a control surface lacking an Hdm2 fragment. Relative binding affinity was judged on the basis of the maximal SPR signal detected after binding for 10 minutes. This unusually long inject time was used because some peptides exhibited slow association kinetics; the long association time allowed weak binding peptides to be identified. The peptides that exhibited the largest relative binding affinity map to the N-termini of mouse and human Arf (FIGS. 5a and 5b); however, the length of the Hdm2-binding segment for the two is slightly different. For example, the first four peptides from the human library bind Hdm2 210-304; these span the segment of human p14$^{Arf}$ that encloses the two Arf motifs. In contrast, 6 of the first 7 peptides of the mouse p19$^{Arf}$ library bind Hdm2 210-304. The first five of these enclose the two Arf motifs while the last, spanning residues 31-45, lacks elements of an Arf motif but contains the RRPR motif that is the nucleolar localization signal (NoLS) for mouse Arf. One additional human Arf peptide binds Hdm2 210-304; this spans residues 86-100 and contains the NoLS (with the sequence RRPR) for human Arf. Through an unknown mechanism, the RRPR motif within these nucleolar localization signals causes the polypeptides to become localized in nucleoli of eukaryotic cells.

Figure 5C:
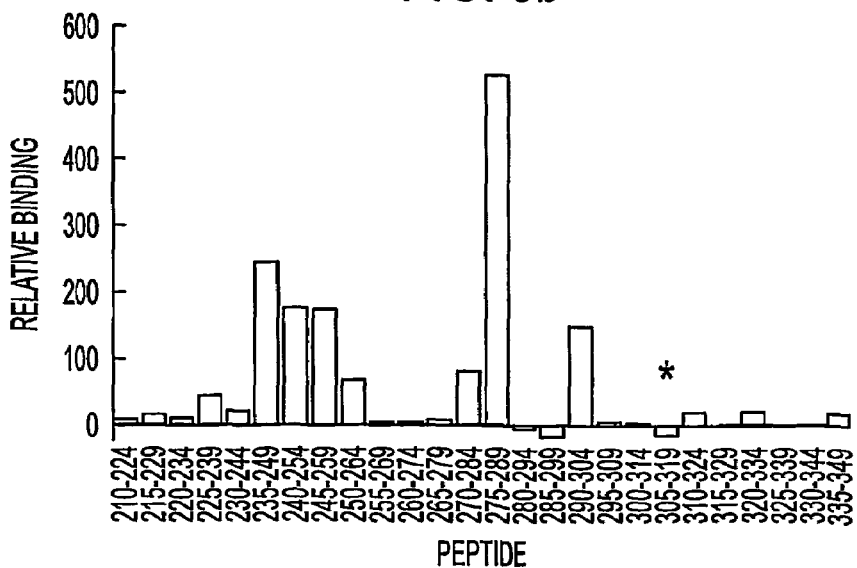

A similar approach using short synthetic peptides and SPR was used to map the segments of Hdm2 that bind mArfN37 (FIG. 5c). Peptides within two segments of the central region of Hdm2 bind with relatively high affinity to mArfN37, including those spanning residues 235-259 and 275-289 of SEQ ID NO:8. The first of these as Arf-binding segment is termed "H1" and the second is termed segment "H2". The peptide containing residues 290-304 of SEQ ID NO:8 exhibits modest affinity for mArfN37; however, based on results discussed below this appears to be due to non-specific electrostatic forces.

To investigate the roles of individual Arf motifs (A1 and A2) and Arf-binding segments of Hdm2 (H1 and H2) in the interactions between Arf and Hdm2 the binding of peptides containing these small segments (A1, A2, H1, or H2) to larger protein fragments of the corresponding binding partner (mArfN37 or Hdm2 210-304) were monitored using the CD-based binding assay. Peptides corresponding to the mouse Arf motifs, A1 (1-14) and A2 (16-30), bind independently to Hdm2 210-304 and induce the transition from random conformations to β-strand secondary structure. Similarly, peptides containing the human Arf motifs, A1 (1-14) and A2 (16-30), bind Hdm2 210-304 and produce the random-to-β-strand structure transition. Peptides from the Hdm2 library that were positive for mArfN37 binding on the basis of SPR (i.e. those within H1 and H2) were mixed with mArfN37 and binding was monitored in the same manner. Three peptides from the H1 segment and one from the H2 segment of Hdm2 induce β-strand secondary structure when mixed with mArfN37 (FIG. 2c). These experiments indicate that peptides containing A1, A2, H1 or H2 can interact with larger fragments of the target protein and that the interactions also occur through the formation of O-sheet secondary structure. Peptides lacking A1, A2, H1 or H2 failed to induce the structural transition. Importantly, however, further reduction in the size of the interacting species led to a loss of Arf/Hdm2 binding as judged by a failure to induce structure in CD titration experiments. For example, while peptides derived from the A1 or A2 segments of Arf bind Hdm2 210-304, they fail to bind short peptides (15 amino acids in length) derived from the H1 or H2 segments of Hdm2. Similarly, while peptides derived from the H1 or H2 segments of Hdm2 bind mArfN37, they fail to bind peptides derived from the A1 or A2 segments of mouse or human Arf. Furthermore, mixtures of two, three, or four different peptides that contain the important binding segments (A 1, A2, H1, and H2) fail to interact, in contrast to the results obtained when A1 and A2, or H1 and H2, are covalent linked in larger protein fragments. Apparently, cooperative interactions between covalently linked binding segments from one protein (A1 and A2 of Arf, or H1 and H2 of Hdm2) are minimally required for Arf/Hdm2 interactions.

Arf/Hdm2 interactions mediate nucleolar colocalization. Microinjection and live cell imaging were used to determine whether the Hdm2 domains that were shown to bind Arf in the SPR and CD binding studies bound to Arf in cells and whether these domains are sequestered within nucleoli by Arf. Hdm2 deletion constructs tagged with a fluorescent label (TEXAS RED® ($C_{31}H_{29}S_2N_2O_6Cl_1$) were microinjected into the nucleus of NIH 3T3 cells. Importantly, the NIB 3T3 cell line used lacks the gene for Arf. Nuclear microinjection was used because the Hdm2 constructs containing the central Arf-binding domain lack the nuclear localization signal found between residues 181-186. A covalently bound fluorescent label was used to detect Hdm2 fragments instead of immuno fluorescence to avoid nonspecific background staining and staining variability due to differential antibody reactivity. In addition, preliminary results using the antibody of choice to detect Hdm2 210-326 (2A10) [Weber et al., *Nat. Cell Biol.*, 1:20-26 (1999)] gave poor staining results, possibly because the antibody epitope is very near the Arf binding site and Arf binding inhibits antibody binding [Midgley et al., *Oncogene*, 19:2312-23 (2000)]. Arf was delivered to cells prior to microinjection by transfection with a plasmid expressing GFP-p19$^{Arf}$.

TEXAS RED® ($C_{31}H_{29}S_2N_2O_6Cl_1$) labeled Hdm2 deletion constructs containing residues 210-275, 210-304, 277-350 and 277-491 were individually injected into cells in the absence or presence of the GFP-p19$^{Arf}$ fusion protein. In cells that did not express Arf, all constructs were localized in the nucleoplasm and appeared to be excluded from nucleoli. In contrast, when GFP-Arf was expressed, three of these constructs that contain all or portions of the central, Arf-binding domain exhibited a distinct nucleolar localization pattern. For example, Hdm2 210-275, 210-304 and 277-491 all displayed nucleolar localization when Arf was expressed. Hdm2 277-350 also binds GFP-Arf, but causes the complex to be localized in the nucleoplasm rather than in nucleoli. These results are consistent with a report [Weber et al., *Mol. Cell. Biol.*, 20:2517-2528 (2000)] showing that Hdm2 constructs that contain a segment spanning residues 210-304 bind Arf and are sequestered within nucleoli. The use of live cell imaging also allowed the kinetics of localization to be monitored. Within 5 minutes after injection of Hdm2 constructs, complex relocalization was complete.

Texas Red™ labeled Hdm2 deletion constructs containing residues 210-275, 210-304, 277-350 and 277-491 were individually injected into cells in the absence or presence of the GFP-p19$^{Arf}$ fusion protein. In cells that did not express Arf, all constructs were localized in the nucleoplasm and appeared to be excluded from nucleoli. In contrast, when GFP-Arf was expressed, three of these constructs that contain all or portions of the central, Arf-binding domain exhibited a distinct nucleolar localization pattern. For example, Hdm2 210-275, 210-304 and 277-491 all displayed nucleolar localization when Arf was expressed. Hdm2 277-350 also binds GFP-Arf, but causes the complex to be localized in the nucleoplasm rather than in nucleoli. These results are consistent with a report [Weber et al., *Mol. Cell. Biol.*, 20:2517-2528 (2000)] showing that Hdm2 constructs that contain a segment spanning residues 210-304 bind Arf and are sequestered within nucleoli. The use of live cell imaging also allowed the kinetics of localization to be monitored. Within 5 minutes after injection of Hdm2 constructs, complex relocalization was complete.

A1 and H1 Peptides Self-Assemble into Amyloid-Like Fibrils

Figure 6A:
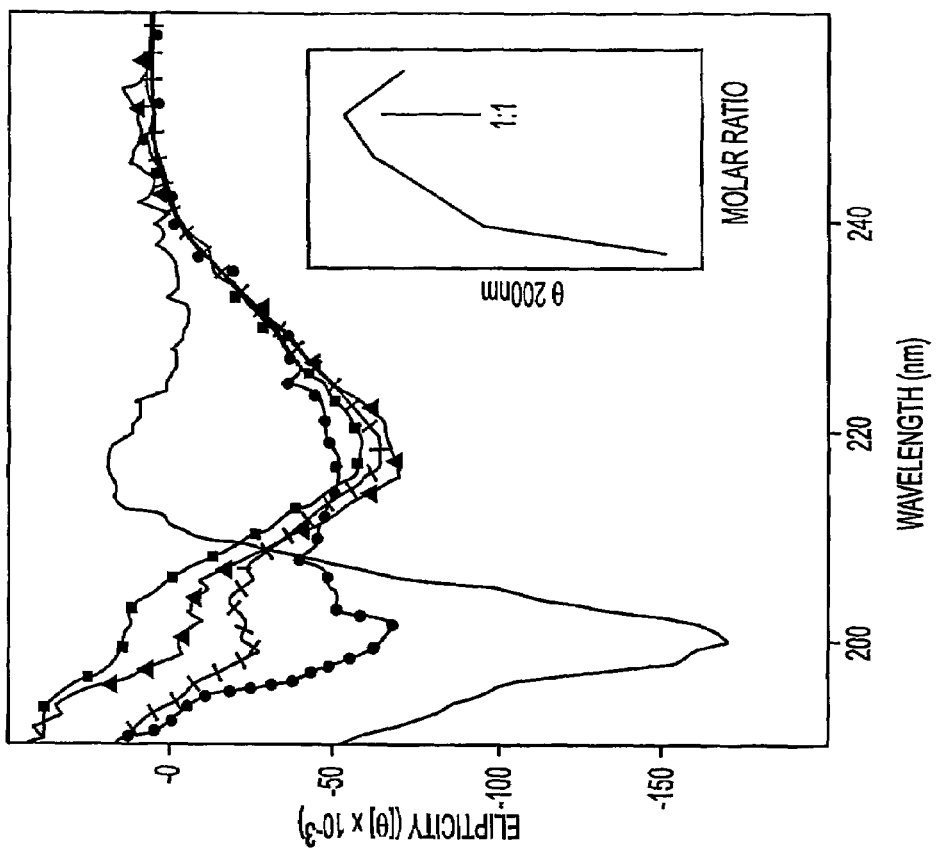
FIGS. 6a and 6b shows that A1/H1 co-assemblies comprise β-strands.
Figure 6B:
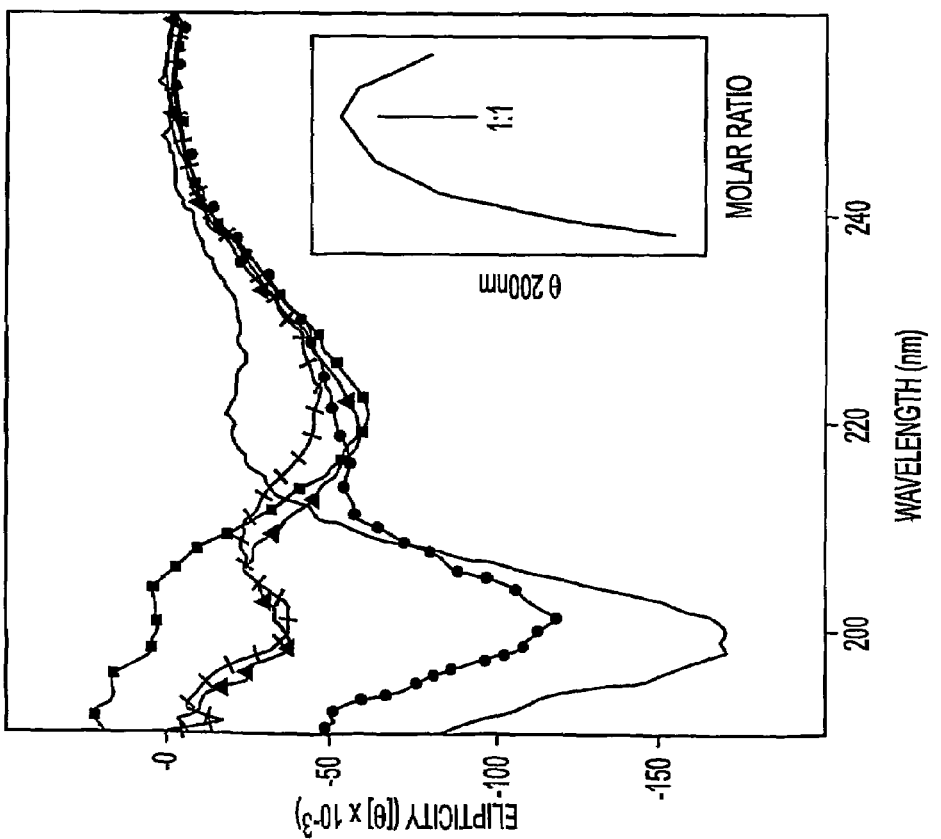

Analysis of the structural and self-assembly properties of short peptides excised from the interacting domains of Arf and Hdm2 using Circular dichroism (CD) spectropolarimetry shows that isolated peptides comprising the A1 (SEQ ID NO:26, MVRRFLVTLRIRRA) and H1 (SEQ ID NO:27, SVSDQFSVEFEVESL) peptides (p14ARF 1-14 and Hdm2 240-254, respectively) are highly disordered in solution (FIG. 6*a* & *b*, red traces). However, when combined, the components of the binary mixture self-assemble, forming β-strand-containing supramolecular structures of low solubility (FIG. 6*a* & *b*).

Figure 1B:
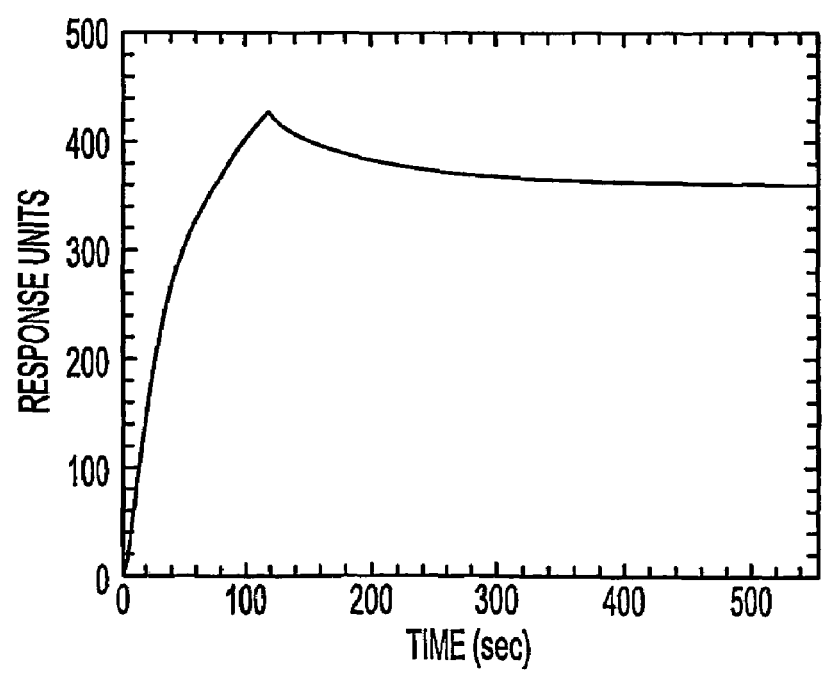

CD spectra were recorded with an Aviv 62DS instrument in 5 mM potassium phosphate (pH 7.0) using a 1 mm cuvette. In FIG. 1A, A1 was 4.5 µM, molar ratios were: 1:0.0, 1:0.1, 1:0.6, 1:0.9, & 1:1.3. In FIG. 1B, H1 was 2.5 µM, molar ratios were: 1:0.2, 1:0.7, 1:1.0, & 1:1.3. Data was collected for 3 seconds in 1 nm steps and 10 scans were averaged for each spectrum. The appearance of a minimum in the CD spectra of the assemblies near 216 nm and the increase in ellipticity near 200 nm is consistent with the formation of β-strand-containing structures.

The solution of binary assemblies is characterized by visible turbidity and the disappearance of 1H NMR resonances that, before mixing, were observed for the monodisperse, free peptides (data not shown). When either peptide was titrated into a solution of the other, both NMR and CD spectra revealed that binding was saturable. An end point was reached when the molar ratio of A1:H1 was 1:1. For example, further additions of the H1 peptide led to the appearance of disordered spectral features consistent with unbound, free H1 peptide (inset, FIG. 6*a*). The Fourier transform infrared (FT-IR) spectrum of the co-assemblies confirms the CD results and allows the β-structures to be classified as anti-parallel β-strands on the basis of the absorbances at 1618 cm-1 and 1679 cm-1 (FIG. 7) [Casal, H. L.; Kohler, U.; Mantsch, H. H., *Biochim Biophys Acta* 957:11-20 (1988)]. In summary, the individually disordered A1 and H1 peptides self-assemble into supramolecular structures comprised of anti-parallel β-strands.

A1/H1 Coassembly May Involve Electrostatic and Hydrophobic Interactions

The A1 peptide (SEQ ID NO:26) from Arf contains five Arg residues (positions 3, 4, 10, 12 & 13), two of which (positions 3 & 10) are found within an evolutionarily conserved motif referred to as the Arf motif [Bothner, B.; Lewis, W. S.; DiGiammarino, E. L.; Weber, J. D.; Bothner, S. J.; Kriwacki, R. W., *J. Mol. Biol.* 314:263-277 (2001)]. In contrast, the H1 peptide (SEQ ID NO:27) from Hdm2 is oppositely charged, containing one Asp residue (position 4) and three Glu residues (positions 9, 11 & 13). Additionally, both peptides contain several bulky, hydrophobic residues. Although, not wanting to be bound by any particular theory, it is likely that the process of co-assembly for A1/H1 peptide and Arf/Hdm2 polypeptide fragment coassemblies is mediated by attractive electrostatic interactions between Arg and Asp/Glu residues from different peptide molecules which ultimately are found on the same face of an anti-parallel β-sheet. The hydrophobic residues, which are found between the charged residues in both A1 and H1, are likely to further stabilize A1/H1 co-assemblies through intermolecular hydrophobic interactions. Repulsive electrostatic interactions between like-charged side chains in the individual peptides may favor extended conformations that promote self-assembly.

A1/H1 Co-Assemblies Comprise Anti-Parallel β-Strands

Figure 7A:
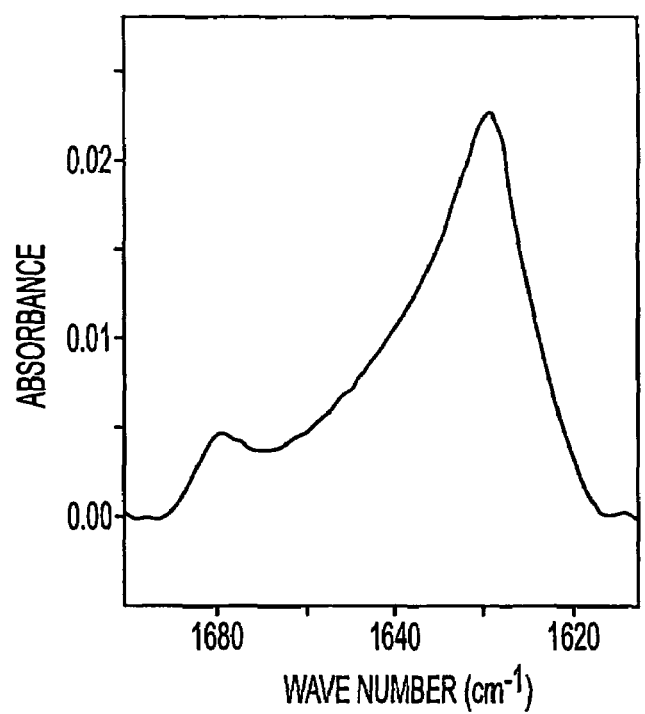
FIGS. 7a and 7b shows that the A1/H1 co-assemblies comprise anti-parallel β-strand secondary structure.
Figure 7B:
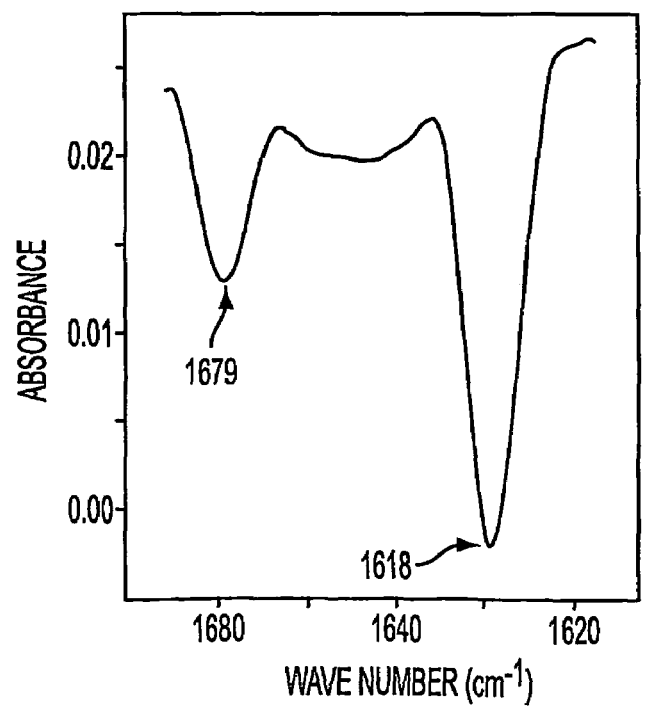

FT-IR spectra (2000 scans each, 2 cm-1 resolution) were recorded using a Bruker Vector 22 instrument using with an attenuated total reflectance cell. The concentration of each peptide was 1 mg/mL in 10 mM Tris, pH 7.0 in 2H2O. The Fourier transform infrared (FT-IR) spectrum of A1/H1 co-assemblies provided in FIG. 7(a) is consistent with anti-parallel β-strand secondary structure. Absorbance maxima in the protein amide I region were observed at 1618 cm-1 and 1679 cm-1. FIG. 7(b) provides the second-derivative analysis of FT-IR spectrum provided in panel (a).

Interestingly, the FT-IR spectrum of the A1/H1 peptide co-assemblies described herein were observed to bear a striking resemblance to those of amyloid-like fibrils formed from several different pure proteins [Zurdo, J.; Guijarro, J. I.; Dobson, C. M., J. Am. Chem. Soc. 123:8141-8142 (2001); Zurdo, J.; Guijarro, J. I.; Jimenez, J. L.; Saibil, H. R.; Dobson, C. M., J Mol Biol 311:325-340 (2001); Bouchard, M.; Zurdo, J.; Nettleton, E. J.; Dobson, C. M.; Robinson, C. V., Protein Sci 9:1960-1967 (2000); and Soto, C.; Castano, E. M.; Frangiones, B.; Inestrosa, N. V., The Journal of Biological Chemistry 270:3063-3067 (1995)].

Electron Microscopy Reveals that A1/H1 Peptide Co-Assemblies Adopt Structures Similar to Amyloid Protofibrils and Fibrils Electron microscopy was used in order to extend the structural analysis of the A1/H1 peptide coassemblies. More specifically, electron microscopy was used to determine whether the supramolecular structure of A1/H1 co-assemblies was similar to that of amyloid fibrils. Microscopy revealed that A1/H1 co-assemblies adopt structures that are similar to amyloid protofibrils and fibrils. Protofibrils were prepared by combining 1 mg/mL solutions of the A1 and H1 peptides in 20 mM Tris, pH 7.0 at 23° C. The structure of the A1/H1 pepetide co-assemblies become organized after heating at 70° C., pH 3.5 for 100 hours. Samples were dried onto freshly glow-discharged, carbon-coated, EM grids and negatively-stained with 2% phosphotungstic acid (pH 6.4). Heat treatment of the A1/H1 assemblies was performed at pH values from 2.0 to 8.5 and the structural transition from protofibrils fibrils was observed only at pH 3.0 and 3.5.

Figure 8A:
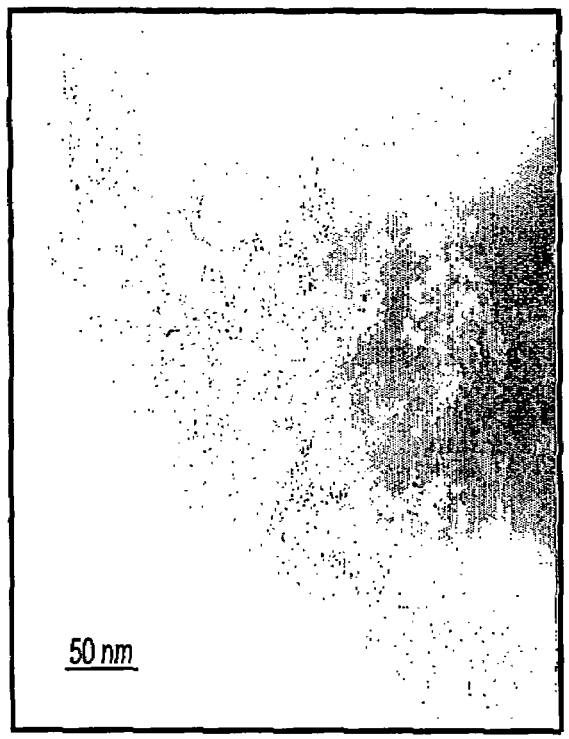
FIGS. 8a and 8b provide photomicrographs illustrating that A1/H1 peptide coassemblies adopt structures similar to amyloid protofibrils and fibrils. Protofibrils were prepared by combining 1 mg/mL solutions of the A1 and H1 peptides in 20 mM Tris, pH 7.0 at 23° C.

As disclosed herein, it was observed that the resulting assemblies comprise networks of short, thin fibrils that are 10-20 nm long and less than 5 nm wide (FIG. 8a). Thus it was determined that the resulting assemblies are morphologically similar to protofibrils derived from the β-amyloid peptide [Soto, C.; Castano, E. M.; Frangiones, B.; Inestrosa, N. V., The Journal of Biological Chemistry 270:3063-3067 (1995)], insulin [Bouchard, M.; Zurdo, J.; Nettleton, E. J.; Dobson, C. M.; Robinson, C. V., Protein Sci 9:1960-1967 (2000)], lysozyme [Krebs, M. R.; Wilkins, D K.; Chung, E. W.; Pitkeathly, M. C.; Chamberlain, A. K.; Zurdo, J.; Robinson, C. V.; Dobson, C. M., J Mol Biol 300:541-549 (2000)] and an SH3 [Zurdo, J.; Guijarro J. I.; Jimenez, J. L.; Saibil, H. R.; Dobson, C. M. J Mol Biol 311:325-340 (2001)].

Figure 8B:
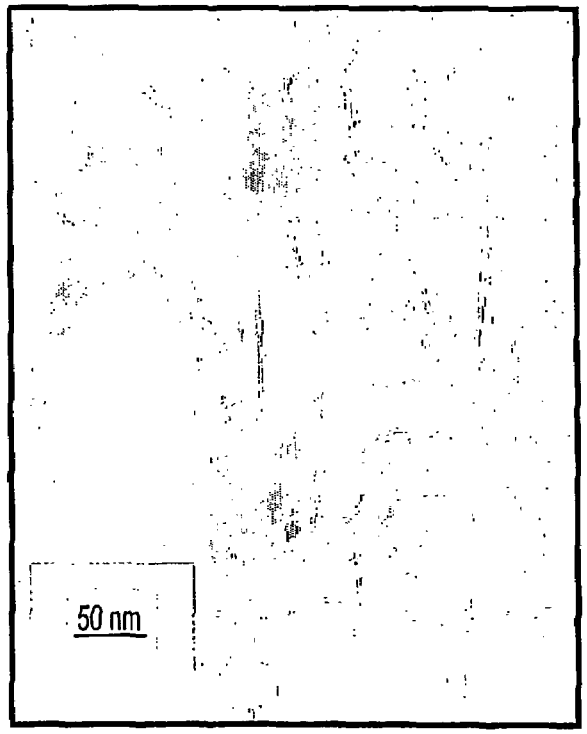

Denaturing conditions are known to promote the conversion of many proteins from the native state to amyloid-like fibrils. To test their stability and potential for further self-assembly, A1/H1 protofibrils were heated. Electron microscopy revealed that the structure of A1/H1 co-assemblies became more organized after heat treatment. More specifically, it was observed that the assemblies took on the appearance of distinct fibrils that were hundreds of nm in length. The long fibrils appeared to be bundled together into parallel, flat ribbons comprised of 3-6 individual fibrils (FIG. 8b).

A1/H1 Co-Assemblies Fail To Bind Congo Red And Thioflavin

The chemical dyes, Congo red (CR) [Klunk, W. E.; Pettegrew, J. W.; Abraham, D. J., J Histochem Cytochem 37:1273-1281 (1989)] and thioflavin T (ThT), [Levine, H. Amyloid 2:1-6 (1995)] bind specifically to amyloid fibrils generated from a wide variety of proteins and binding is associated with characteristic changes in absorbance and fluorescence spectra of the dyes. Surprisingly, the A1/H1 peptide co-assemblies, before and after heat treatment, failed to bind CR and ThT. While the spectral and structural characteristics of these assemblies are very similar to those of classical amyloid fibrils, their binary nature seems inconsistent with Congo red and ThT dye binding.

Discussion

The studies disclosed above focused on understanding the molecular basis of Arf and Hdm2, interactions and their relationship to biological function. Previously, the domains mediating Arf and Hdm2 interactions to the N-terminal 37 amino acids of p19$^{Arf}$ [Weber et al., Nat. Cell Biol., 1:20-26 (1999); Weber et al., Mol. Cell. Biol., 20:2517-2528 (2000)] and the central acidic domain of Hdm2 (210-304) [Weber et al., Mol. Cell. Biol., 20:2517-2528 (2000)] had been localized. Structural analysis of mArfN37 in solution showed that this domain is dynamically disordered in the unbound state [DiGiammarino et al., Biochem., 40:2379-2386 (2001)]. Interestingly, the Arf interacting domain of Hdm2 is shown herein to also be dynamically disordered in solution. For example, CD spectra for Hdm2 acidic domain-containing fragments (210-275 and 210-304) show no signs of secondary structure and NMR spectra reveal poorly dispersed resonances consistent with random coil chemical shift values. Further, steady-state heteronuclear $\{^{1}H\}$-$^{15}N$ NOE values for Hdm2 210-275 indicated that amides throughout the entire polypeptide are highly dynamic. Importantly, as shown herein, these disordered Arf and Hdm2 domains bind to each other in both in vitro and cellular assays demonstrating the relevance of the disordered states to biological function.

The importance of dynamically disordered proteins or domains in biological systems, and in the regulation of cell division, is well established [Kriwacki et al., Proc. Natl. Acad. Sci. USA, 93:11504-11509 (1996); Uversky et al., Protein Sci., 8:161-73 (1999); Sosnick et al., Proteins, 24:427-32 (1996); Dyson et al., Biol., 5:499-503 (1998); Plaxco et al., Nature, 386:657-658 (1997); Wright et al., J Mol Biol, 293: 321-31 (1999)]. For example, the N-terminal domains of the cyclin dependent kinase inhibitors p21 [Kriwacki et al., Proc. Natl. Acad. Sci. USA, 93:11504-11509 (1996); Kriwacki et al., J. Amer. Chem. Soc., 118:5320-5321 (1996)] and p27 are largely unstructured prior to binding of their cellular targets. Currently, the functional advantage(s) of the 'folding-on-binding' mechanism is not well understood. Intuitively, the loss of conformational entropy associated with folding will reduce the Gibbs free energy of binding for dynamically disordered proteins binding their targets [Kriwacki et al., *Proc. Natl. Acad. Sci. USA*, 93:11504-11509 (1996); Spolar et al., *Science*, 263:777-84 (1994)]. It has been suggested that the advantage of this mechanism is to enhance specificity [Spolar et al., *Science*, 263:777-84 (1994)] and/or to allow multiple, structurally distinct substrates to be bound [Kriwacki et al., *Proc. Natl. Acad. Sci. USA*, 93:11504-11509 (1996); Kim et al., *Nature*, 404:151-8 (2000)].

A recent computational study focused on understanding the impact of conformational entropy in protein folding [Pappu et al., *Proc Natl Acad Sci USA*, 97:12565-70 (2000)] suggests that the entropy penalty may not be as great as commonly envisioned due to steric restrictions by amino acid side chains on the vastness of polypeptide conformational space. While dynamic and highly disordered, flexible polypeptides are probably conformationally restrained in solution by steric and other interaction forces; the challenges for the future are to develop approaches to quantitatively describe these biased conformations and to relate them to biological function. The need for such studies continues to grow as more examples of biologically active, dynamically disordered proteins appear in the literature. The significance of the observations disclosed herein with the Arf: dm2 system is that, in contrast to previous observations of the folding-on-binding phenomenon involving a single disordered protein, both components of the Arf:Hdm2 system undergo folding-on-binding.

Proteins that are dynamically disordered in the native state play important roles in macromolecular recognition and the assembly of functional biomolecular complexes [Dunker, A. K.; Obradovic, Z., *Nat Biotechnol* 19:805-806 (2001); Dunker, A. K.; Brown, C. J.; Lawson, J. D.; Iakoucheva, L. M.; Obradovic, Z., *Biochemistry* 41:6573-6582 (2002); Dyson, H. J.; Wright, P. E., *Curr Opin Struct Biol* 12:54-60 (2002) and Dyson, H. J.; Wright, P. E., *Nat. Struct. Biol.* 5:499-503 (1998)]. In contrast, unfolding or misfolding is considered a prerequisite for assembly of amyloid-like fibrils from proteins that are highly structured in the native state. An emerging view is that non-native, extended polypeptide conformations are required for fibril formation [Chiti, F.; Taddei, N.; Baroni, F.; Capanni, C.; Stefani, M.; Ramponi, G.; Dobson, C. M., *Nat Struct Biol* 9:137-143 (2002)] and that protein sequences may have evolved to minimize the opportunities for their occurrence [Bucciantini, M.; Giannoni, E.; Chiti, F.; Baroni, F.; Formigli, L.; Zurdo, J.; Taddei, N.; Ramponi, G.; Dobson, C. M.; Stefani, M., *Nature* 416:507-511 (2002)]. It is well known that the formation of amyloid-like fibrils, or fibril precursors, from several different proteins is associated with degenerative diseases in humans [Dobson, C. M., *Biochem Soc Symp*, 1-26 (2001); and Koo, E. H.; Lansbury, P. T., Jr.; Kelly, J. W., *Proc Natl Acad Sci USA* 96:9989-9990 (1999)].

However, in apparent contradiction of the established relationship between fibrils and disease, the instant discloses indicates that functional domains of two proteins, Arf and Hdm2, which regulate cellular responses to stress, co-assemble into amyloid-like structures. It is believed that the instant disclosure represents the first example of self-assembly of amyloid-like fibrils involving peptides from two proteins. Accordingly, the disclosure of the instant binding interaction provides a novel mechanism for the formation of biomolecular complexes. In contrast to the pathogenic properties of fibrils formed from pure proteins, the A1/H1 peptide co-assemblies described here are associated with the interaction of Arf and Hdm2, important components of the p53 tumor suppressor pathway [Sherr, C. J. *Nat. Rev. Mol. Cell. Biol.* 2:731-737 (2001) and Sherr, C. J. *Cancer Res.* 60:3689-3695 (2000)]. It is believed that other biologically significant interactions could be mediated by a similar co-assembly mechanism.

β-strands form when dynamically disordered segments of Arf and Hdm2 interact. The formation of β-strand secondary structure is accompanied by the cooperative assembly of large supramolecular structures. The large size of these assemblies has been confirmed by gel filtration chromatography and NMR spectroscopy. For example, resonances for $^{15}$N-Hdm2 210-304 are broadened beyond detection when an excess of unlabeled mArfN37 is added to the solution. Arf: Hdm2 complexes appear to be formed by the cooperative assembly of like structural units into extended β-networks. This is supported by the appearance of the thermal denaturation curves for the mArfN37:Hdm2 210-304 assembly, which show the characteristic sigmoidal shape of a cooperative, two-state protein unfolding transition [Creighton et al., *Proteins: Structures and Molecular Properties*, W.H. Freeman & Co., New York, N.Y. (1993)]. Thermal unfolding is not reversible, however. Electrostatic forces stabilize the β-assemblies as shown by the salt-dependence of the $T_m$ values.

Through in vitro binding assays two segments of similar sequence in mouse and human Arf—the consensus for which is termed herein the Arf motif—that mediate binding to the central acidic domain of Hdm2 and that, individually, induce the formation of β-strands when mixed with the central, acidic domain of Hdm2 have been identified herein. Further, peptides derived from the Arf-binding segments of Hdm2—termed H1 and H2—induce β-strands when mixed with mArfN37. Importantly, however, the mixing of a short peptide containing either A1 or A2 with another containing either H1 or H2 does not lead to the formation of β-strands. CD was used to monitor the structural effects of peptide mixing and the concentrations used (1-10 µM) may have been below the threshold for binding of individual domains. The results disclosed herein with larger protein fragments containing either contiguous A1-A2 or H1-H2 mixed with short peptides containing a single binding segment (i.e. H1 or H2, or A1 or A2, respectively) indicate that cooperative assembly of β-strands requires two binding elements of one protein (Arf or Hdm2) and one element of the other. An exception to this is the interaction of Hdm2 210-275, which contains only the H1 binding segment, with short peptides containing either the human or mouse A1 segment. Hdm2 210-275 may contain a portion of the H2 segment that participates in cooperative interactions with its own H1 segment and the A1 segments of the peptides.

Peptides from the human and mouse A1 and A2 segments of Arf induce β-strand assembly when mixed with Hdm2 210-304. In contrast, peptides from the human and mouse A2 segment of Arf fail to induce β-strand assembly with Hdm2 210-275 but do induce β-strand assembly with Hdm2 210-304. These findings indicate that the 112 binding segment interacts only with the A2 segment of Arf. Similarly, H1 may selectively interact with A1 but, based on the data disclosed herein, A1 may also interact with H2.

It is difficult to rank the relative importance of the various modes of Arf:Hdm2 interaction (i.e. A1-H1, A2-H2, and A1-H2) with regard to biological function. However, several findings indicate that the A1 segment of human and mouse Arf plays a dominant biological role. First, Weber, et al. have examined the effects of deleting the A1 or A2 segments of full-length mouse Arf, either individually or in combination, on the ability of mouse Arf to cause cell cycle arrest [Weber et al., *Mol. Cell. Biol.*, 20:2517-2528 (2000)]. Deletion of A1, or A1 and A2 together, from mouse Arf almost completely eliminated the ability to arrest cell division while deletion of residues 26-37 that partially contain the A2 segment produced arrest in some cells but not in others. While it is difficult to quantify the differences in the biological effects of the different binding site deletion constructs, deletion of the A1 segment uniformly eliminated the ability to arrest cell division and can be ranked as the most essential Hdm2-binding element. Second, Midgley, et al., have shown that a GFP fusion protein linked to the N-terminal 20 amino acids of human Arf, which contains the human A1 segment that is almost identical to that from mouse Arf (FIG. 2a), produces Arf-like biological effects in cellular assays [Midgley et al., Oncogene, 19:2312-23 (2000)]. This result has been confirmed by Llanos, et al., using both N- and C-terminal fusions of residues 2-29 of human Arf to GFP. For Hdm2, biological data for constructs with deletions of the H1 and/or H2 segments is not available. However, the absolute conservation of amino acids within H1 from humans and mice to zebra fish and tree frogs (FIG. 2b-2c) suggests that this segment is important for biological function. Amino acids within the H2 segment are also evolutionarily conserved but not to the same degree as the H1 segment. The A1 segment of Arf and H1 of Hdm2 may play dominant biological roles; these interactions, however, may not be strong enough to support high affinity interactions and are assisted by interactions between the A2 segment of Arf and H2 of Hdm2 in the formation of Arf: Hdm7 assemblies in cells.

As further evidence that isolated domains from Arf (containing the A1 and A2 segments) and Hdm2 (containing the H1 and/or H2 segments) are functionally competent, microinjection and live cell imaging experiments demonstrate that the domains of Hdm2 that have been characterized in vitro herein, retain the ability to interact with Arf in vivo. The Hdm2 constructs 210-304 and 210-275 contain two (H1 and H2) and one (H1 only) of the Hdm2 binding segments, respectively. After nuclear microinjection, each of these constructs was re-localized to the nucleolus in the presence of GFP-p19$^{Arf}$. Since the Hdm2 NoLS has been deleted from both of these constructs, the p19$^{Arf}$ NoLS signal must be driving the nucleolar localization for both proteins. In contrast, the Hdm2 construct 277-350 relocalizes Arf to the nucleoplasm. This result confirms the presence of an Arf binding motif in Hdm2 beyond amino acid 277 and shows that, upon binding of Hdm2 277-350 to GFP-p19$^{Arf}$, the Arf NoLS becomes inaccessible to the localization machinery. This result is consistent with localization experiments performed using full length Hdm2 [Lohrum et al., Nat. Cell Biol., 2:179-81 (2000); Weber et al., Mol. Cell. Biol., 20:2517-28 (2000)]. Localization of Hdm2 277-491 to nucleoli only in the presence of p19$^{Arf}$ demonstrates that the mechanism for exposure of the cryptic Hdm2 NoLS is operative even in the absence of residues 1-176 of Hdm2. These biological results are consistent with the existence of two Arf-binding segments within the 210-350 segment of Hdm2, as identified through in vitro assays using short peptides and protein fragments.

A novel mechanism of protein-protein interaction mediates Arf:Hdm2 binding. The strict requirement for the presence of both proteins—Arf and Hdm2—for the formation of β-strand-containing assemblies differentiates this system from others that utilize the folding-on-binding mechanism. Further, while the Arf:Hdm2 system is similar to amyloid proteins in that they form extended networks comprised of β-strands, the individual components of the Arf:Hdm2 system fail to form β-assemblies alone under a wide range of solution conditions. While many proteins will form amyloid-like aggregates with β-fibril structure [Booth et al., Nature, 385:787-93 (1997); Ohnishi et at, J. Mol. Biol., 301:477-89 (2000); Alexandrescu and RathgebSzabo, J Mol Biol, 291: 1191-206 (1999); [Esposito et al., Protein Sci., 9:831-845 (2000); Chiti et al., EMBO J., 19:1441-1449 (2000); Wilkins et al., Eur. J. Biochem., 267:2609-2616 (2000)], Arf and Hdm2 form β-assemblies only when both components are present. Insight into the two-component, folding-on-binding phenomenon can be gained by considering the unusual amino acid composition of the interacting segments of Arf and Hdm2 (i.e. A1, and A2, and H1 and H2). As previously reported, the N-termini of both human and mouse Arf are unusually rich in Arg residues [DiGiammarino et al., Biochem., 40:2379-2386 (2001)]. Electrostatic repulsion between these Arg residues may cause the polypeptide to be dynamically disordered. Interestingly, the Arf-binding segments of Hdm2 identified here (H1 and H2) are rich in acidic residues. The carboxylate groups of these acidic residues probably interact with the guanidinium groups of Arg residues within the A1 and A2 segments of Arf via electrostatic interactions. The ability of salt to reduce the $T_m$ value for the mArfN37:Hdm2 210-304 assembly strongly supports the idea that electrostatic interactions stabilize Arf:Hdm2 assemblies. In the absence of Arf, the acidic residues within the Arf-binding segments of Hdm2 (H1 and H2) repel each other, producing the dynamically disordered conformations observed here. Interestingly, the Jpred secondary structure prediction algorithm predicts β-strand conformations exactly within the segments of Arf and Hdm2 which have been shown to be important for molecular interactions (FIGS. 2a-2c). Thus, the sequences within these segments (A1 and A2, and H1 and H2) are consistent with extended, β-strand conformations. However, the high frequency of like-charged residues within them may cause the individual polypeptides to be dynamically disordered. It is also possible that the β-strand regions of φ, ψ conformational space are populated within the H1 and H2 segments and that the methods of analysis (CD and NMR) used have failed to detect them.

In addition to electrostatic interactions, Arf:Hdm2 interactions are likely to be mediated by hydrophobic interactions. The Arg residues of the Arf motif (FIG. 4) are separated by a string of hydrophobic residues, including a highly conserved segment with the sequence FLV. In an extended conformation, the arrangement of Arg and hydrophobic residues within the Arf motif would give rise to both types of residues (hydrophobic and Arg) on both faces of a β-pleated sheet. In the H1 segment of Hdm2, acidic residues and hydrophobic residues alternate within the sequence (FIG. 2b). This situation would allow acidic residues of Hdm2 to interact with Arg residues of Arf in the context of β-strands composed of intermingled A1 (or A2) and H1 segments. Hydrophobic residues of H1 would align, on the opposite face, with hydrophobic residues of the Arf motif. The conclusion that both electrostatic and hydrophobic forces stabilize Arf:Hdm2 β-assemblies is consistent with their high degree of stability, as exemplified by resistance to denaturation by urea, detergent, salt and extremes of pH. It would appear reasonable that these highly stable structures would be favored within the cellular environment as well as in vitro. It is of interest that the nucleolus, where Arf and Hdm2 are localized, was originally characterized by its granular and fibrillar nature [Olson et al., Trends Cell Biol., 10:189-96 (2000)] that is, in principle, consistent with the extended structures reported here for Arf and Hdm2.

The biological function of Hdm2 is, in part, to maintain p53 at low levels by actively controlling its ubiquitination, nuclear export and proteosome-dependent degradation. The early observation that Arf leads to sequestration of Hdm2 within nucleoli suggested that Arf inhibited Hdm2-dependent degradation of p53 by physically separating the destroyer, Hdm2, from it target, p53. However, whether Arf inhibits the destroyer function of nucleoplasmic Hdm2, which has access to p53, has been an open question. Llanos, et al., have recently reported that truncated forms of human Arf that fail to localize within nucleoli maintain the ability to stabilize and activate p53 [Llanos et al., *Nat. Cell Biol.*, 3:445-452 (2001)]. This suggests that the binding of Arf to Hdm2 within the nucleoplasm, which may occur prior to nucleolar colocalization, directly inhibits some or all of the destroyer functions of Hdm2 toward p53. Hdm2 is comprised of several domains that mediate p53 binding (N-terminal helical domain) [Kussie et al., *Science*, 274:948-953 (1996)], Arf binding (acidic domain studied here), and p53 ubiquitination (C-terminal RING domain) [Geyer et al., *Nat. Cell Biol.*, 2:569-73 (2000); Fang et al., *J. Biol. Chem.*, 275:8945-8951 (2000)]. Lohrum, et al., have shown that when Arf binds Hdm2, the NoLS of Arf is hidden and a cryptic NoLS within the RING domain of Hdm2 is revealed, leading to nucleolar colocalization [Lohrum et al., *Nat. Cell Biol.*, 2:179-81 (2000)]. Consistent with the RING domain of Hdm2 (and Mdm2) playing an important role in p53 ubiquitination, nuclear export and degradation [Geyer et al., *Nat. Cell Biol.*, 2:569-73 (2000); Fang et al., *J. Biol. Chem.*, 275:8945-8951 (2000); Honda and Yasuda, *Oncogene*, 19:1473-1476 (2000); Argentini et al., *Oncogene*, 19:3849-3857 (2000); Boyd et al., *Nat. Cell Biol.*, 2:563-568 (2000)], when Arf binds the central, acidic domain of Hdm2 it not only exposes a cryptic NoLS within the Hdm2 RING domain but also alters the structure and function of this domain in the context of E3 ubiquitin ligase activity. The structure of the UbcH7/Cb1 E2/E3 complex [Zheng et al., *Cell*, 102:533-539 (2000)] shows that the RING domain within the Cb1 E3 subunit interacts with the UbcH7 E2 and serves to orient the E2 with respect to a small peptide derived from Zap-70, a target of this E2/E3 complex. The RING domain of Hdm2 can play a similar 'orienting' role within the E2/E3 complex that targets p53. The binding of Arf to Hdm2 can alter the conformation of the Hdm2 RING domain to expose the cryptic NoLS and inhibit the orienting function of the RING domain. It is likely that intramolecular interaction between the domains of Hdm2 hide the cryptic NoLS and maintain the RING domain in an active E3 ubiquitin ligase conformation. Arf binding, through the interactions described herein, can disrupt inter-domain interactions, revealing the cryptic NoLS and inhibiting E3 ubiquitin ligase activity toward p53.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

REFERENCES

1. Sherr, C. J. (2000). The Pezcoller lecture: cancer cell cycles revisited. *Cancer Res.*, 60, 3689-95.
2. Quelle, D. E., Zindy, F., Ashmun, R. A. & Sherr, C. J. (1995). Alternative reading frames of the INK4a tumor suppressor gene encode two unrelated proteins capable of inducing cell cycle arrest. *Cell*, 83, 993-1000.
3. Serrano, M., Hannon, G. J. & Beach, D. (1993). A new regulatory motif in cell-cycle control causing specific inhibition of cyclin D/CDK4. *Nature*, 366, 704-707.
4. Sherr, C. J. (1998). Tumor Surveillance via the ARF-p53 pathway. *Genes Dev.*, 12, 2984-2991.
5. Serrano, M., Lee, H., Chin, L., Cordon-Cardo, C., Beach, D. & DePinho, R. A. (1996). Role of the INK4a locus in tumor suppression and cell mortality. *Cell*, 85, 27-37.
6. Kamijo, T., Zindy, F., Roussel, M. F., Quelle, D. E., Downing, J. R., Ashmun, R. A., Grosveld, G. & Sherr, C. J. (1997). Tumor suppression at the mouse INK4a locus mediated by the alternative reading frame product p19ARF. *Cell*, 91, 1-20.
7. Raus, M. & Peters, G. (1998). The p16INK4A/CDKN2A tumor suppressor and its relatives. *Biochim. Biophys. Acta Rev. Cancer*, 1378, F115-F177.
8. Zindy, F., Eischen, C. M., Randle, D. H., Kamijo, T., Cleveland, J. L., Sherr, C. J. & Roussel, M. F. (1998). Myc signaling via the ARF tumor suppressor regulates p53-dependent apoptosis and immortalization. *Genes & Dev.*, 12, 2424-2434.
9. de Stanchina, E. et al. (1998). E1A signaling to p53 involves the p19(ARF) tumor suppressor. *Genes Dev.*, 12, 2434-42.
10. Bates, S., Phillips, A. C., Clark, P. A., Stott, F., Peters, G., Ludwig, R. L. & Vousden, K. H. (1998). p14ARF links the tumour suppressors RB and p53. *Nature*, 395, 124-5.
11. Palmero, I., Pantoja, C. & Serrano, M. (1998). p19ARF links the tumour suppressor p53 to Ras. *Nature*, 395, 125-6.
12. Radfar, A., Unnikrishnan, I., Lee, H. W., DePinho, R. A. & Rosenberg, N. (1998). p19(Arf) induces p53-dependent apoptosis during abelson virus-mediated pre-B cell transformation. *Proc. Natl. Acad. Sci. U.S.A.*, 95, 13194-13199.
13. Pomerantz, J. et al. (1998). The Ink4a tumor suppressor gene product, p19Arf, interacts with MDM2 and neutralizes MDM2's inhibition of p53. *Cell*, 92, 713-23.
14. Kamijo, T., Weber, J. D., Zambetti, G., Zindy, P., Roussel, M. F. & Sherr, C. J. (1998). Functional and Physical Interactions of the ARF Tumor Suppressor with p53 and Mdm2. *Proc. Natl. Acad. Sci.*, 95, 8292-8297.
15. Stott, F. J. et al. (1998). The alternative product from the human CDKN2A locus, p14(ARF), participates in a regulatory feedback loop with p53 and MDM2. *Embo J*, 17, 5001-14.
16. Zhang, Y. P., Xiong, Y. & Yarbrough, W. G. (1998). ARF promotes MDM2 degradation and stabilizes p53 Arf-INK4A locus deletion impairs both the Rb and p53 tumor suppressor pathways. *Cell*, 92, 725-734.
17. Wu, X. W., Bayle, J. H., Olson, D. & Levine, A. J. (1993). The p53-mdm-2 autoregulatory feedback loop. *Genes Dev.*, 7, 1126-1132.
18. Barak, Y., Juven, T., Haffner, R. & Oren, M. (1993) mdm2 expression is induced by wild type p53 activity. *EMBO J.*, 12, 461-468.
19. Kussie, P. H., Gonna, S., Marechal, V., Elenbaas, B., Moreau, J., Levine, A. J. & Pavletich, N. P. (1996). Structure of the MDM2 oncoprotein bound to the p53 tumor suppressor transactivation domain. *Science*, 274, 948-953.
20. Oliner, J. D., Pietenpol, J. A., Thiagalingam, S., Gyuris, J., Kinzler, K. W. & Volgelstein, B. (1993). Oncoprotein Mdm2 Conceals the Activation Domain of Tumor Suppressor p53. *Nature*, 362, 857-860.
21. Momand, J., Zambetti, G. P., Olson, D. C., George, D. & Levine, A. J. (1992). The mdm-2 oncogene product forms a complex with the p53 protein and inhibits p53-mediated transactivation. *Cell*, 69, 1237-1245.

22. Roth, J., Dobbelstein, M., Freedman, D. A., Shenk, T. & Levine, A. J. (1998). Nucleo-cytoplasmic shuttling of the hdm2 oncoprotein regulates the levels of the p53 protein via a pathway used by the human immunodeficiency virus rev protein. *Embo J*, 17, 554-64.
23. Freedman, D. A. & Levine, A. J. (1998). Nuclear export is required for degradation of endogenous p53 by MDM2 and human papillomavirus E6. *Mol Cell Biol*, 18, 7288-93.
24. Honda, R., Tanaka, H. & Yasuda, H. (1997). Oncoprotein MDM2 is a ubiquitin ligase E3 for tumor suppressor p53. *FEBS Lett*, 420, 25-7.
25. Donehower, L. A., Harvey, M., Slagle, B. L., McArthur, M. J., Montgomery, C. A. J., Butel, J. S. & Bradley, A. (1992). Mice deficient for p53 are developmentally normal but susceptible to spontaneous tumours. *Nature*, 356, 215-221.
26. Jones, S. N., Roe, A. E., Donehower, L. A. & Bradley, A. (1995). Rescue of embryonic lethality in Mdm2-deficient mice by absence of p53. *Nature*, 378, 206-8.
27. Montes de Oca Luna, R., Wagner, D. S. & Lozano, G. (1995). Rescue of early embryonic lethality in mdm2-deficient mice by deletion of p53. *Nature*, 378, 203-206.
28. Tao, W. & Levine, A. J. (1999). P19(ARF) stabilizes p53 by blocking nucleo-cytoplasmic shuttling of Mdm9. *Proc Natl Acad Sci USA*, 96, 6937-41.
29. Honda, R. & Yasuda, H. (1999). Association of p19(ARF) with Mdm2 inhibits ubiquitin ligase activity of Mdm2 for tumor suppressor p53. *Embo J*, 18, 22-7.
30. Midgley, C. A., Desterro, J. M., Saville, M. K., Howard, S., Sparks, A., Hay, R. T. & Lane, D. P. (2000). An N-terminal p14ARF peptide blocks Mdm2-dependent ubiquitination in vitro and can activate p53 in vivo. *Oncogene*, 19, 2312-23.
31. Llanos, S., Clark, P. A., Rowe, J. & Peters, G. (2001). Stabilization of p53 by p14ARF without relocation of MDM2 to the nucleolus. *Nat. Cell Biol.*, 3, 445-452.
32. Weber, J. D., Taylor, L. J., Roussel, M. F., Sherr, C. J. & Bar-Sagi, D. (1999). Nucleolar Arf sequesters Mdm2 and activates p53. *Nat. Cell Biol.*, 1, 20-26.
33. Lohrum, M. A., Ashcroft, M., Kubbutat, M. H. & Vousden, K. H. (2000). Identification of a cryptic nucleolar-localization signal in MDM2. *Nat. Cell Biol.*, 2, 179-81.
34. Weber, J. D., Kuo, M. L., Bothner, B., DiGiammarino, E. L., Kriwacki, R. W., Roussel, M. F. & Sherr, C. J. (2000). Cooperative Signals governing ARF-mdm2 interaction and nucleolar localization of the complex. *Mol. Cell. Biol.*, 20, 2517-2528.
35. DiGiammarino, E. L., Filippov, I., Weber, J. D., Bothner, B. & Kriwacki, R. W. (2001). Solution Structure of the p53 Regulatory Domain of the p19Arf Tumor Suppressor Protein. *Biochem.*, 40, 2379-2386.
36. Zhang, Y. & Xiong, Y. (1999). Mutations in human ARF exon 2 disrupt its nucleolar localization and impair its ability to block nuclear export of MDM2 and p53. *Mol. Cell*, 3, 579-91.
37. Grossman, S. R., Perez, M., Kung, A. L., Joseph, M., Mansur, C., Xiao, Z. X., Kumar, S., Howley, P. M. & Livingston, D. M. (1998). p300/Mdm2 complexes participate in Mdm2-mediated p53 degradation. *Mol Cell*, 2, 405-15.
38. Martin, K., Trouche, D., Hagemeier, C., Sorensen, T. S., La Thangue, N. B. & Kouzarides, T. (1995). Stimulation of E2F1/DP1 transcriptional activity by MDM2 oncoprotein. *Nature*, 375, 691-4.
39. O'Connor, D. J., Lam, E. W., Griffin, S., Zhong, S., Leighton, L. C., Burbidge, S. A. & Lu, X. (1995). Physical and functional interactions between p53 and cell cycle co-operating transcription factors, E2F1 and DP1. *Embo J*, 14, 6184-92.
40. Xiao, Z. X., Chen, J., Levine, A. J., Modjtahedi, N., Xing, J., Sellers, W. R. & Livingston, D. M. (1995). Interaction between the retinoblastoma protein and the oncoprotein MDM2. *Nature*, 375, 694-8.
41. Marechal, V., Elenbaas, B., Piette, J., Nicolas, J. C. & Levine, A. J. (1994). The ribosomal L5 protein is associated with mdm-2 and mdm-2-p53 complexes. *Mol Cell Biol*, 14, 7414-20.
42. Leveillard, T., Gorry, P., Niederreither, K. & Wasylyk, B. (1998). MDM2 expression during mouse embryogenesis and the requirement of p53. *Mech Dev*, 74, 189-93.
43. Boddy, M. N., Freemont, P. S. & Borden, K. L. (1994). The p53-associated protein MDM2 contains a newly characterized zinc-binding domain called the RING finger. *Trends Biochem Sci*, 19, 198-9.
44. Elenbaas, B., Dobbelstein, M., Roth, J., Shenk, T. & Levine, A. J. (1996). The MDM2 oncoprotein binds specifically to RNA through its RING finger domain. *Mol. Med.*, 2, 439-51.
45. Lai, Z., Freedman, D. A., Levine, A. J. & McLendon, G. L. (1998). Metal and RNA binding properties of the hdm2 RING finger domain. *Biochem.*, 37, 17005-15.
46. Schwarzinger, S., Kroon, G. J. A., Foss, T. R., Chuung, J., Wright, P. E. & Dyson, H. J. (2001). Sequence-dependent correction of random coil NMR chemical shifts. *J. Amer. Chem. Soc.*, 123; 2970-2978.
47. Kriwacki, R. W., Hengst, L., Tennant, L., Reed, S. I. & Wright, P. E. (1996). Structural studies of p21 (waf1/cip1/sdi1) in the free and Cdk2-bound state: Conformational disorder mediates binding diversity. *Proc. Natl. Acad. Sci. USA*, 93, 11504-11509.
48. Cuff, J. A. & Barton, G. J. (2000). Application of multiple sequence alignment profiles to improve protein secondary structure prediction. *Proteins*, 40, 502-11.
49. Uversky, V. N., Karnoup, A. S., Khurana, R., Segel, D. J., Doniach, S. & Fink, A. L. (1999). Association of partially-folded intermediates of staphylococcal nuclease induces structure and stability. *Protein Sci.*, 8, 161-73.
50. Sosnick, T. R., Jackson, S., Wilk, R. R., Englander, S. W. & DeGrado, W. F. (1996). The role of helix formation in the folding of a fully alpha-helical coiled coil. *Proteins*, 24, 427-32.
51. Dyson, H. J. & Wright, P. E. (1998). Equilibrium NMR studies of unfolded and partially folded proteins. *Nat. Struct. Biol.*, 5, 499-503.
52. Plaxco, K. W. & Gross, M. (1997). The importance of being unfolded. *Nature*, 386, 657-658.
53. Wright, P. E. & Dyson, H. J. (1999). Intrinsically unstructured proteins: re-assessing the protein structure-function paradigm. *J Mol Biol*, 293, 321-31.
54. Kriwacki, R. W., Wu, J., Siuzdak, G. & Wright, P. E. (1996). Probing Protein/Protein Interactions with Mass Spectrometry and Isotopic Labeling: Analysis of the p21/Cdk2 Complex. *J. Amer. Chem. Soc.*, 118, 5320-5321.
55. Spolar, R. S. & Record, M. T. J. (1994). Coupling of local folding to site-specific binding of proteins to DNA. *Science*, 263, 777-84.
56. Kim, A. S., Kakalis, L. T., Abdul-Manan, N., Liu, G. A. & Rosen, M. K. (2000). Autoinhibition and activation mechanisms of the Wiskott-Aldrich syndrome protein. *Nature*, 404, 151-8.

57. Pappu, R. V., Srinivasan, R. & Rose, G. D. (2000). The Flory isolated-pair hypothesis is not valid for polypeptide chains: implications for protein folding. *Proc Natl Acad Sci USA*, 97, 12565-70.
58. Creighton, T. E. (1993) *Proteins: Structures and Molecular Properties*, W.H. Freeman & Co., New York, N.Y.
59. Weber, J. D., Kuo, M. L., Bothner, B., DiGiammarino, E. L., Kriwacki, R. W., Roussel, M. F. & Sherr, C. J. (2000). Cooperative signals governing ARF-mdm9 interaction and nucleolar localization of the complex. *Mol. Cell. Biol.*, 20, 2517-28.
60. Booth, D. R. et al. (1997). Instability, unfolding and aggregation of human lysozyme variants underlying amyloid fibrillogenesis. *Nature*, 385, 787-93.
61. Ohnishi, S., Koide, A. & Koide, S. (2000). Solution conformation and amyloid-like fibril formation of a polar peptide derived from a beta-hairpin in the OspA single-layer beta-sheet. *J. Mol. Biol.*, 301, 477-89.
62. Alexandrescu, A. T. & Rathgeb-Szabo, K. (1999). An NMR investigation of solution aggregation reactions preceding the misassembly of acid-denatured cold shock protein A into fibrils. *J Mol Biol*, 291, 1191-206.
63. Esposito, G. et al. (2000). Removal of the N-terminal hexapeptide from human beta2-microglobulin facilitates protein aggregation and fibril formation. *Protein Sci.*, 9, 831-845.
64. Chiti, F., Taddei, N., Bucciantini, M., White, P., Ramponi, G. & Dobson, C. M. (2000). Mutational analysis of the propensity for amyloid formation by a globular protein. *EMBO J.*, 19, 1441-1449.
65. Wilkins, D. K., Dobson, C. M. & Gross, M. (2000). Biophysical studies of the development of amyloid fibrils from a peptide fragment of cold shock protein B. *Eur. J. Biochem.*, 267, 2609-2616.
66. Olson, M. O., Dundr, M. & Szebeni, A. (2000). The nucleolus: an old factory with unexpected capabilities. *Trends Cell Biol.*, 10, 189-96.
67. Geyer, R. K., Yu, Z. K. & Maid, C. G. (2000). The MDM2 RING-finger domain is required to promote p53 nuclear export. *Nat. Cell Biol.*, 2, 569-73.
68. Fang, S., Jensen, J. P., Ludwig, R. L., Vousden, K. H. & Weissman, A. M. (2000). Mdm2 is a RING finger-dependent ubiquitin protein ligase for itself and p53. *J. Biol. Chem.*, 275, 8945-8951.
69. Honda, R. & Yasuda, H. (2000). Activity of MDM2, a ubiquitin ligase, toward p53 or itself is dependent on the RING finger domain of the ligase. *Oncogene*, 19, 1473-1476.
70. Argentini, M., Barboule, N. & Wasylyk, B. (2000). The contribution of the RING finger domain of MDM2 to cell cycle progression. *Oncogene*, 19, 3849-3857.
71. Boyd, S. D., Tsai, K. Y. & Jacks, T. (2000). An intact HDM2 RING-finger domain is required for nuclear exclusion of p53. *Nat. Cell Biol.*, 2, 563-568.
72. Zheng, N., Wang, P., Jeffrey, P. D. & Pavletich, N. P. (2000). Structure of a c-Cb1-UbcH7 complex: RING domain function in ubiquitin-protein ligases. *Cell*, 102, 533-539.
73. Muller, L. (1979). Sensitivity enhanced detection of weak nuclei using heteronuclear multiple quantum coherence. *J. Amer. Chem. Soc.*, 101, 4481-4484.
74. Bodenhausen, G. & Ruben, D. J. (1980). Natural abundance nitrogen-15 NMR by enhanced heteronuclear spectroscopy. *Chem. Phys. Lett.*, 69, 185-189.
75. Farrow, N. A. et al. (1994). Backbone dynamics of a free and a phosphopeptide-complexed Src homology 2 domain studied by 15N NMR relaxation. *Biochem.*, 33, 5984-6003.

Various publications, patent applications and patents are cited herein, the disclosures of which are incorporated by reference in their entireties.

What is claimed is:

1. A method of identifying a compound that can induce the formation of a β-strand assembly of a Double Minute-2 (Dm2) polypeptide comprising:
   (a) contacting a compound with a Dm2 polypeptide selected from the group consisting of a polypeptide consisting of amino acid residues 235-259 of SEQ ID NO:8 and a polypeptide consisting of amino acid residues 275-289 of SEQ ID NO:8, wherein the Dm2 polypeptide can induce β-strand assembly with an Arf polypeptide (Alternative Reading Frame-p 19/Alternative Reading Frame-pI 4 polypeptide) set forth in SEQ ID NO: 4; and
   (b) determining in vitro whether the Dm2 polypeptide is induced to form a β-strand assembly; wherein a compound is identified when the Dm2 polypeptide is induced to form a β-strand assembly in the presence of the compound and not in the absence of the compound.

2. The method of claim 1 wherein said determining is performed by circular dichroism measurements.

3. The method of claim 1 wherein said determining is performed by Fourier Transform Infra-red spectroscopy.

4. A method of identifying a compound that can induce the formation of supramolecular assemblies comprised of β-strands of a Double Minute-2 (Dm2) polypeptide comprising:
   (a) contacting a compound with a Dm2 polypeptide selected from the group consisting of a polypeptide consisting of amino acid residues 235-259 of SEQ ID NO:8 and a polypeptide consisting of amino acid residues 275-289 of SEQ ID NO:8, wherein said Dm2 polypeptide can induce the β-strand assembly with an Arf polypeptide (Alternative Reading Frame-p 19/Alternative Reading Frame-pI 4 polypeptide) set forth in SEQ ID NO: 4; and
   (b) determining in vitro whether the Dm2 polypeptide is induced to form supramolecular assemblies comprised of β-strands of the Dm2 polypeptide in the presence of the compound and not in the absence of the compound, wherein when the Dm2 polypeptide is induced to form supramolecular assemblies the compound is identified as a compound that can induce the formation of supramolecular assemblies comprised of β-strands of Dm2.

* * * * *